US009504483B2

(12) United States Patent
Houser et al.

(10) Patent No.: US 9,504,483 B2
(45) Date of Patent: Nov. 29, 2016

(54) SURGICAL INSTRUMENTS

(75) Inventors: Kevin L. Houser, Springboro, OH (US); Foster B. Stulen, Mason, OH (US); Andrew M. Zwolinski, Cincinnati, OH (US); Matthew C. Miller, Cincinnati, OH (US); Tracy D. Lopes, Mason, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 545 days.

(21) Appl. No.: 13/540,916

(22) Filed: Jul. 3, 2012

(65) Prior Publication Data
US 2012/0269676 A1 Oct. 25, 2012

Related U.S. Application Data

(62) Division of application No. 11/726,760, filed on Mar. 22, 2007, now Pat. No. 8,226,675.

(51) Int. Cl.
*A61B 17/32* (2006.01)
*A61B 17/00* (2006.01)
*A61B 17/22* (2006.01)

(52) U.S. Cl.
CPC ............ *A61B 17/320068* (2013.01); *A61B 17/320092* (2013.01); *A61B 2017/00477* (2013.01); *A61B 2017/22011* (2013.01); *A61B 2017/320088* (2013.01)

(58) Field of Classification Search
CPC ............ A61B 17/320068; A61B 17/320092; A61B 2017/00477; A61B 2017/320088
USPC ................ 604/22; 606/79, 84, 167, 169–171
See application file for complete search history.

(56) References Cited

U.S. PATENT DOCUMENTS

| 969,528 | A | 9/1910 | Disbrow |
|---|---|---|---|
| 1,570,025 | A | 1/1926 | Young |
| 1,813,902 | A | 7/1931 | Bovie |
| 2,442,966 | A | 6/1948 | Wallace |
| 2,704,333 | A | 3/1955 | Calosi et al. |
| 2,736,960 | A | 3/1956 | Armstrong |
| 2,849,788 | A | 9/1958 | Creek |
| 2,874,470 | A | 2/1959 | Richards |
| 2,990,616 | A | 7/1961 | Balamuth et al. |
| RE25,033 | E | 8/1961 | Balamuth et al. |
| 3,015,961 | A | 1/1962 | Roney |
| 3,053,124 | A | 9/1962 | Balamuch et al. |
| 3,082,805 | A | 3/1963 | Royce |

(Continued)

FOREIGN PATENT DOCUMENTS

| AU | 2003241752 A1 | 9/2003 |
|---|---|---|
| CN | 1634601 A | 7/2005 |

(Continued)

OTHER PUBLICATIONS

International Search Report for PCT/US08/57441, Nov. 4, 2008 (5 pages).

(Continued)

*Primary Examiner* — Ashley Fishback

(57) ABSTRACT

A surgical instrument includes an elongated transmission waveguide defining a longitudinal axis. The transmission waveguide has a distal end and a proximal end. The at least one strike surface is formed on the proximal end and is configured to receive vibratory energy.

12 Claims, 19 Drawing Sheets

(56) References Cited

U.S. PATENT DOCUMENTS

| | | |
|---|---|---|
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,526,219 A | 9/1970 | Balamuth |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,776,238 A | 12/1973 | Peyman et al. |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 4,012,647 A | 3/1977 | Balamuth et al. |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,444 A | 5/1980 | Bonnell et al. |
| 4,300,083 A | 11/1981 | Heiges |
| 4,302,728 A | 11/1981 | Nakamura |
| 4,306,570 A | 12/1981 | Matthews |
| 4,445,063 A | 4/1984 | Smith |
| 4,491,132 A | 1/1985 | Aikins |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,545,374 A | 10/1985 | Jacobson |
| 4,574,615 A | 3/1986 | Bower et al. |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,708,127 A | 11/1987 | Abdelghani |
| 4,712,722 A | 12/1987 | Hood et al. |
| 4,808,154 A | 2/1989 | Freeman |
| 4,819,635 A | 4/1989 | Shapiro |
| 4,827,911 A | 5/1989 | Broadwin et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,850,354 A | 7/1989 | McGurk-Burleson et al. |
| 4,852,578 A | 8/1989 | Companion et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,881,550 A | 11/1989 | Kothe |
| 4,896,009 A | 1/1990 | Pawlowski |
| 4,903,696 A | 2/1990 | Stasz et al. |
| 4,915,643 A | 4/1990 | Samejima et al. |
| 4,922,902 A | 5/1990 | Wuchinich et al. |
| 4,965,532 A | 10/1990 | Sakurai |
| 4,979,952 A | 12/1990 | Kubota et al. |
| 4,981,756 A | 1/1991 | Rhandhawa |
| 5,013,956 A | 5/1991 | Kurozumi et al. |
| 5,015,227 A | 5/1991 | Broadwin et al. |
| 5,026,370 A | 6/1991 | Lottick |
| 5,026,387 A | 6/1991 | Thomas |
| 5,042,707 A | 8/1991 | Taheri |
| 5,084,052 A | 1/1992 | Jacobs |
| 5,105,117 A | 4/1992 | Yamaguchi |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,162,044 A | 11/1992 | Gahn et al. |
| 5,163,421 A | 11/1992 | Bernstein et al. |
| 5,163,537 A | 11/1992 | Radev |
| 5,167,725 A | 12/1992 | Clark et al. |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,209,719 A | 5/1993 | Baruch et al. |
| 5,213,569 A | 5/1993 | Davis |
| 5,214,339 A | 5/1993 | Naito |
| 5,218,529 A | 6/1993 | Meyer et al. |
| 5,221,282 A | 6/1993 | Wuchinich |
| 5,226,909 A | 7/1993 | Evans et al. |
| 5,226,910 A | 7/1993 | Kajiyama et al. |
| 5,241,236 A | 8/1993 | Sasaki et al. |
| 5,241,968 A | 9/1993 | Slater |
| 5,242,460 A | 9/1993 | Klein et al. |
| 5,254,129 A | 10/1993 | Alexander |
| 5,257,988 A | 11/1993 | L'Esperance, Jr. |
| 5,261,922 A | 11/1993 | Hood |
| 5,263,957 A | 11/1993 | Davison |
| 5,264,925 A | 11/1993 | Shipp et al. |
| 5,275,166 A | 1/1994 | Vaitekunas et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,312,023 A | 5/1994 | Green et al. |
| 5,312,425 A | 5/1994 | Evans et al. |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,387,215 A | 2/1995 | Fisher |
| 5,389,098 A | 2/1995 | Tsuruta et al. |
| 5,394,187 A | 2/1995 | Shipp |
| 5,396,266 A | 3/1995 | Brimhall |
| 5,403,312 A | 4/1995 | Yates et al. |
| 5,403,334 A | 4/1995 | Evans et al. |
| 5,408,268 A | 4/1995 | Shipp |
| D358,887 S | 5/1995 | Feinberg |
| 5,411,481 A | 5/1995 | Allen et al. |
| 5,419,761 A | 5/1995 | Narayanan et al. |
| 5,421,829 A | 6/1995 | Olichney et al. |

(56) References Cited

U.S. PATENT DOCUMENTS

| | | |
|---|---|---|
| 5,423,844 A | 6/1995 | Miller |
| 5,438,997 A | 8/1995 | Sieben et al. |
| 5,445,639 A | 8/1995 | Kuslich et al. |
| 5,449,370 A | 9/1995 | Vaitekunas |
| 5,451,220 A | 9/1995 | Ciervo |
| 5,456,684 A | 10/1995 | Schmidt et al. |
| 5,471,988 A | 12/1995 | Fujio et al. |
| 5,472,443 A | 12/1995 | Cordis et al. |
| 5,478,003 A | 12/1995 | Green et al. |
| 5,483,501 A | 1/1996 | Park et al. |
| 5,486,162 A | 1/1996 | Brumbach |
| 5,490,860 A | 2/1996 | Middle et al. |
| 5,500,216 A | 3/1996 | Julian et al. |
| 5,501,654 A | 3/1996 | Failla et al. |
| 5,505,693 A | 4/1996 | Mackool |
| 5,507,738 A | 4/1996 | Ciervo |
| 5,527,331 A | 6/1996 | Kresch et al. |
| 5,540,693 A | 7/1996 | Fisher |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,573,424 A | 11/1996 | Poppe |
| 5,577,654 A | 11/1996 | Bishop |
| 5,591,187 A | 1/1997 | Dekel |
| 5,593,414 A | 1/1997 | Shipp et al. |
| 5,601,601 A | 2/1997 | Tal et al. |
| 5,603,773 A | 2/1997 | Campbell |
| 5,607,436 A | 3/1997 | Pratt et al. |
| 5,618,304 A | 4/1997 | Hart et al. |
| 5,618,492 A | 4/1997 | Auten et al. |
| 5,620,447 A | 4/1997 | Smith et al. |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| D381,077 S | 7/1997 | Hunt |
| 5,651,780 A | 7/1997 | Jackson et al. |
| 5,653,713 A | 8/1997 | Michelson |
| 5,669,922 A | 9/1997 | Hood |
| 5,674,235 A | 10/1997 | Parisi |
| 5,678,568 A | 10/1997 | Uchikubo et al. |
| 5,690,269 A | 11/1997 | Bolanos et al. |
| 5,694,936 A | 12/1997 | Fujimoto et al. |
| 5,704,534 A | 1/1998 | Huitema et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,717,306 A | 2/1998 | Shipp |
| 5,728,130 A | 3/1998 | Ishikawa et al. |
| 5,730,752 A | 3/1998 | Alden et al. |
| 5,733,074 A | 3/1998 | Stöck et al. |
| 5,741,226 A | 4/1998 | Strukel et al. |
| 5,766,164 A | 6/1998 | Mueller et al. |
| 5,772,659 A | 6/1998 | Becker et al. |
| 5,792,135 A | 8/1998 | Madhani et al. |
| 5,792,138 A | 8/1998 | Shipp |
| 5,792,165 A | 8/1998 | Klieman et al. |
| 5,805,140 A | 9/1998 | Rosenberg et al. |
| 5,808,396 A | 9/1998 | Boukhny |
| 5,810,859 A | 9/1998 | DiMatteo et al. |
| 5,817,084 A | 10/1998 | Jensen |
| 5,817,119 A | 10/1998 | Klieman et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,957 A | 11/1998 | Schulz et al. |
| 5,843,109 A | 12/1998 | Mehta et al. |
| 5,851,212 A | 12/1998 | Zirps et al. |
| 5,858,018 A | 1/1999 | Shipp et al. |
| 5,873,873 A | 2/1999 | Smith et al. |
| 5,873,882 A | 2/1999 | Straub et al. |
| 5,878,193 A | 3/1999 | Wang et al. |
| 5,879,364 A | 3/1999 | Bromfield et al. |
| 5,883,615 A | 3/1999 | Fago et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,627 A | 5/1999 | Spaulding |
| 5,906,628 A | 5/1999 | Miyawaki et al. |
| 5,911,699 A | 6/1999 | Anis et al. |
| 5,916,229 A | 6/1999 | Evans |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,024,741 A | 2/2000 | Williamson, IV et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,048,224 A | 4/2000 | Kay |
| 6,050,943 A | 4/2000 | Slayton et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,096,033 A | 8/2000 | Tu et al. |
| 6,099,542 A | 8/2000 | Cohn et al. |
| 6,109,500 A | 8/2000 | Alli et al. |
| 6,110,127 A | 8/2000 | Suzuki |
| 6,113,594 A | 9/2000 | Savage |
| 6,117,152 A | 9/2000 | Huitema |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,147,560 A | 11/2000 | Erhage et al. |
| 6,152,902 A | 11/2000 | Christian et al. |
| 6,154,198 A | 11/2000 | Rosenberg |
| 6,159,160 A | 12/2000 | Hsei et al. |
| 6,159,175 A | 12/2000 | Strukel et al. |
| 6,162,194 A | 12/2000 | Shipp |
| 6,165,150 A | 12/2000 | Banko |
| 6,174,310 B1 | 1/2001 | Kirwan, Jr. |

(56) References Cited

U.S. PATENT DOCUMENTS

| | | |
|---|---|---|
| 6,179,853 B1 | 1/2001 | Sachse et al. |
| 6,183,426 B1 | 2/2001 | Akisada et al. |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,233,476 B1 | 5/2001 | Strommer et al. |
| 6,238,366 B1 | 5/2001 | Savage et al. |
| 6,245,065 B1 | 6/2001 | Panescu et al. |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,306,157 B1 | 10/2001 | Shchervinsky |
| 6,309,400 B2 | 10/2001 | Beaupre |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,350,269 B1 | 2/2002 | Shipp et al. |
| 6,352,532 B1 | 3/2002 | Kramer et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,109 B1 | 5/2002 | Davison et al. |
| 6,388,657 B1 | 5/2002 | Natoli |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,733 B1 | 6/2002 | Fogarty et al. |
| 6,416,486 B1 | 7/2002 | Wampler |
| 6,423,073 B2 | 7/2002 | Bowman |
| 6,423,082 B1 | 7/2002 | Houser et al. |
| 6,428,539 B1 | 8/2002 | Baxter et al. |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,500,312 B2 | 12/2002 | Wedekamp |
| 6,506,208 B2 | 1/2003 | Hunt et al. |
| 6,511,478 B1 | 1/2003 | Burnside et al. |
| 6,511,493 B1 | 1/2003 | Moutafis et al. |
| 6,514,267 B2 | 2/2003 | Jewett |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,558,376 B2 | 5/2003 | Bishop |
| 6,561,983 B2 | 5/2003 | Cronin et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| D477,408 S | 7/2003 | Bromley |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,607,540 B1 | 8/2003 | Shipp |
| 6,610,059 B1 | 8/2003 | West, Jr. |
| 6,616,450 B2 | 9/2003 | Mossle et al. |
| 6,619,529 B2 | 9/2003 | Green et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,644,532 B2 | 11/2003 | Green et al. |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,676,660 B2 | 1/2004 | Wampler et al. |
| 6,678,621 B2 | 1/2004 | Stulen et al. |
| 6,679,875 B2 | 1/2004 | Honda et al. |
| 6,679,899 B2 | 1/2004 | Wiener et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,716,215 B1 | 4/2004 | David et al. |
| 6,719,692 B2 | 4/2004 | Kleffner et al. |
| 6,719,776 B2 | 4/2004 | Baxter et al. |
| 6,723,091 B2 | 4/2004 | Goble et al. |
| D490,059 S | 5/2004 | Conway et al. |
| 6,731,047 B2 | 5/2004 | Kauf et al. |
| 6,733,506 B1 | 5/2004 | McDevitt et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,770,072 B1 | 8/2004 | Truckai et al. |

(56) References Cited

U.S. PATENT DOCUMENTS

| | | |
|---|---|---|
| 6,773,409 B2 | 8/2004 | Truckai et al. |
| 6,773,443 B2 | 8/2004 | Truwit et al. |
| 6,773,444 B2 | 8/2004 | Messerly |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,790,173 B2 | 9/2004 | Saadat et al. |
| 6,790,216 B1 | 9/2004 | Ishikawa |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,827,712 B2 | 12/2004 | Tovey et al. |
| 6,828,712 B2 | 12/2004 | Battaglin et al. |
| 6,835,082 B2 | 12/2004 | Gonnering |
| 6,849,073 B2 | 2/2005 | Hoey et al. |
| 6,860,878 B2 | 3/2005 | Brock |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Ratcliff et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,899,685 B2 | 5/2005 | Kermode et al. |
| 6,905,497 B2 | 6/2005 | Truckai et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,929,602 B2 | 8/2005 | Hirakui et al. |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,994,708 B2 | 2/2006 | Manzo |
| 7,001,335 B2 | 2/2006 | Adachi et al. |
| 7,011,657 B2 | 3/2006 | Truckai et al. |
| 7,014,638 B2 | 3/2006 | Michelson |
| 7,033,357 B2 | 4/2006 | Baxter et al. |
| 7,037,306 B2 | 5/2006 | Podany |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,066,893 B2 | 6/2006 | Hibner et al. |
| 7,066,895 B2 | 6/2006 | Podany |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,101,371 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,144,403 B2 | 12/2006 | Booth |
| 7,153,315 B2 | 12/2006 | Miller |
| D536,093 S | 1/2007 | Nakajima et al. |
| 7,156,189 B1 | 1/2007 | Bar-Cohen et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| D541,418 S | 4/2007 | Schechter et al. |
| 7,204,820 B2 | 4/2007 | Akahoshi |
| 7,207,997 B2 | 4/2007 | Shipp et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,229,455 B2 | 6/2007 | Sakurai et al. |
| 7,235,071 B2 | 6/2007 | Gonnering |
| 7,244,262 B2 | 7/2007 | Wiener et al. |
| 7,258,688 B1 | 8/2007 | Shah et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupré |
| 7,300,431 B2 | 11/2007 | Dubrovsky |
| 7,300,435 B2 | 11/2007 | Wham et al. |
| 7,300,446 B2 | 11/2007 | Beaupre |
| 7,303,531 B2 | 12/2007 | Lee et al. |
| 7,303,557 B2 | 12/2007 | Wham et al. |
| 7,306,597 B2 | 12/2007 | Manzo |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,326,236 B2 | 2/2008 | Andreas et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,364,577 B2 | 4/2008 | Wham et al. |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,390,317 B2 | 6/2008 | Taylor et al. |
| 7,404,508 B2 | 7/2008 | Smith et al. |
| 7,408,288 B2 | 8/2008 | Hara |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |

(56) References Cited

U.S. PATENT DOCUMENTS

| | | |
|---|---|---|
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,441,684 B2 | 10/2008 | Shelton, IV et al. |
| 7,455,208 B2 | 11/2008 | Wales et al. |
| 7,462,181 B2 | 12/2008 | Kraft et al. |
| 7,464,846 B2 | 12/2008 | Shelton, IV et al. |
| 7,472,815 B2 | 1/2009 | Shelton, IV et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,494,468 B2 | 2/2009 | Rabiner et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,540,871 B2 | 6/2009 | Gonnering |
| 7,549,564 B2 | 6/2009 | Boudreaux |
| 7,559,450 B2 | 7/2009 | Wales et al. |
| 7,567,012 B2 | 7/2009 | Namikawa |
| 7,572,266 B2 | 8/2009 | Young et al. |
| 7,578,820 B2 | 8/2009 | Moore et al. |
| 7,582,084 B2 | 9/2009 | Swanson et al. |
| 7,582,095 B2 | 9/2009 | Shipp et al. |
| 7,585,181 B2 | 9/2009 | Olsen |
| 7,588,176 B2 | 9/2009 | Timm et al. |
| 7,601,119 B2 | 10/2009 | Shahinian |
| 7,621,930 B2 | 11/2009 | Houser |
| 7,641,653 B2 | 1/2010 | Dalla et al. |
| 7,654,431 B2 | 2/2010 | Hueil et al. |
| 7,659,833 B2 | 2/2010 | Warner et al. |
| 7,665,647 B2 | 2/2010 | Shelton, IV et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,098 B2 | 4/2010 | Wallace et al. |
| 7,699,846 B2 | 4/2010 | Ryan |
| 7,713,202 B2 | 5/2010 | Boukhny et al. |
| 7,714,481 B2 | 5/2010 | Sakai |
| 7,717,312 B2 | 5/2010 | Beetel |
| 7,717,915 B2 | 5/2010 | Miyazawa |
| D618,797 S | 6/2010 | Price et al. |
| 7,726,537 B2 | 6/2010 | Olson et al. |
| 7,727,177 B2 | 6/2010 | Bayat |
| 7,738,969 B2 | 6/2010 | Bleich |
| 7,740,594 B2 | 6/2010 | Hibner |
| 7,751,115 B2 | 7/2010 | Song |
| D621,503 S | 8/2010 | Otten et al. |
| 7,766,210 B2 | 8/2010 | Shelton, IV et al. |
| 7,766,693 B2 | 8/2010 | Sartor et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,784,662 B2 | 8/2010 | Wales et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,819,819 B2 | 10/2010 | Quick et al. |
| D627,066 S | 11/2010 | Romero |
| 7,824,401 B2 | 11/2010 | Manzo et al. |
| 7,832,611 B2 | 11/2010 | Boyden et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,892,606 B2 | 2/2011 | Thies et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,824 B2 | 3/2011 | Masuda et al. |
| 7,922,061 B2 | 4/2011 | Shelton, IV et al. |
| 7,922,651 B2 | 4/2011 | Yamada et al. |
| D637,288 S | 5/2011 | Houghton |
| D638,540 S | 5/2011 | Ijiri et al. |
| 7,936,203 B2 | 5/2011 | Zimlich |
| 7,951,095 B2 | 5/2011 | Makin et al. |
| 7,951,165 B2 | 5/2011 | Golden et al. |
| 7,959,050 B2 | 6/2011 | Smith et al. |
| 7,959,626 B2 | 6/2011 | Hong et al. |
| 7,972,329 B2 | 7/2011 | Refior et al. |
| 7,976,544 B2 | 7/2011 | McClurken et al. |
| 7,981,050 B2 | 7/2011 | Ritchart et al. |
| 7,998,157 B2 | 8/2011 | Culp et al. |
| 8,038,693 B2 | 10/2011 | Allen |
| 8,057,498 B2 | 11/2011 | Robertson |
| 8,058,771 B2 | 11/2011 | Giordano et al. |
| 8,061,014 B2 | 11/2011 | Smith et al. |
| 8,070,711 B2 | 12/2011 | Bassinger et al. |
| 8,070,762 B2 | 12/2011 | Escudero et al. |
| 8,075,558 B2 | 12/2011 | Truckai et al. |
| 8,089,197 B2 | 1/2012 | Rinner et al. |
| 8,097,012 B2 | 1/2012 | Kagarise |
| 8,105,323 B2 | 1/2012 | Buysse et al. |
| 8,142,461 B2 | 3/2012 | Houser et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,877 B2 | 5/2012 | Klimovitch et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,502 B2 | 6/2012 | Smith et al. |
| 8,210,411 B2 | 7/2012 | Yates et al. |
| 8,226,675 B2 | 7/2012 | Houser et al. |
| 8,235,917 B2 | 8/2012 | Joseph et al. |
| 8,236,019 B2 | 8/2012 | Houser |
| 8,236,020 B2 | 8/2012 | Smith et al. |
| 8,241,271 B2 | 8/2012 | Millman et al. |
| 8,246,575 B2 | 8/2012 | Viola |
| 8,246,615 B2 | 8/2012 | Behnke |

(56) References Cited

U.S. PATENT DOCUMENTS

| | | |
|---|---|---|
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,273,087 B2 | 9/2012 | Kimura et al. |
| D669,992 S | 10/2012 | Schafer et al. |
| D669,993 S | 10/2012 | Merchant et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,888 B2 | 10/2012 | Whitman |
| 8,298,223 B2 | 10/2012 | Wham et al. |
| 8,298,225 B2 | 10/2012 | Gilbert |
| 8,303,576 B2 | 11/2012 | Brock |
| 8,303,580 B2 | 11/2012 | Wham et al. |
| 8,319,400 B2 | 11/2012 | Houser et al. |
| 8,323,302 B2 | 12/2012 | Robertson et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,344,596 B2 | 1/2013 | Nield et al. |
| 8,357,103 B2 | 1/2013 | Mark et al. |
| 8,372,101 B2 | 2/2013 | Smith et al. |
| 8,374,670 B2 | 2/2013 | Selkee |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,418,349 B2 | 4/2013 | Smith et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,664 B2 | 5/2013 | Balanev et al. |
| 8,479,969 B2 | 7/2013 | Shelton, IV |
| 8,480,703 B2 | 7/2013 | Nicholas et al. |
| 8,486,057 B2 | 7/2013 | Behnke, II |
| D687,549 S | 8/2013 | Johnson et al. |
| 8,506,555 B2 | 8/2013 | Morales |
| 8,509,318 B2 | 8/2013 | Tailliet |
| 8,512,359 B2 | 8/2013 | Whitman et al. |
| 8,535,340 B2 | 9/2013 | Allen |
| 8,535,341 B2 | 9/2013 | Allen |
| 8,568,400 B2 | 10/2013 | Gilbert |
| 8,573,461 B2 | 11/2013 | Shelton, IV et al. |
| 8,573,465 B2 | 11/2013 | Shelton, IV |
| 8,591,506 B2 | 11/2013 | Wham et al. |
| D695,407 S | 12/2013 | Price et al. |
| D696,631 S | 12/2013 | Price et al. |
| 8,602,031 B2 | 12/2013 | Reis et al. |
| 8,602,288 B2 | 12/2013 | Shelton, IV et al. |
| 8,608,745 B2 | 12/2013 | Guzman et al. |
| 8,616,431 B2 | 12/2013 | Timm et al. |
| 8,659,208 B1 | 2/2014 | Rose et al. |
| 8,690,582 B2 | 4/2014 | Rohrbach et al. |
| 8,696,366 B2 | 4/2014 | Chen et al. |
| 8,704,425 B2 | 4/2014 | Giordano et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,764,735 B2 | 7/2014 | Coe et al. |
| 8,773,001 B2 | 7/2014 | Wiener et al. |
| 8,779,648 B2 | 7/2014 | Giordano et al. |
| 8,827,992 B2 | 9/2014 | Koss et al. |
| 8,845,537 B2 | 9/2014 | Tanaka et al. |
| 8,888,776 B2 | 11/2014 | Dietz et al. |
| 8,968,355 B2 | 3/2015 | Malkowski et al. |
| 8,974,477 B2 | 3/2015 | Yamada |
| 8,986,287 B2 | 3/2015 | Park et al. |
| 8,989,903 B2 | 3/2015 | Weir et al. |
| 9,050,124 B2 | 6/2015 | Houser |
| 9,066,747 B2 | 6/2015 | Robertson |
| 9,095,367 B2 | 8/2015 | Olson et al. |
| 9,107,689 B2 | 8/2015 | Robertson et al. |
| 2001/0025173 A1 | 9/2001 | Ritchie et al. |
| 2001/0025183 A1 | 9/2001 | Shahidi et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0156466 A1 | 10/2002 | Sakurai et al. |
| 2002/0156493 A1 | 10/2002 | Houser et al. |
| 2003/0014087 A1 | 1/2003 | Fang et al. |
| 2003/0036705 A1 | 2/2003 | Hare et al. |
| 2003/0050572 A1 | 3/2003 | Brautigam et al. |
| 2003/0055443 A1 | 3/2003 | Spotnitz |
| 2003/0114851 A1 | 6/2003 | Truckai et al. |
| 2003/0144680 A1 | 7/2003 | Kellogg et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0092921 A1 | 5/2004 | Kadziauskas et al. |
| 2004/0092992 A1 | 5/2004 | Adams et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0132383 A1 | 7/2004 | Langford et al. |
| 2004/0147934 A1 | 7/2004 | Kiester |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0199193 A1 | 10/2004 | Hayashi et al. |
| 2004/0204728 A1 | 10/2004 | Haefner |
| 2004/0243147 A1 | 12/2004 | Lipow |
| 2004/0260300 A1 | 12/2004 | Gorensek et al. |
| 2005/0021018 A1 | 1/2005 | Anderson et al. |
| 2005/0021065 A1 | 1/2005 | Yamada et al. |
| 2005/0033337 A1 | 2/2005 | Muir et al. |
| 2005/0049546 A1 | 3/2005 | Messerly et al. |
| 2005/0065529 A1* | 3/2005 | Liu et al. .............. 606/79 |
| 2005/0070800 A1 | 3/2005 | Takahashi |
| 2005/0096683 A1 | 5/2005 | Ellins et al. |
| 2005/0099824 A1 | 5/2005 | Dowling et al. |
| 2005/0103819 A1 | 5/2005 | Racenet et al. |
| 2005/0143769 A1 | 6/2005 | White et al. |
| 2005/0149108 A1 | 7/2005 | Cox |
| 2005/0165345 A1 | 7/2005 | Laufer et al. |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0209620 A1 | 9/2005 | Du et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261581 A1 | 11/2005 | Hughes et al. |
| 2005/0261588 A1 | 11/2005 | Makin et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0066181 A1 | 3/2006 | Bromfield et al. |
| 2006/0074442 A1 | 4/2006 | Noriega et al. |

(56) References Cited

U.S. PATENT DOCUMENTS

| | | |
|---|---|---|
| 2006/0079878 A1 | 4/2006 | Houser |
| 2006/0079879 A1 | 4/2006 | Faller et al. |
| 2006/0084963 A1 | 4/2006 | Messerly |
| 2006/0095046 A1 | 5/2006 | Trieu et al. |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0235306 A1 | 10/2006 | Cotter et al. |
| 2006/0247558 A1 | 11/2006 | Yamada |
| 2006/0253050 A1 | 11/2006 | Yoshimine et al. |
| 2006/0264809 A1 | 11/2006 | Hansmann et al. |
| 2006/0271030 A1 | 11/2006 | Francis et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0056596 A1 | 3/2007 | Fanney et al. |
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0074584 A1 | 4/2007 | Talarico et al. |
| 2007/0106317 A1 | 5/2007 | Shelton, IV et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0162050 A1 | 7/2007 | Sartor |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175949 A1 | 8/2007 | Shelton, IV et al. |
| 2007/0185380 A1 | 8/2007 | Kucklick |
| 2007/0191712 A1 | 8/2007 | Messerly et al. |
| 2007/0219481 A1 | 9/2007 | Babaev |
| 2007/0239028 A1 | 10/2007 | Houser et al. |
| 2007/0239101 A1 | 10/2007 | Kellogg |
| 2007/0249941 A1 | 10/2007 | Salehi et al. |
| 2007/0260234 A1 | 11/2007 | McCullagh et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2008/0009848 A1 | 1/2008 | Paraschiv et al. |
| 2008/0013809 A1 | 1/2008 | Zhu et al. |
| 2008/0051812 A1 | 2/2008 | Schmitz et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0114364 A1 | 5/2008 | Goldin et al. |
| 2008/0125768 A1 | 5/2008 | Tahara et al. |
| 2008/0140158 A1 | 6/2008 | Hamel et al. |
| 2008/0147092 A1 | 6/2008 | Rogge et al. |
| 2008/0171938 A1 | 7/2008 | Masuda et al. |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0234710 A1 | 9/2008 | Neurohr et al. |
| 2008/0243106 A1 | 10/2008 | Coe et al. |
| 2008/0243162 A1 | 10/2008 | Shibata et al. |
| 2008/0245371 A1 | 10/2008 | Gruber |
| 2008/0249553 A1 | 10/2008 | Gruber et al. |
| 2008/0255423 A1 | 10/2008 | Kondo et al. |
| 2008/0262490 A1 | 10/2008 | Williams |
| 2008/0281200 A1 | 11/2008 | Voic et al. |
| 2008/0281315 A1 | 11/2008 | Gines |
| 2008/0281322 A1 | 11/2008 | Sherman et al. |
| 2008/0287948 A1 | 11/2008 | Newton et al. |
| 2009/0023985 A1 | 1/2009 | Ewers |
| 2009/0030311 A1 | 1/2009 | Stulen et al. |
| 2009/0030437 A1 | 1/2009 | Houser et al. |
| 2009/0030438 A1 | 1/2009 | Stulen |
| 2009/0030439 A1 | 1/2009 | Stulen |
| 2009/0036912 A1 | 2/2009 | Wiener et al. |
| 2009/0036913 A1 | 2/2009 | Wiener et al. |
| 2009/0036914 A1 | 2/2009 | Houser |
| 2009/0048537 A1 | 2/2009 | Lydon et al. |
| 2009/0054886 A1 | 2/2009 | Yachi et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0105750 A1 | 4/2009 | Price et al. |
| 2009/0112229 A1 | 4/2009 | Omori et al. |
| 2009/0118751 A1 | 5/2009 | Wiener et al. |
| 2009/0118802 A1 | 5/2009 | Mioduski et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0143806 A1 | 6/2009 | Witt et al. |
| 2009/0149801 A1 | 6/2009 | Crandall et al. |
| 2009/0207923 A1 | 8/2009 | Dress |
| 2009/0216157 A1 | 8/2009 | Yamada |
| 2009/0223033 A1 | 9/2009 | Houser |
| 2009/0254077 A1 | 10/2009 | Craig |
| 2009/0254080 A1 | 10/2009 | Honda |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270899 A1 | 10/2009 | Carusillo et al. |
| 2009/0275940 A1 | 11/2009 | Malackowski et al. |
| 2009/0318945 A1 | 12/2009 | Yoshimine et al. |
| 2009/0327715 A1 | 12/2009 | Smith et al. |
| 2010/0004508 A1 | 1/2010 | Naito et al. |
| 2010/0004668 A1 | 1/2010 | Smith et al. |
| 2010/0004669 A1 | 1/2010 | Smith et al. |
| 2010/0016785 A1 | 1/2010 | Takuma |
| 2010/0016852 A1 | 1/2010 | Manzo et al. |
| 2010/0022825 A1 | 1/2010 | Yoshie |
| 2010/0030233 A1 | 2/2010 | Whitman et al. |
| 2010/0030248 A1 | 2/2010 | Palmer et al. |
| 2010/0036370 A1 | 2/2010 | Mirel et al. |
| 2010/0042077 A1 | 2/2010 | Okada |
| 2010/0049180 A1 | 2/2010 | Wells et al. |
| 2010/0063525 A1 | 3/2010 | Beaupre et al. |
| 2010/0063528 A1 | 3/2010 | Beaupré |
| 2010/0069940 A1 | 3/2010 | Miller et al. |
| 2010/0158307 A1 | 6/2010 | Kubota et al. |
| 2010/0187283 A1 | 7/2010 | Crainich et al. |
| 2010/0193567 A1 | 8/2010 | Scheib et al. |
| 2010/0222714 A1 | 9/2010 | Muir et al. |
| 2010/0228264 A1 | 9/2010 | Robinson et al. |
| 2010/0234906 A1 | 9/2010 | Koh |
| 2010/0262134 A1 | 10/2010 | Jensen et al. |
| 2010/0268211 A1 | 10/2010 | Manwaring et al. |
| 2010/0274160 A1 | 10/2010 | Yachi et al. |
| 2010/0280407 A1 | 11/2010 | Polster |
| 2010/0292691 A1 | 11/2010 | Brogna |
| 2010/0298743 A1 | 11/2010 | Nield et al. |
| 2010/0298851 A1 | 11/2010 | Nield |
| 2010/0331742 A1 | 12/2010 | Masuda |
| 2010/0331870 A1 | 12/2010 | Wan et al. |
| 2011/0004233 A1 | 1/2011 | Muir et al. |
| 2011/0009850 A1 | 1/2011 | Main et al. |
| 2011/0015627 A1 | 1/2011 | DiNardo et al. |
| 2011/0015631 A1 | 1/2011 | Wiener et al. |
| 2011/0015660 A1 | 1/2011 | Wiener et al. |
| 2011/0077648 A1 | 3/2011 | Lee et al. |
| 2011/0082486 A1 | 4/2011 | Messerly et al. |

(56) References Cited

U.S. PATENT DOCUMENTS

| | | |
|---|---|---|
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 | 4/2011 | Boudreaux et al. |
| 2011/0087256 A1 | 4/2011 | Wiener et al. |
| 2011/0112526 A1 | 5/2011 | Fritz et al. |
| 2011/0125151 A1 | 5/2011 | Strauss et al. |
| 2011/0125174 A1 | 5/2011 | Babaev |
| 2011/0144806 A1 | 6/2011 | Sandhu et al. |
| 2011/0196286 A1 | 8/2011 | Robertson et al. |
| 2011/0196398 A1 | 8/2011 | Robertson et al. |
| 2011/0196399 A1 | 8/2011 | Robertson et al. |
| 2011/0196400 A1 | 8/2011 | Robertson et al. |
| 2011/0196401 A1 | 8/2011 | Robertson et al. |
| 2011/0196402 A1 | 8/2011 | Robertson et al. |
| 2011/0196403 A1 | 8/2011 | Robertson et al. |
| 2011/0196404 A1 | 8/2011 | Dietz et al. |
| 2011/0196405 A1 | 8/2011 | Dietz |
| 2011/0224689 A1 | 9/2011 | Larkin et al. |
| 2011/0238065 A1 | 9/2011 | Hunt et al. |
| 2011/0257650 A1 | 10/2011 | Deville et al. |
| 2011/0270126 A1 | 11/2011 | Gunday et al. |
| 2011/0288452 A1 | 11/2011 | Houser et al. |
| 2011/0290853 A1 | 12/2011 | Shelton, IV et al. |
| 2011/0290856 A1 | 12/2011 | Shelton, IV et al. |
| 2012/0004655 A1 | 1/2012 | Kim et al. |
| 2012/0022525 A1 | 1/2012 | Dietz et al. |
| 2012/0022530 A1 | 1/2012 | Woodruff et al. |
| 2012/0022583 A1 | 1/2012 | Sugalski et al. |
| 2012/0029546 A1 | 2/2012 | Robertson |
| 2012/0059289 A1 | 3/2012 | Nield et al. |
| 2012/0065628 A1 | 3/2012 | Naito |
| 2012/0071863 A1 | 3/2012 | Lee et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078278 A1 | 3/2012 | Bales, Jr. et al. |
| 2012/0080332 A1 | 4/2012 | Shelton, IV et al. |
| 2012/0083783 A1 | 4/2012 | Davison et al. |
| 2012/0083784 A1 | 4/2012 | Davison et al. |
| 2012/0101495 A1 | 4/2012 | Young et al. |
| 2012/0109159 A1 | 5/2012 | Jordan et al. |
| 2012/0116379 A1 | 5/2012 | Yates et al. |
| 2012/0116391 A1 | 5/2012 | Houser et al. |
| 2012/0116394 A1 | 5/2012 | Timm et al. |
| 2012/0116395 A1 | 5/2012 | Madan et al. |
| 2012/0130256 A1 | 5/2012 | Buysse et al. |
| 2012/0130365 A1 | 5/2012 | McLawhorn |
| 2012/0136354 A1 | 5/2012 | Rupp |
| 2012/0138660 A1 | 6/2012 | Shelton, IV |
| 2012/0143211 A1 | 6/2012 | Kishi |
| 2012/0150170 A1 | 6/2012 | Buysse et al. |
| 2012/0165816 A1 | 6/2012 | Kersten et al. |
| 2012/0172873 A1 | 7/2012 | Artale et al. |
| 2012/0172904 A1 | 7/2012 | Muir et al. |
| 2012/0177005 A1 | 7/2012 | Liang et al. |
| 2012/0184946 A1 | 7/2012 | Price et al. |
| 2012/0199630 A1 | 8/2012 | Shelton, IV |
| 2012/0199632 A1 | 8/2012 | Spivey et al. |
| 2012/0203143 A1 | 8/2012 | Sanai et al. |
| 2012/0203247 A1 | 8/2012 | Shelton, IV et al. |
| 2012/0203257 A1 | 8/2012 | Stulen et al. |
| 2012/0209289 A1 | 8/2012 | Duque et al. |
| 2012/0209303 A1 | 8/2012 | Frankhouser et al. |
| 2012/0210223 A1 | 8/2012 | Eppolito |
| 2012/0215220 A1 | 8/2012 | Manzo et al. |
| 2012/0245582 A1 | 9/2012 | Kimball et al. |
| 2012/0253370 A1 | 10/2012 | Ross et al. |
| 2012/0259353 A1 | 10/2012 | Houser et al. |
| 2012/0265196 A1 | 10/2012 | Turner et al. |
| 2012/0289984 A1 | 11/2012 | Houser et al. |
| 2012/0310262 A1 | 12/2012 | Messerly et al. |
| 2012/0310263 A1 | 12/2012 | Messerly et al. |
| 2012/0310264 A1 | 12/2012 | Messerly et al. |
| 2012/0323265 A1 | 12/2012 | Stulen |
| 2012/0330307 A1 | 12/2012 | Ladtkow et al. |
| 2013/0012957 A1 | 1/2013 | Shelton, IV et al. |
| 2013/0030433 A1 | 1/2013 | Heard |
| 2013/0035680 A1 | 2/2013 | Ben-Haim et al. |
| 2013/0053840 A1 | 2/2013 | Krapohl et al. |
| 2013/0072856 A1 | 3/2013 | Frankhouser et al. |
| 2013/0072857 A1 | 3/2013 | Frankhouser et al. |
| 2013/0079762 A1 | 3/2013 | Twomey et al. |
| 2013/0103023 A1 | 4/2013 | Monson et al. |
| 2013/0103024 A1 | 4/2013 | Monson et al. |
| 2013/0110145 A1 | 5/2013 | Weitzman |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0123822 A1 | 5/2013 | Wellman et al. |
| 2013/0131660 A1 | 5/2013 | Monson et al. |
| 2013/0165929 A1 | 6/2013 | Muir et al. |
| 2013/0211397 A1 | 8/2013 | Parihar et al. |
| 2013/0217967 A1 | 8/2013 | Mohr et al. |
| 2013/0226207 A1 | 8/2013 | Stulen et al. |
| 2013/0226208 A1 | 8/2013 | Wiener et al. |
| 2013/0245659 A1 | 9/2013 | Robertson et al. |
| 2013/0267975 A1 | 10/2013 | Timm et al. |
| 2013/0274734 A1 | 10/2013 | Maass et al. |
| 2013/0282003 A1 | 10/2013 | Messerly et al. |
| 2013/0282038 A1 | 10/2013 | Dannaher et al. |
| 2013/0282039 A1 | 10/2013 | Wiener et al. |
| 2013/0285758 A1 | 10/2013 | Aldridge et al. |
| 2013/0289591 A1 | 10/2013 | Boudreaux et al. |
| 2013/0296908 A1 | 11/2013 | Schulte et al. |
| 2013/0338661 A1 | 12/2013 | Behnke, II |
| 2013/0345689 A1 | 12/2013 | Ruddenklau et al. |
| 2014/0005640 A1 | 1/2014 | Shelton, IV et al. |
| 2014/0005653 A1 | 1/2014 | Shelton, IV et al. |
| 2014/0005654 A1 | 1/2014 | Batross et al. |
| 2014/0005656 A1 | 1/2014 | Mucilli et al. |
| 2014/0005661 A1 | 1/2014 | Shelton, IV et al. |
| 2014/0005662 A1 | 1/2014 | Shelton, IV et al. |
| 2014/0005667 A1 | 1/2014 | Stulen et al. |
| 2014/0005668 A1 | 1/2014 | Rhee et al. |
| 2014/0005676 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005682 A1 | 1/2014 | Worrell et al. |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005704 A1 | 1/2014 | Vakharia et al. |
| 2014/0005705 A1 | 1/2014 | Weir et al. |
| 2014/0005708 A1 | 1/2014 | Shelton, IV et al. |
| 2014/0005718 A1 | 1/2014 | Shelton, IV et al. |
| 2014/0012299 A1 | 1/2014 | Stoddard et al. |
| 2014/0066962 A1 | 3/2014 | Robertson et al. |
| 2014/0087569 A1 | 3/2014 | Lee |
| 2014/0107538 A1 | 4/2014 | Wiener et al. |
| 2014/0114327 A1 | 4/2014 | Boudreaux et al. |
| 2014/0135804 A1 | 5/2014 | Weisenburgh, II et al. |
| 2014/0155921 A1 | 6/2014 | Price et al. |
| 2014/0180280 A1 | 6/2014 | Sigmon, Jr. |
| 2014/0243864 A1 | 8/2014 | Voegele et al. |
| 2014/0276738 A1 | 9/2014 | Price et al. |
| 2014/0276970 A1 | 9/2014 | Messerly et al. |
| 2014/0336686 A1 | 11/2014 | Houser et al. |
| 2015/0045819 A1 | 2/2015 | Houser et al. |
| 2015/0066067 A1 | 3/2015 | Stulen |
| 2015/0073460 A1 | 3/2015 | Stulen |
| 2015/0112335 A1 | 4/2015 | Boudreaux et al. |
| 2015/0119914 A1 | 4/2015 | Neurohr et al. |
| 2015/0119915 A1 | 4/2015 | Neurohr et al. |
| 2015/0119916 A1 | 4/2015 | Dietz et al. |
| 2015/0123348 A1 | 5/2015 | Robertson et al. |
| 2015/0157355 A1 | 6/2015 | Price et al. |
| 2015/0157356 A1 | 6/2015 | Gee |
| 2015/0164533 A1 | 6/2015 | Felder et al. |
| 2015/0164534 A1 | 6/2015 | Felder et al. |

(56) References Cited

U.S. PATENT DOCUMENTS

| | | | |
|---|---|---|---|
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0182251 A1 | 7/2015 | Messerly et al. |
| 2015/0182276 A1 | 7/2015 | Wiener et al. |
| 2015/0182277 A1 | 7/2015 | Wiener et al. |
| 2015/0196318 A1 | 7/2015 | Messerly et al. |

FOREIGN PATENT DOCUMENTS

| | | | |
|---|---|---|---|
| CN | 1640365 A | 7/2005 |
| CN | 1694649 A | 11/2005 |
| CN | 1922563 A | 2/2007 |
| CN | 1951333 A | 4/2007 |
| CN | 101040799 A | 9/2007 |
| CN | 101467917 A | 1/2009 |
| DE | 3904558 A1 | 8/1990 |
| DE | 9210327 U1 | 11/1992 |
| DE | 4323585 A1 | 1/1995 |
| DE | 19608716 C1 | 4/1997 |
| DE | 20021619 U1 | 3/2001 |
| DE | 10042606 A1 | 8/2001 |
| EP | 0136855 B1 | 9/1984 |
| EP | 0171967 A2 | 2/1986 |
| EP | 1839599 A1 | 10/1987 |
| EP | 0336742 A2 | 4/1989 |
| EP | 0342448 A1 | 11/1989 |
| EP | 0424685 B1 | 5/1991 |
| EP | 0443256 A1 | 8/1991 |
| EP | 0456470 A1 | 11/1991 |
| EP | 0598976 A2 | 1/1994 |
| EP | 0677275 A2 | 3/1995 |
| EP | 0482195 B1 | 1/1996 |
| EP | 0695535 A1 | 2/1996 |
| EP | 0741996 A2 | 11/1996 |
| EP | 0612570 B1 | 6/1997 |
| EP | 1108394 A2 | 6/2001 |
| EP | 0908148 B1 | 1/2002 |
| EP | 1229515 A2 | 8/2002 |
| EP | 1285634 A1 | 2/2003 |
| EP | 0908155 B1 | 6/2003 |
| EP | 0705570 B1 | 4/2004 |
| EP | 0765637 B1 | 7/2004 |
| EP | 0870473 B1 | 9/2005 |
| EP | 0624346 B1 | 11/2005 |
| EP | 1594209 A1 | 11/2005 |
| EP | 1199044 B1 | 12/2005 |
| EP | 1609428 A1 | 12/2005 |
| EP | 1199043 B1 | 3/2006 |
| EP | 1433425 B1 | 6/2006 |
| EP | 1256323 B1 | 9/2006 |
| EP | 1698289 A2 | 9/2006 |
| EP | 1704824 A1 | 9/2006 |
| EP | 1749479 A1 | 2/2007 |
| EP | 1815950 A1 | 8/2007 |
| EP | 1844720 A1 | 10/2007 |
| EP | 1862133 A1 | 12/2007 |
| EP | 1875875 A1 | 1/2008 |
| EP | 1199045 B1 | 6/2008 |
| EP | 1964530 A1 | 9/2008 |
| EP | 1972264 A1 | 9/2008 |
| EP | 1974771 A1 | 10/2008 |
| EP | 1435852 B1 | 12/2008 |
| EP | 1498082 B1 | 12/2008 |
| EP | 1707131 B1 | 12/2008 |
| EP | 1997438 A2 | 12/2008 |
| EP | 1477104 B1 | 1/2009 |
| EP | 2014218 A2 | 1/2009 |
| EP | 2042112 A2 | 4/2009 |
| EP | 1832259 B1 | 6/2009 |
| EP | 2074959 A1 | 7/2009 |
| EP | 2106758 A1 | 10/2009 |
| EP | 2111813 A1 | 10/2009 |
| EP | 2200145 A1 | 6/2010 |
| EP | 1214913 B1 | 7/2010 |
| EP | 2238938 A1 | 10/2010 |
| EP | 2298154 A2 | 3/2011 |
| EP | 1510178 B1 | 6/2011 |
| EP | 2305144 A1 | 6/2011 |
| EP | 2335630 A1 | 6/2011 |
| EP | 1502551 B1 | 7/2011 |
| EP | 2361562 A1 | 8/2011 |
| EP | 2365608 A2 | 9/2011 |
| EP | 2422721 A2 | 2/2012 |
| EP | 1927321 B1 | 4/2012 |
| EP | 2510891 A1 | 10/2012 |
| EP | 2316359 B1 | 3/2013 |
| EP | 1586275 B1 | 5/2013 |
| EP | 1616529 B1 | 9/2013 |
| EP | 2583633 B1 | 10/2014 |
| GB | 1482943 A | 8/1977 |
| GB | 2032221 A | 4/1980 |
| GB | 2379878 B | 11/2004 |
| GB | 2447767 B | 8/2011 |
| JP | S 50-100891 | 12/1973 |
| JP | S 5968513 | 10/1982 |
| JP | S 59141938 A | 8/1984 |
| JP | 62-221343 A | 9/1987 |
| JP | S 62227343 | 10/1987 |
| JP | 62-2292153 A | 12/1987 |
| JP | S 62292154 A | 12/1987 |
| JP | 63-109386 A | 5/1988 |
| JP | 63-315049 A | 12/1988 |
| JP | H 01-151452 A | 6/1989 |
| JP | H 01-198540 A | 8/1989 |
| JP | 02-71510 U | 5/1990 |
| JP | 2-286149 A | 11/1990 |
| JP | H 02-292193 A | 12/1990 |
| JP | H 03-37061 A | 2/1991 |
| JP | 04-25707 U | 2/1992 |
| JP | H 04-64351 A | 2/1992 |
| JP | 4-30508 U | 3/1992 |
| JP | H 04-150847 A | 5/1992 |
| JP | H 04-152942 A | 5/1992 |
| JP | 05-095955 A | 4/1993 |
| JP | H 05-115490 A | 5/1993 |
| JP | H 06-070938 A | 3/1994 |
| JP | 6-104503 A | 4/1994 |
| JP | 6-507081 A | 8/1994 |
| JP | H 06-217988 A | 8/1994 |
| JP | H 7-508910 A | 10/1995 |
| JP | 7-308323 A | 11/1995 |
| JP | 8-24266 A | 1/1996 |
| JP | 8-275951 A | 10/1996 |
| JP | H 08-299351 A | 11/1996 |
| JP | H 08-336545 A | 12/1996 |
| JP | H 09-503146 A | 3/1997 |
| JP | H 09-135553 A | 5/1997 |
| JP | H 09-140722 A | 6/1997 |
| JP | H 10-005237 A | 1/1998 |
| JP | 10-295700 A | 11/1998 |
| JP | H 11-501543 A | 2/1999 |
| JP | H 11-128238 | 5/1999 |
| JP | H 11-192235 A | 7/1999 |
| JP | 11-253451 A | 9/1999 |
| JP | H 11-318918 A | 11/1999 |
| JP | 2000-041991 A | 2/2000 |
| JP | 2000-070279 A | 3/2000 |
| JP | 2000-210299 A | 8/2000 |
| JP | 2000-287987 A | 10/2000 |
| JP | 2001-029353 A | 2/2001 |
| JP | 2001-502216 A | 2/2001 |
| JP | 2003612 A | 6/2001 |
| JP | 2001-309925 A | 11/2001 |
| JP | 2002-186901 A | 7/2002 |
| JP | 2002-204808 A | 7/2002 |
| JP | 2002-263579 A | 9/2002 |
| JP | 2002-301086 A | 10/2002 |
| JP | 2002-330977 A | 11/2002 |
| JP | 2002-542690 A | 12/2002 |
| JP | 2003-000612 A | 1/2003 |
| JP | 2003-010201 | 1/2003 |
| JP | 2003-510158 A | 3/2003 |

(56) References Cited

FOREIGN PATENT DOCUMENTS

| | | |
|---|---|---|
| JP | 2003-116870 A | 4/2003 |
| JP | 2003-126110 A | 5/2003 |
| JP | 2003-310627 | 5/2003 |
| JP | 2003-530921 A | 10/2003 |
| JP | 2003-339730 A | 12/2003 |
| JP | 2004-147701 A | 5/2004 |
| JP | 2005027026 A | 1/2005 |
| JP | 2005-040222 A | 2/2005 |
| JP | 2005-066316 A | 3/2005 |
| JP | 2005-074088 A | 3/2005 |
| JP | 2005-534451 A | 11/2005 |
| JP | 2006-6410 A | 1/2006 |
| JP | 2006-512149 A | 4/2006 |
| JP | 2006-16194 A | 5/2006 |
| JP | 2006-158525 A | 6/2006 |
| JP | 2006-218296 A | 8/2006 |
| JP | 2006217716 A | 8/2006 |
| JP | 2006-288431 A | 10/2006 |
| JP | 2007-050181 A | 3/2007 |
| JP | 2003-126104 A | 5/2007 |
| JP | 2007-229454 A | 9/2007 |
| JP | 2007-527747 A | 10/2007 |
| JP | 2008-508065 A | 3/2008 |
| JP | 2008-119250 A | 5/2008 |
| JP | 2008-521503 A | 6/2008 |
| JP | 2008-212679 A | 9/2008 |
| JP | 2008-536562 A | 9/2008 |
| JP | 2008-284374 | 11/2008 |
| JP | 2009-511206 A | 3/2009 |
| JP | 2009-517181 A | 4/2009 |
| JP | 4262923 B2 | 5/2009 |
| JP | 2009-523567 A | 6/2009 |
| JP | 2009-236177 | 10/2009 |
| JP | 2009-254819 A | 11/2009 |
| JP | 2010-000336 A | 1/2010 |
| JP | 2010-514923 A | 5/2010 |
| JP | 2010-534522 A | 11/2010 |
| JP | 2010-540186 A | 12/2010 |
| JP | 2011-505198 A | 2/2011 |
| JP | 2012-235658 A | 11/2012 |
| JP | 528761 B2 | 6/2013 |
| WO | WO 92/22259 A2 | 12/1992 |
| WO | WO 93/08757 A1 | 5/1993 |
| WO | WO 2013/062978 A2 | 5/1993 |
| WO | WO 93/14708 A1 | 8/1993 |
| WO | WO 93/16646 A1 | 9/1993 |
| WO | WO 93/20877 A1 | 10/1993 |
| WO | WO 93/21183 A1 | 9/1994 |
| WO | WO 94/24949 A1 | 11/1994 |
| WO | WO 95/09572 A1 | 4/1995 |
| WO | WO 96/30885 A1 | 10/1996 |
| WO | WO 96/39086 A1 | 12/1996 |
| WO | WO 98/16156 A1 | 4/1998 |
| WO | WO 98/26739 A1 | 6/1998 |
| WO | WO 98/35621 A1 | 8/1998 |
| WO | WO 98/37815 A1 | 9/1998 |
| WO | WO 99/20213 A1 | 4/1999 |
| WO | WO 99/52489 A1 | 10/1999 |
| WO | WO 00/64358 A2 | 11/2000 |
| WO | WO 00/74585 A2 | 12/2000 |
| WO | WO 01/54590 A1 | 8/2001 |
| WO | WO 01/67970 A1 | 9/2001 |
| WO | WO 01/95810 A2 | 12/2001 |
| WO | WO 02/24080 A2 | 3/2002 |
| WO | WO 02/38057 A1 | 5/2002 |
| WO | WO 02/062241 A1 | 8/2002 |
| WO | WO 03/082133 A1 | 10/2003 |
| WO | WO 2004/012615 A1 | 2/2004 |
| WO | WO 2004/026104 A2 | 4/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/037095 A2 | 5/2004 |
| WO | WO 2004/984226 A1 | 11/2004 |
| WO | WO 2004/112618 A2 | 12/2004 |
| WO | WO 2005/122917 A1 | 12/2005 |
| WO | WO 2006/012797 A1 | 2/2006 |
| WO | WO 2006/042210 A2 | 4/2006 |
| WO | WO 2006/058223 A2 | 6/2006 |
| WO | WO 2006/063199 A2 | 6/2006 |
| WO | WO 2006/083988 A1 | 8/2006 |
| WO | WO 2006/119139 A2 | 11/2006 |
| WO | WO 2006/119376 A2 | 11/2006 |
| WO | WO 2006/129465 A1 | 12/2006 |
| WO | WO 2007/008703 A2 | 1/2007 |
| WO | WO 2007/008710 A2 | 1/2007 |
| WO | WO 2007/040818 A1 | 4/2007 |
| WO | WO 2007/047380 A2 | 4/2007 |
| WO | WO 2007/047531 A2 | 4/2007 |
| WO | WO 2007/056590 A1 | 5/2007 |
| WO | WO 2007/087272 A2 | 8/2007 |
| WO | WO 2007/143665 A2 | 12/2007 |
| WO | WO 2008/016886 A2 | 2/2008 |
| WO | WO 2008/042021 A1 | 4/2008 |
| WO | WO 2008/049084 A2 | 4/2008 |
| WO | WO 2008/051764 A2 | 4/2008 |
| WO | WO 2008/089174 A2 | 7/2008 |
| WO | WO 2008/118709 A1 | 10/2008 |
| WO | WO 2008/130793 A1 | 10/2008 |
| WO | WO 2009/018067 A1 | 2/2009 |
| WO | WO 2009/018406 A2 | 2/2009 |
| WO | WO 2009/027065 A1 | 3/2009 |
| WO | WO 2009/046234 A2 | 4/2009 |
| WO | WO 2009/073402 A2 | 6/2009 |
| WO | WO 2009/120992 A2 | 10/2009 |
| WO | WO 2010/068783 A1 | 6/2010 |
| WO | WO 2011/008672 A2 | 1/2011 |
| WO | WO 2011/052938 A2 | 5/2011 |
| WO | WO 2011/100321 A2 | 8/2011 |
| WO | WO 2011/144911 A1 | 11/2011 |
| WO | WO 2012/061722 A2 | 5/2012 |
| WO | WO 2012/128362 A1 | 9/2012 |
| WO | WO 2012/135705 A1 | 10/2012 |
| WO | WO 2012/135721 A1 | 10/2012 |
| WO | WO 2013/018934 A1 | 2/2013 |

OTHER PUBLICATIONS

Australian Patent Examination Report No. 1, Application No. 2008231089, dated Sep. 7, 2012 (5 pages).
*Technology Overview*, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in Physical Properties of Tissue (1990).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al, "Thermal Imaging in Surgery," p. 19-3, in *Medical Infrared Imaging*, N. A. Diakides and J. D. Bronzino, Eds. (2008).
U.S. Appl. No. 29/404,676, filed Oct. 24, 2011.

(56) References Cited

OTHER PUBLICATIONS

U.S. Appl. No. 13/151,181, filed Jun. 2, 2011.
U.S. Appl. No. 13/369,561, filed Feb. 9, 2012.
U.S. Appl. No. 13/369,569, filed Feb. 9, 2012.
U.S. Appl. No. 13/369,578, filed Feb. 9, 2012.
U.S. Appl. No. 13/369,584, filed Feb. 9, 2012.
U.S. Appl. No. 13/369,588, filed Feb. 9, 2012.
U.S. Appl. No. 13/369,594, filed Feb. 9, 2012.
U.S. Appl. No. 13/369,601 filed Feb. 9, 2012.
U.S. Appl. No. 13/369,609, filed Feb. 9, 2012.
U.S. Appl. No. 13/369,629, filed Feb. 9, 2012.
U.S. Appl. No. 13/369,666, filed Feb. 9, 2012.
U.S. Appl. No. 13/545,292, filed Jul. 10, 2012.
U.S. Appl. No. 13/584,020, filed Aug. 13, 2012.
U.S. Appl. No. 13/584,445, filed Aug. 13, 2012.
European Examination Report for 08732446.3, dated Oct. 30, 2013 (6 pages).
Sullivan, "Cost-Constrainted Selection of Strand Diameter and Number in a Litz-Wire Transformer Winding", IEEE Transactions on Power Electronics, vol. 16, No. 2, Mar. 2001, pp. 281-288.
Sullivan, "Optimal Choice for Number of Strands in a Litz-Wire Transformer Winding", IEEE Transactions on Power Electronics, vol. 14, No. 2, Mar. 1999, pp. 283-291.
Graff, K.F., "Elastic Wave Propagation in a Curved Sonic Transmission Line," IEEE Transactions on Sonics and Ultrasonics, SU-(17), 1-6 (1970).
Makarov, S.N., Ochmann, M., Desinger, K., "The longitudinal vibration response of a curved fiber used for laser ultrasound surgical therapy", Journal of the Acoustical Society of America 102, 1191-1199 (1997).
Morley, L.S.D., "Elastic Waves in a Naturally Curved Rod", Quarterly Journal of Mechanics and Applied Mathematics, 14:155-172 (1961).
Walsh, S.J., White, R.G., "Vibrational Power Transmission in Curved Beams," Journal of Sound and Vibration, 233(3), 455-488 (2000).
http://www.apicalinstr.com/generators.htm.
http://www.dotmed.com/listing/electrosurical-unit/ethicon/ultracision-g110-/1466724.
http://www.ethicon.com/gb-en/healthcare-professionals/products/energy-devices/capital//ge . . . .
http://www.4-traders.com/JOHNSON-JOHNSON-4832/news/Johnson-Johnson-Ethicon-E . . . .
http://www.medicalexpo.com/medical-manufacturer/electrosurgical-generator-6951.html.
http://www.megadyne.com/es_generator.php.
http://www.valleylab.com/product/es/generators/index.html.
Covidien 501(k) Summary Sonicision, dated Feb. 24, 2011 (7 pages).
Gerhard, Glen C., "Surgical Electrotechnology: Quo Vadis?," Biomedical Engineering, IEEE Transactions on, vol. BME-31, No. 12, pp. 787, 792, Dec. 1984.
Fowler, K.R., "A programmable, arbitrary waveform electrosurgical device," Engineering in Medicine and Biology Society, 1998. Proceedings of the Annual International Conference of the IEEE, vol. No. pp. 1324, 1325 vol. 3, Nov. 4-7, 1988.
LaCourse, J.R.; Vogt, M.C.; Miller, W.T., III; Selikowitz, S.M., "Spectral analysis interpretation of electro-surgical generator nerve and muscle stimulation," Biomedical Engineering, IEEE Transactions on, vol. 35, No. 7, pp. 505, 509, Jul. 1988.
U.S. Appl. No. 13/751,680, filed Jan. 28, 2013.

\* cited by examiner

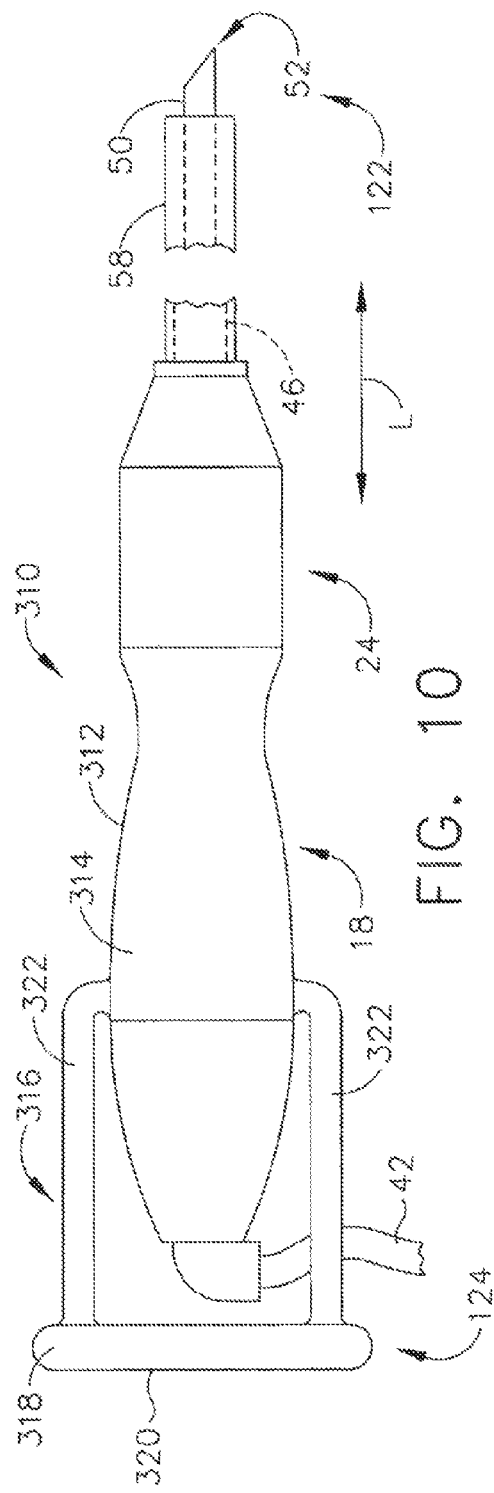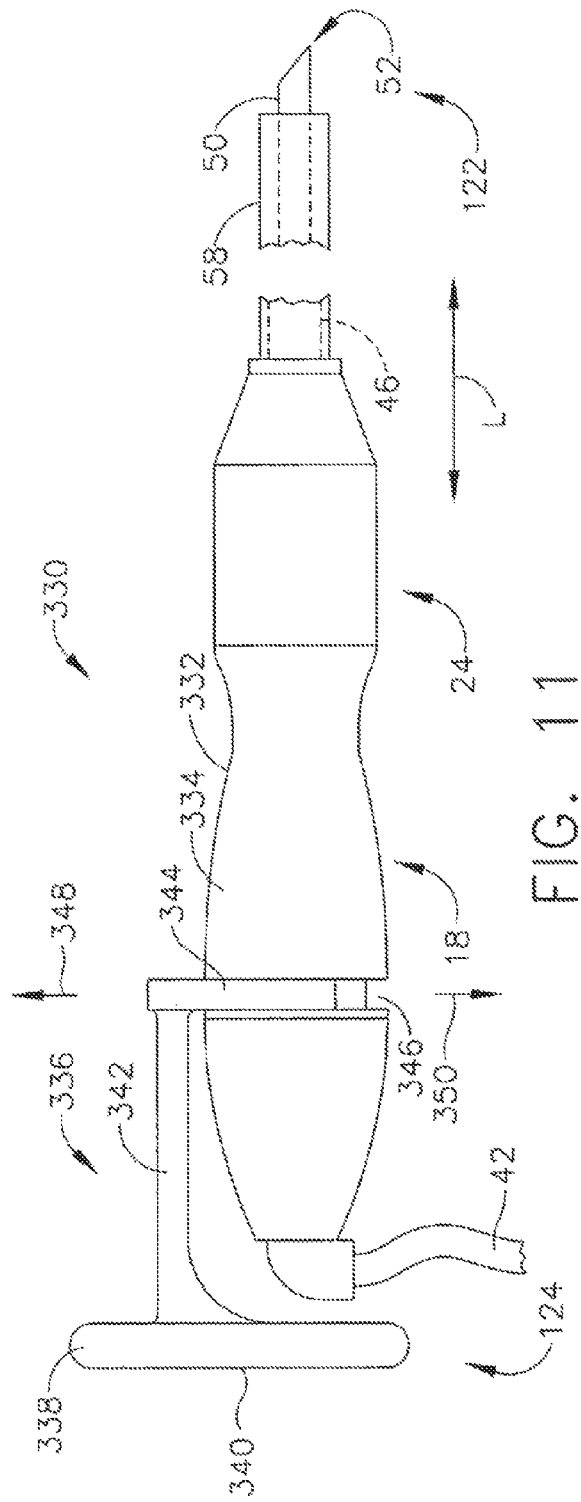

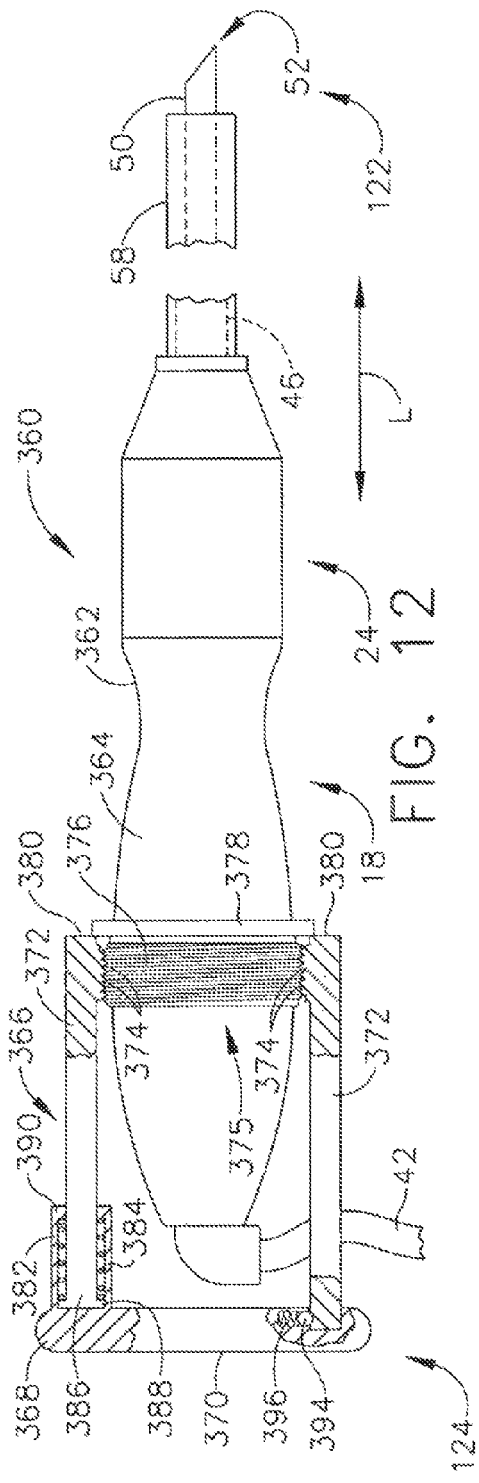
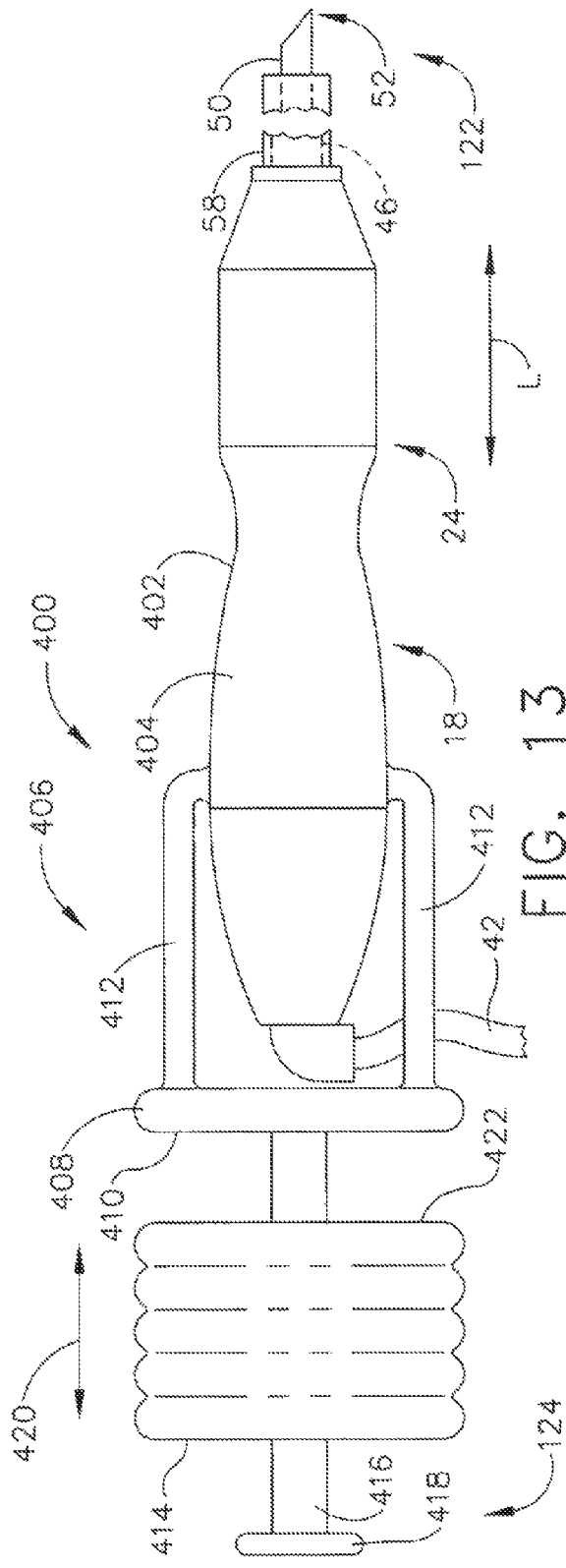
FIG. 12
FIG. 13

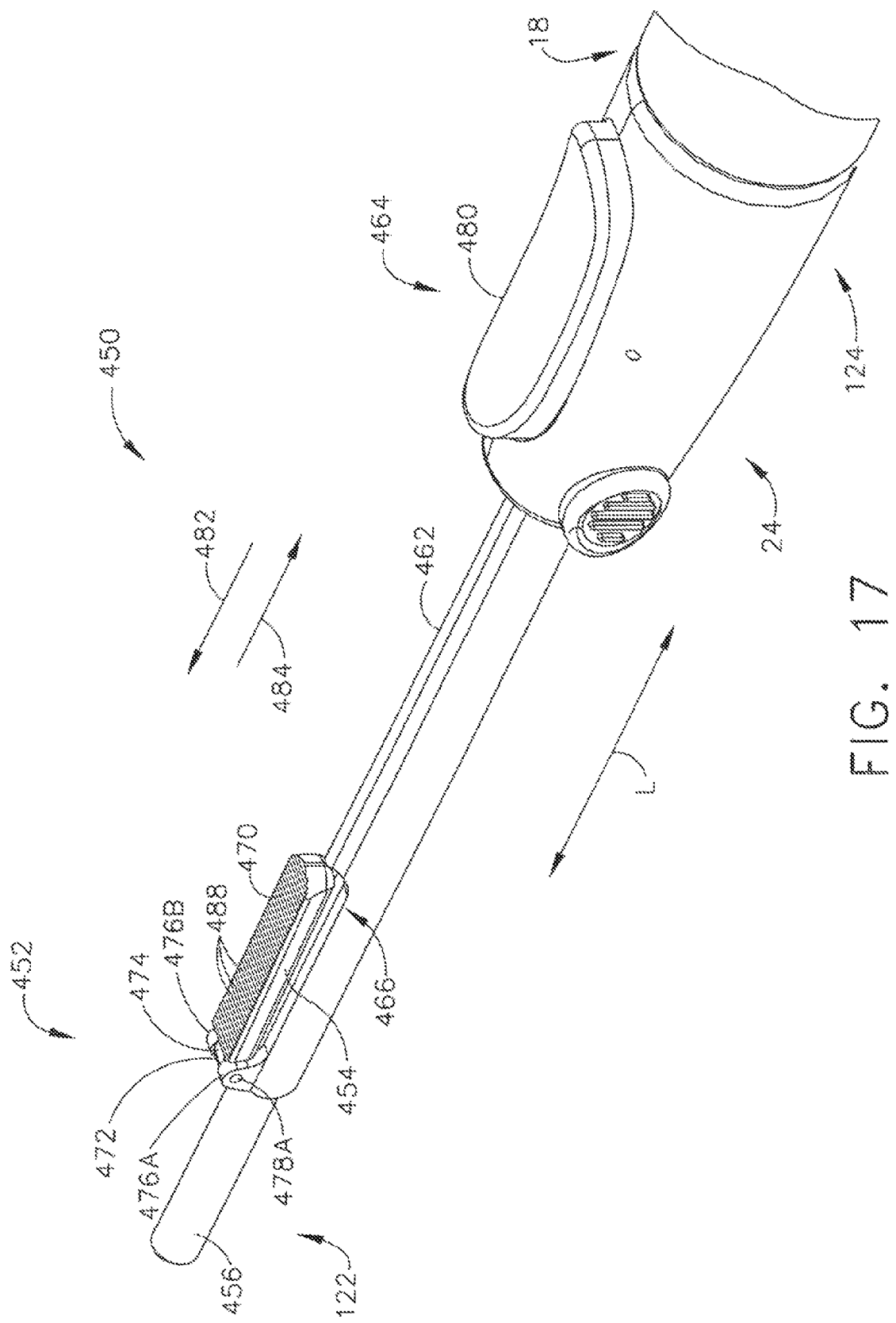

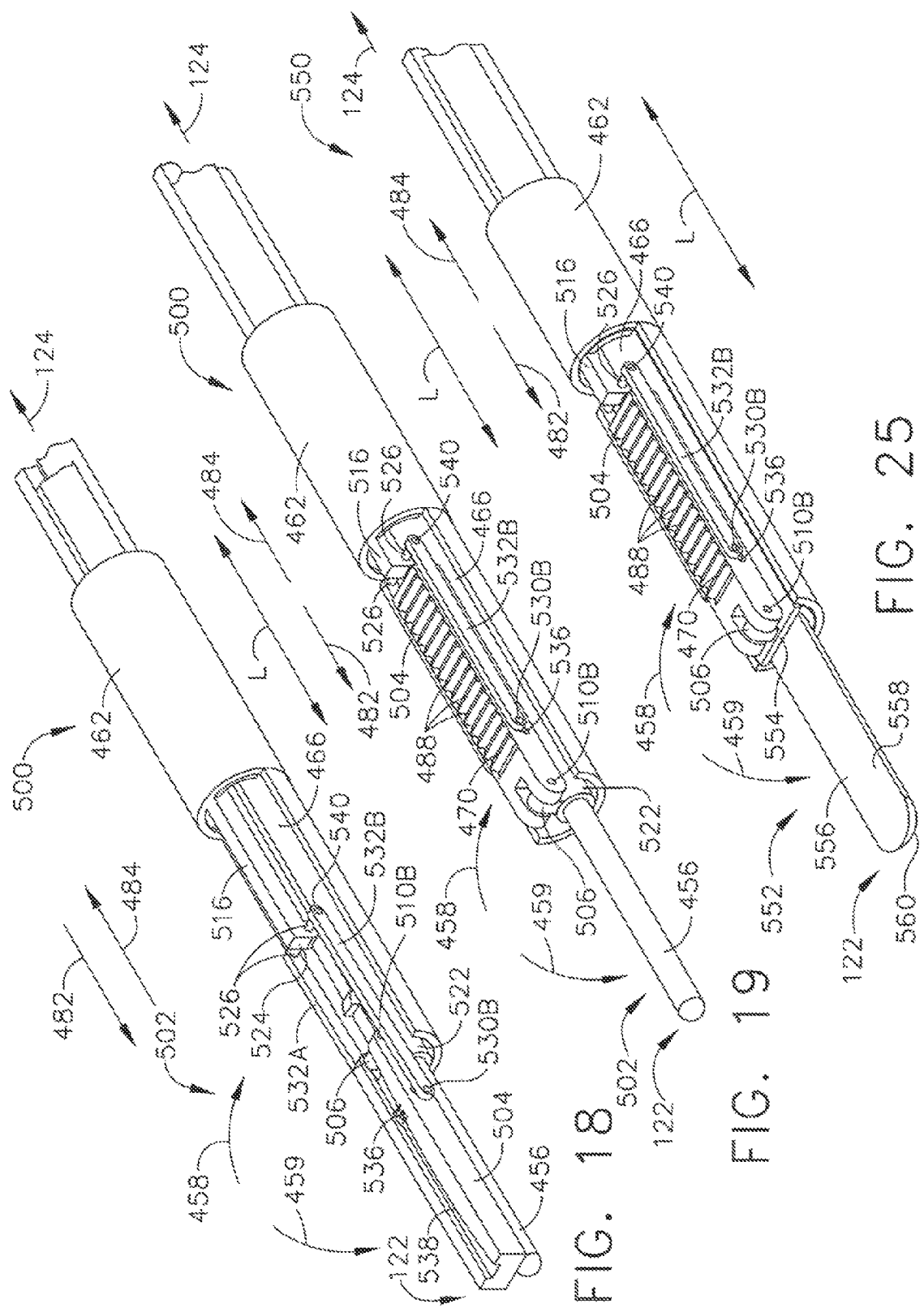

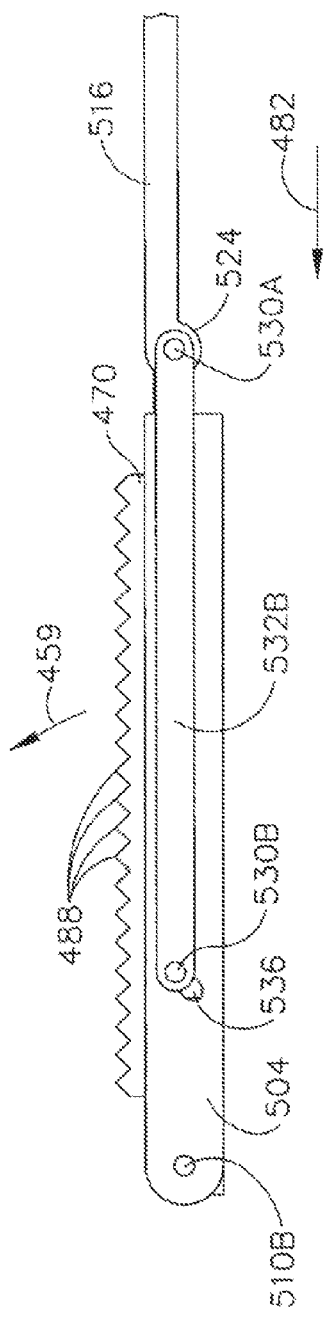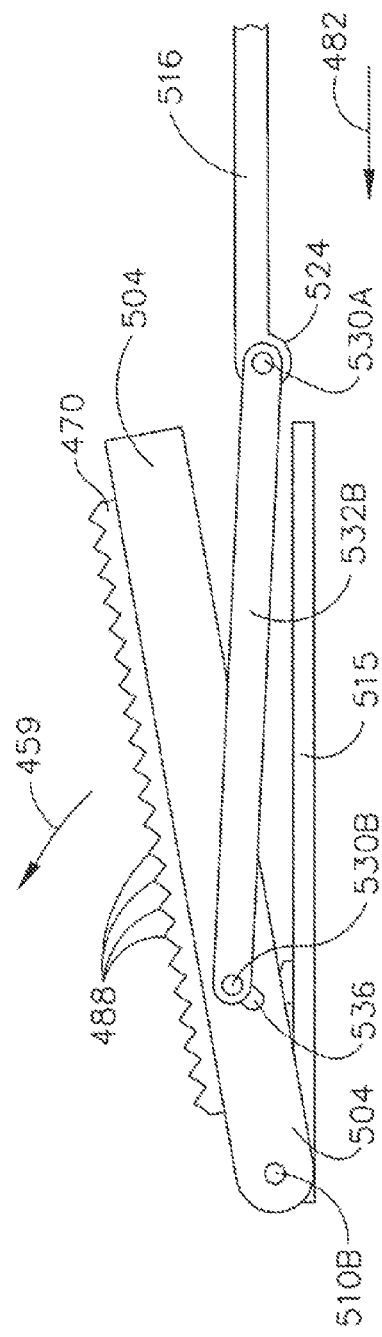
FIG. 21
FIG. 22

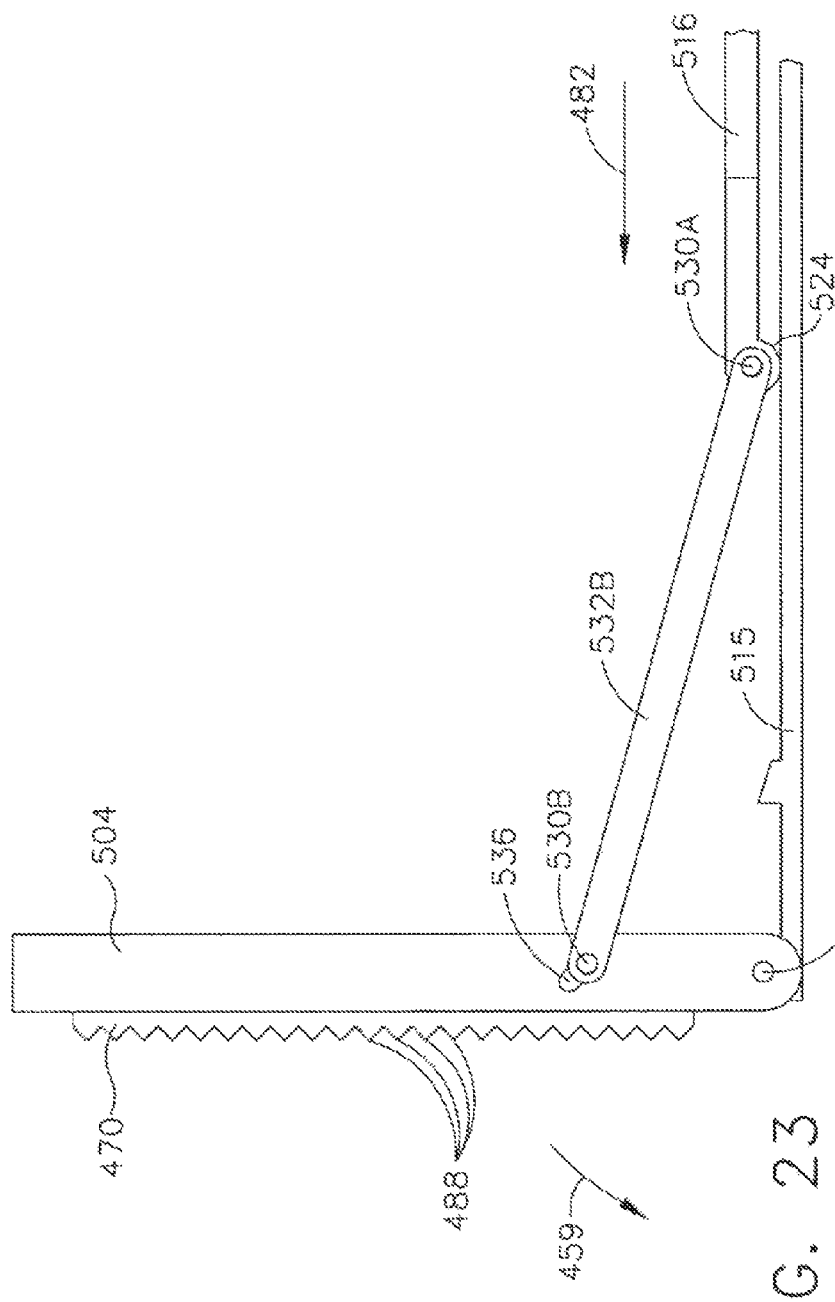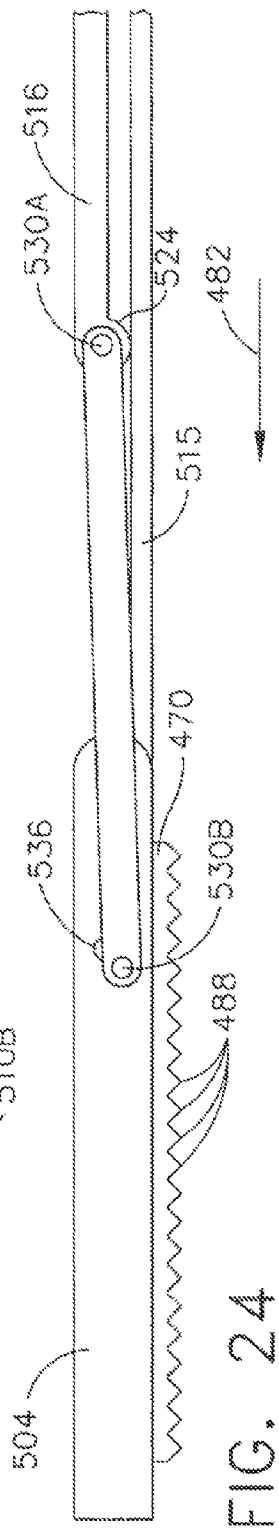

SURGICAL INSTRUMENTS

CROSS REFERENCE TO RELATED APPLICATIONS

The present application is a divisional application claiming the benefit under 35 U.S.C. §121 to U.S. patent application Ser. No. 11/726,760, entitled SURGICAL INSTRUMENTS, filed on Mar. 22, 2007, now U.S. Pat. No. 8,226,675, the entire disclosure of which is hereby incorporated by reference herein.

BACKGROUND

The present application is related to the following, U.S. patent applications, filed on Mar. 22, 2007 which are incorporated herein by reference in their respective entireties:

(1) U.S. patent application Ser. No. 11/726,625, published as U.S. Patent Application Publication No. 2008/0234710 on Sep. 25, 2008, entitled ULTRASONIC SURGICAL INSTRUMENTS;

(2) U.S. patent application Ser. No. 11/726,620, now U.S. Pat. No. 8,142,461, issued Mar. 27, 2012, entitled SURGICAL INSTRUMENTS; and (3) U.S. patent application Ser. No. 11/726,621, published as U.S. Patent Application Publication No. 2008/0234709 on Sep. 25, 2008, entitled ULTRASONIC SURGICAL INSTRUMENTS AND CARTILAGE BONE SHAPING BLADES THEREFOR.

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end effector at ultrasonic frequencies. Ultrasonic vibrations, when transmitted to organic tissue at suitable energy levels and using a suitable end effector, may be used to cut, dissect, elevate, coagulate or cauterize tissue, or to separate muscle tissue off bone. Ultrasonic instruments utilizing solid core technology are particularly advantageous because of the amount of ultrasonic energy that may be transmitted from an ultrasonic transducer, through a waveguide, to the surgical end effector. Such instruments may be used for open procedures or minimally invasive procedures, such as endoscopic or laparoscopic procedures, wherein the end effector is passed through a trocar to reach the surgical site.

Activating or exciting the end effector (e.g., cutting blade) of such instruments at ultrasonic frequencies induces longitudinal vibratory movement that generates localized heat within adjacent tissue, facilitating both cutting and coagulation. Because of the nature of ultrasonic instruments, a particular ultrasonically actuated end effector may be designed to perform numerous functions, including, for example, cutting and coagulating.

Ultrasonic vibration is induced in the surgical end effector by electrically exciting a transducer, for example. The transducer may be constructed of one or more piezoelectric or magnetostrictive elements in the instrument hand piece. Vibrations generated by the transducer section are transmitted to the surgical end effector via an ultrasonic waveguide extending from the transducer section to the surgical end effector. The waveguides and end effectors are designed to resonate at the same frequency as the transducer. Therefore, when an end effector is attached to a transducer the overall system frequency is the same frequency as the transducer itself.

The amplitude of the longitudinal ultrasonic vibration at the tip, d, of the end effector behaves as a simple sinusoid at the resonant frequency as given by:

$$d = A \sin(\omega t)$$

where:
$\omega$=the radian frequency which equals $2\pi$ times the cyclic frequency, f; and
A=the zero-to-peak amplitude.
The longitudinal excursion is defined as the peak-to-peak (p-t-p) amplitude, which is just twice the amplitude of the sine wave or 2A.

Solid core ultrasonic instruments may be divided into two types, single element end effector devices and multiple-element end effector. Single element end effector devices include instruments such as scalpels and ball coagulators. Multiple-element end effectors may be employed when substantial pressure may be necessary to effectively couple ultrasonic energy to the tissue. Multiple-element end effectors such as clamping coagulators include a mechanism to press tissue against an ultrasonic blade. Ultrasonic clamp coagulators may be employed for cutting and coagulating tissue, particularly loose and unsupported tissue. Multiple-element end effectors that include an ultrasonic blade in conjunction with a clamp apply a compressive or biasing force to the tissue to promote faster coagulation and cutting of the tissue, with less attenuation of blade motion.

Orthopedic surgery or orthopedics is the branch of surgery concerned with acute, chronic, traumatic, and overuse injuries and other disorders of the musculoskeletal system. Orthopedic surgeons address most musculoskeletal ailments including arthritis, trauma and congenital deformities using both surgical and non-surgical means. Orthopedic procedures include hand surgery, shoulder and elbow surgery, total joint reconstruction (arthroplasty), pediatric orthopedics, foot and ankle surgery, spine surgery, musculoskeletal oncology, surgical sports medicine, and orthopedic trauma. These procedure often require the use of specialized surgical instruments to treat relatively softer musculoskeletal tissue (e.g., muscle, tendon, ligament) and relatively harder musculoskeletal tissue (e.g., bone). Quite often, these orthopedic surgical instruments are hand operated and a single procedure may require the exchange of a number of instruments. It may be desirable, therefore, for a variety of electrically powered and unpowered ultrasonic instruments to perform these orthopedic surgical procedures with more efficiency and precision than is currently achievable with conventional orthopedic surgical instruments while minimizing the need to exchange instruments when cutting, shaping, drilling different types of musculoskeletal tissue.

SUMMARY

In one general aspect, the various embodiments are directed to a surgical instrument that includes an elongated transmission waveguide defining a longitudinal axis. The transmission waveguide has a distal end and a proximal end. The at least one strike surface is formed on the proximal end and is configured to receive vibratory energy.

FIGURES

The novel features of the various embodiments are set forth with particularity in the appended claims. The various embodiments, however, both as to organization and methods of operation, together with further objects and advantages thereof, may best be understood by reference to the following description, taken in conjunction with the accompanying drawings as follows.

FIG. 10 illustrates a side view of one embodiment of an ultrasonic instrument comprising an impact zone.

FIG. 11 illustrates a side view of one embodiment of an ultrasonic instrument comprising an impact zone.

FIG. 12 illustrates a side view of one embodiment of an ultrasonic instrument comprising an impact zone.

FIG. 13 illustrates a side view of one embodiment of an ultrasonic instrument comprising an impact zone.

Figure 14:
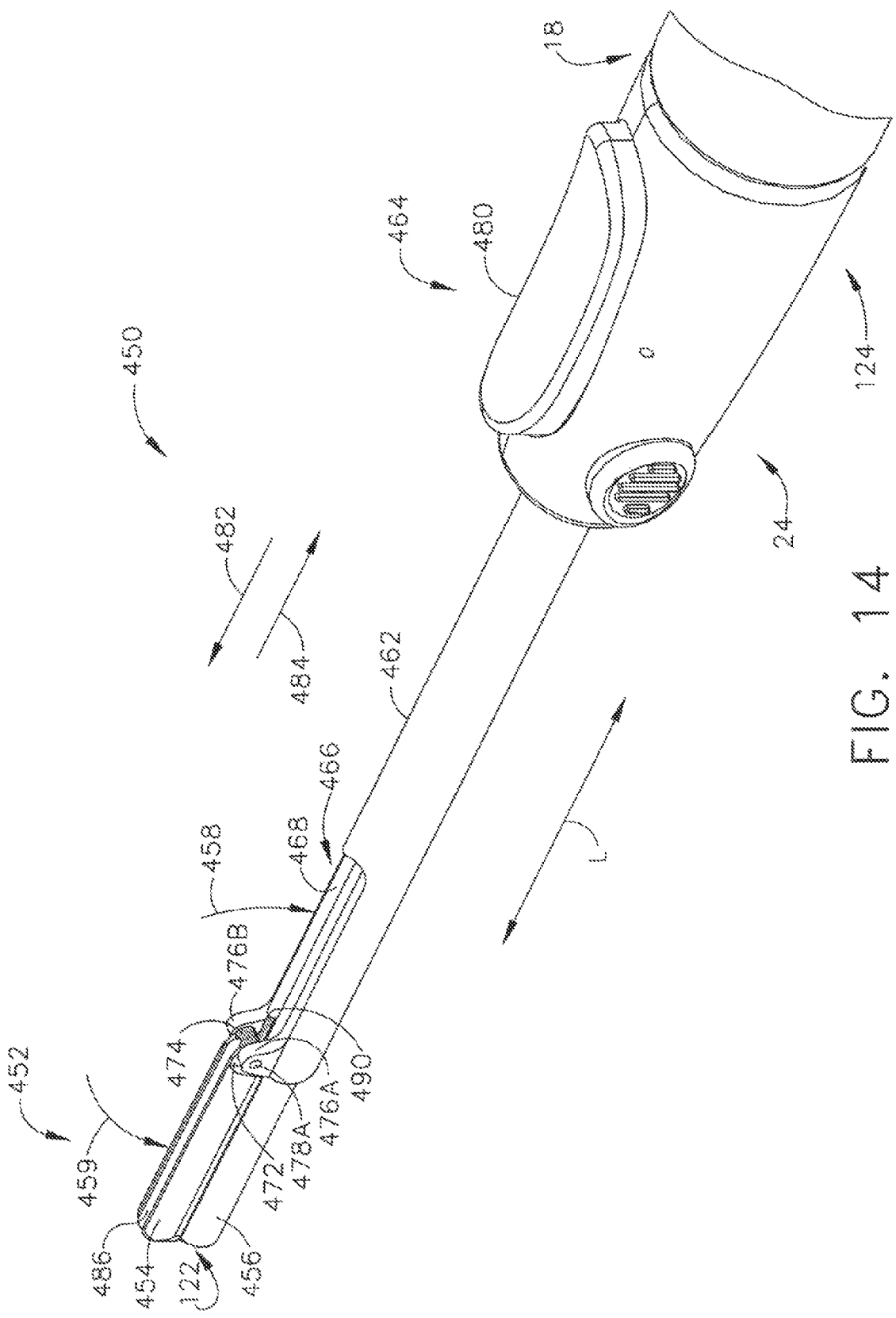
Figure 15:
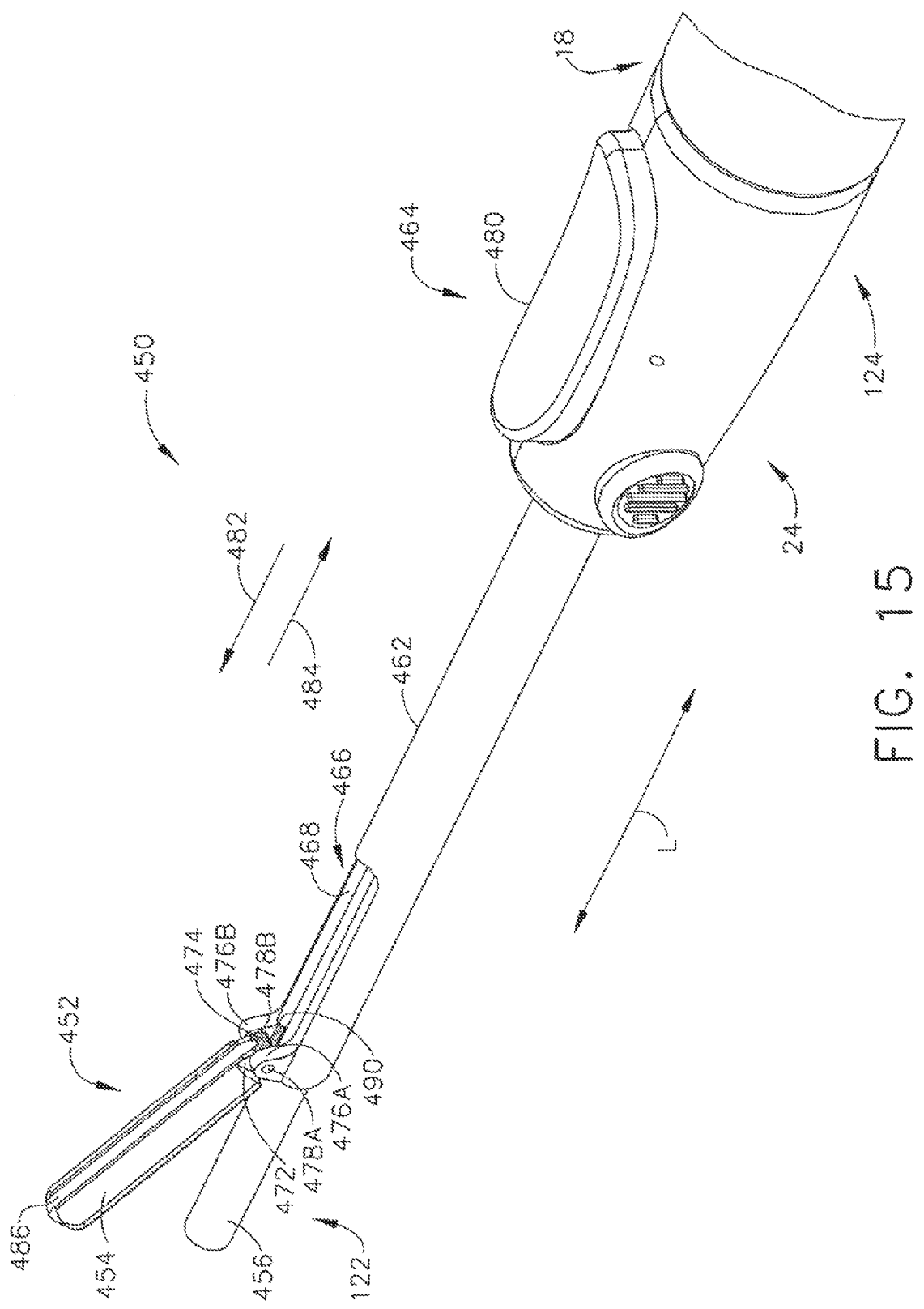
Figure 16:
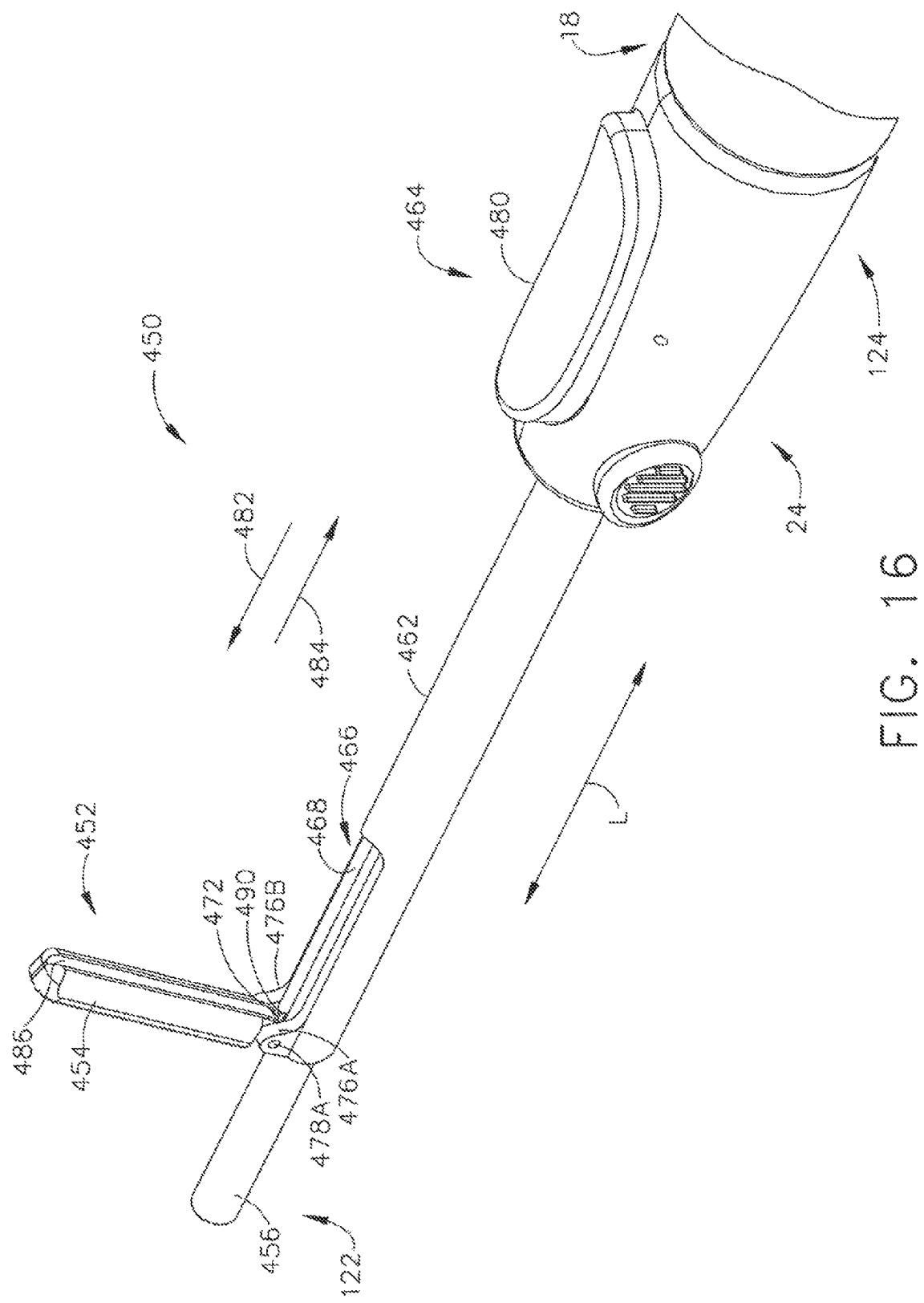

FIGS. 14-17 illustrate one embodiment of an ultrasonic instrument comprising an end effector at a distal end; FIG. 14 is a side perspective view of one embodiment of the ultrasonic instrument with the clamp jaw in a closed position; FIGS. 15 and 16 are side perspective views of the ultrasonic instrument with the clamp jaw in partially open positions; and FIG. 17 is side perspective view of the ultrasonic instrument with the clamp arm assembly in a closed position.

Figure 20:
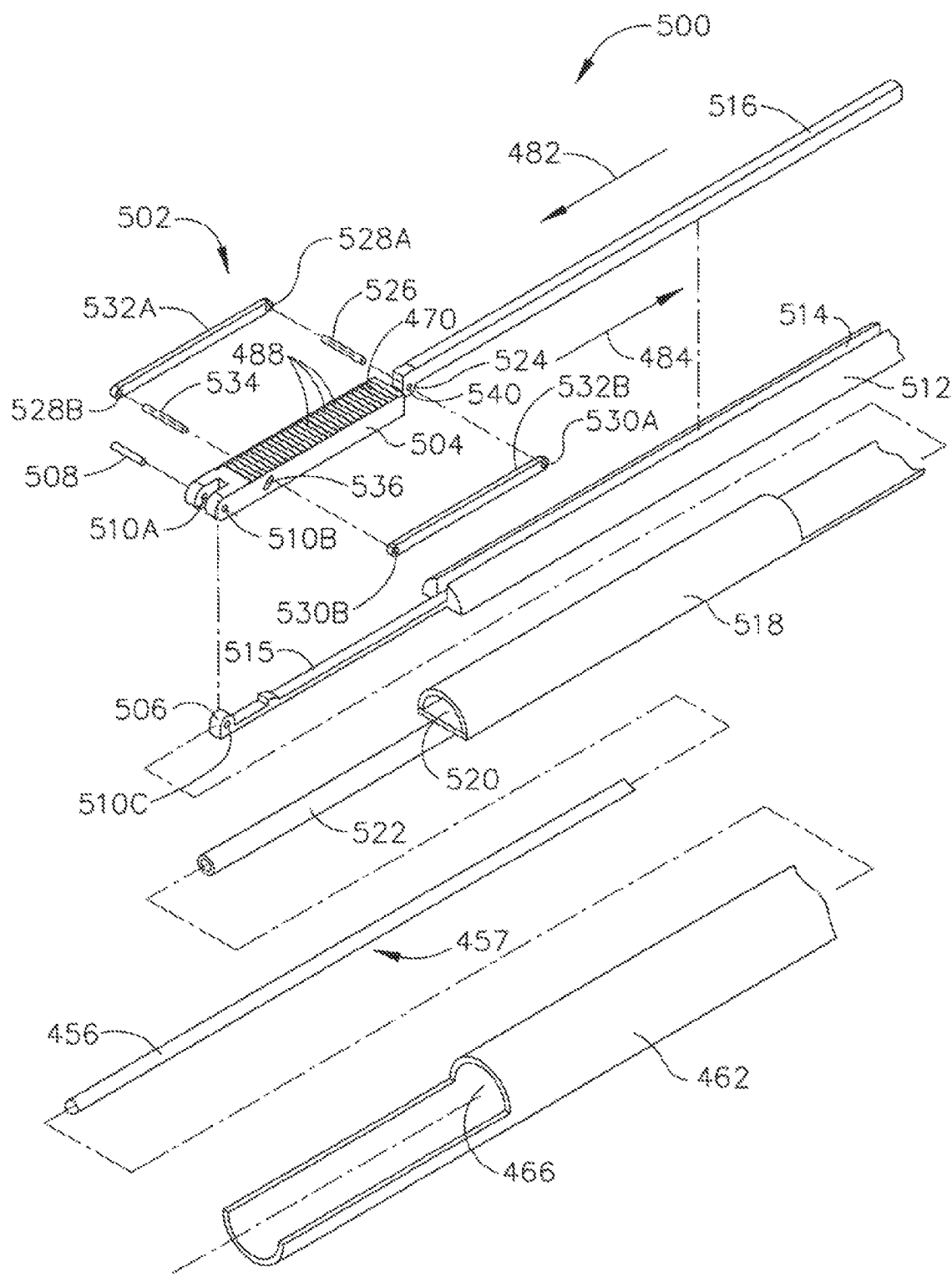

FIGS. 18-20 illustrate one embodiment of an end effector that may be employed with the ultrasonic instrument discussed in FIGS. 14-17; FIG. 18 is a top perspective view of one embodiment of the end effector with the clamp arm assembly in a closed position; FIG. 19 is a top perspective view of one embodiment of the end effector with the clamp arm assembly in an open position; and FIG. 20 is an exploded view of one embodiment of the end effector with the clamp jaw in an open position.

FIGS. 21-24 illustrate a clamp jaw transitioning from an open position in FIG. 21 to a closed position in FIG. 24 and intermediate positions in FIGS. 22 and 23.

Figure 26:
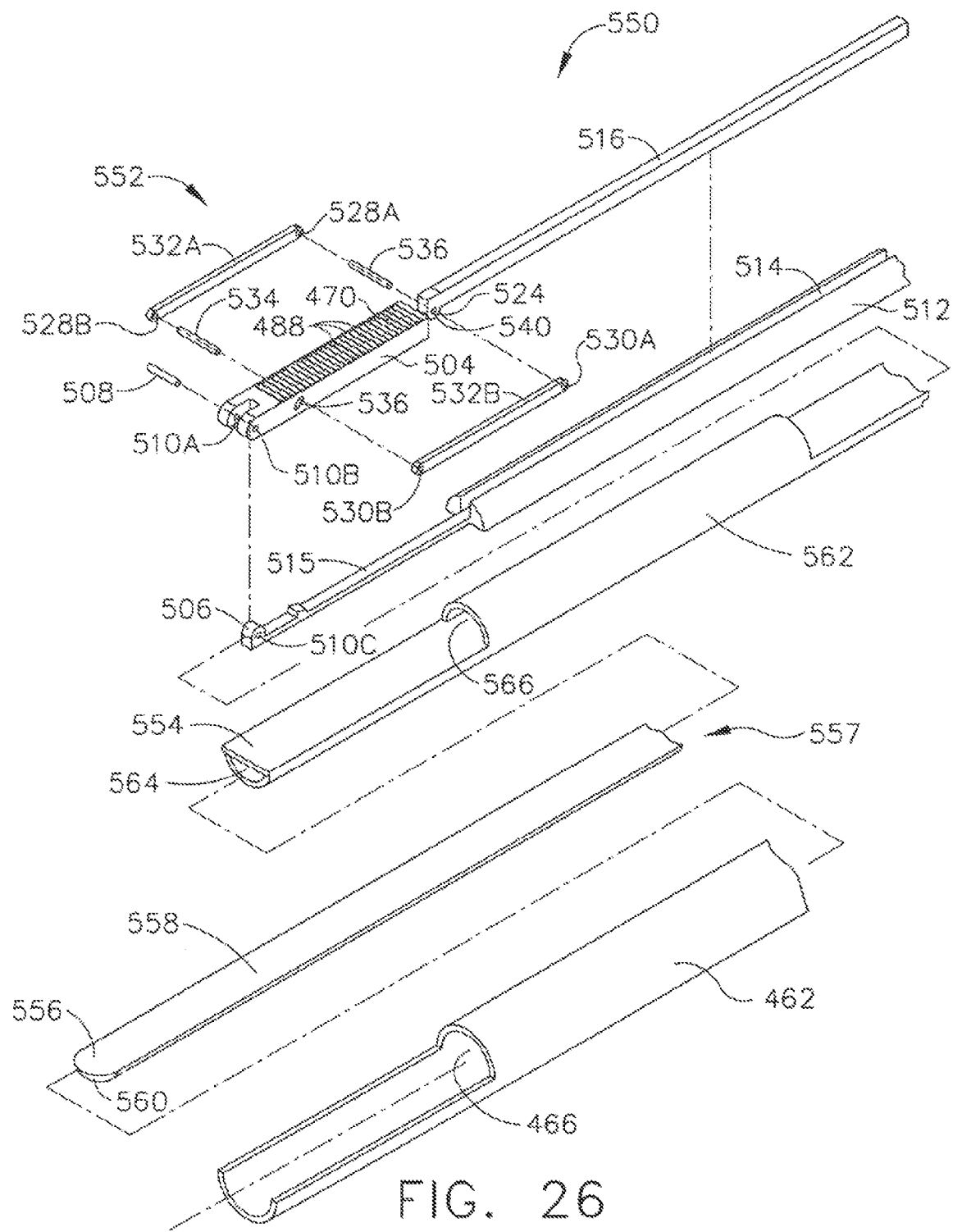

FIGS. 25 and 26 illustrate one embodiment of an end effector that may be employed with the ultrasonic instrument discussed in FIGS. 14-17; FIG. 25 is a top perspective view of one embodiment of the end effector with the clamp arm assembly in an open position; and FIG. 26 is an exploded view of one embodiment of the end effector with the clamp jaw in an open position.

DESCRIPTION

Before explaining embodiments of the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. For example, the surgical instruments and blade configurations disclosed below are illustrative only and not meant to limit the scope or application of the invention. Furthermore, unless otherwise indicated, the terms and expressions employed herein have been chosen for the purpose of describing the illustrative embodiments of the present invention for the convenience of the reader and are not for the purpose of limiting the invention.

The various embodiments described herein are generally directed to surgical instruments. Although these surgical instruments may be employed in orthopedic surgical procedures, the described embodiments are not limited in this context as these instruments may find useful applications outside of this particular branch of medicine. The various embodiments described herein are directed to surgical instruments that may be used in a stand alone or in combination with ultrasonically driven surgical instruments. In some embodiments, the surgical instruments may be driven either manually or electrically, or may be driven manually and electrically in combination. Surgical instruments configured to operate in multiple powered and unpowered states modes may reduce the total number of instruments in the operating room, reduces the number of instrument exchanges for a given procedure, and reduces the number of instruments that have to be sterilized for a given procedure. In other embodiments, surgical instruments may attain useful longitudinal vibrational resonance to assist cutting, reshaping, or coagulating tissue without an electrically driven actuator or an ultrasonic transducer. In yet other embodiments, electrically powered ultrasonic instruments may be used in combination with manual techniques to carry out surgical procedures with greater efficiency and precision.

Examples of ultrasonic instruments are disclosed in U.S. Pat. Nos. 5,322,055 and 5,954,736 and in combination with ultrasonic blades and surgical instruments disclosed in U.S. Pat. Nos. 6,309,400 B2, 6,278,218B1, 6,283,981 B1, and 6,325,811 B1, for example, are incorporated herein by reference in their entirety. These references disclose ultrasonic instrument design and blade designs where a longitudinal node of the blade is excited. Because of asymmetry or asymmetries, these blades exhibit transverse and/or torsional motion where the characteristic "wavelength" of this non-longitudinal motion is less than that of the general longitudinal motion of the blade and its extender portion. Therefore, the wave shape of the non-longitudinal motion will present nodal positions of transverse/torsional motion along the tissue effector while the net motion of the active blade along its tissue effector is non-zero (i.e., will have at least longitudinal motion along the length extending from its distal end, an antinode of longitudinal motion, to the first nodal position of longitudinal motion that is proximal to the tissue effector portion). Certain embodiments will now be described in the form of examples to provide an overall understanding of the principles of the structure, function, manufacture, and use of the devices and methods disclosed herein. One or more of these embodiments are illustrated in the accompanying drawings in the form of illustrative examples. Those of ordinary skill in the art will understand that the devices and methods specifically described herein and illustrated in the accompanying drawings are non-limiting example embodiments and that the scope of the various embodiments is defined solely by the claims. The features illustrated or described in connection with one example embodiment may be combined with the features of other embodiments. Such modifications and variations are intended to be included within the scope of the claims.

Figure 1:
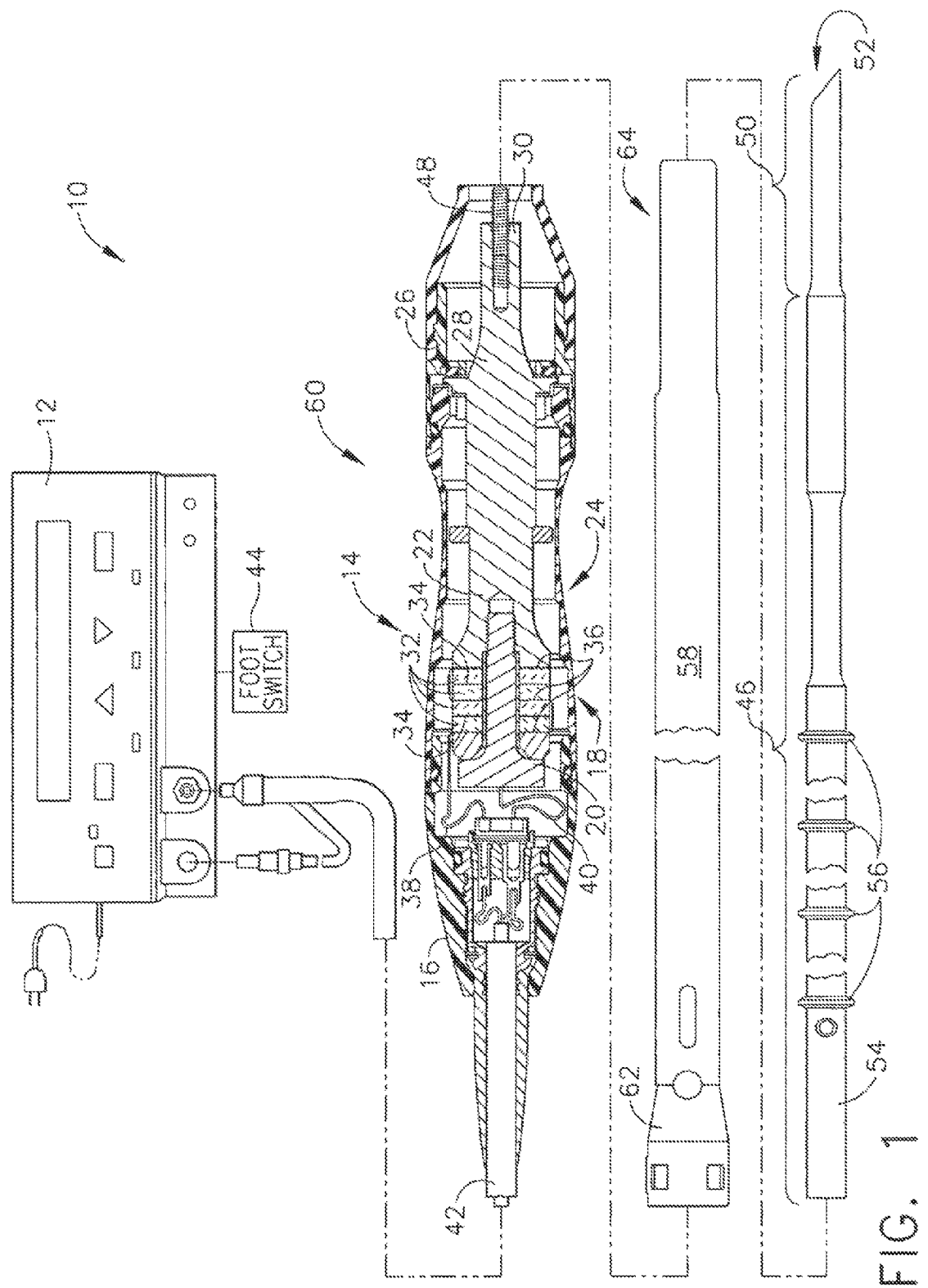
FIG. 1 illustrates one embodiment of an ultrasonic system.

FIG. 1 illustrates one embodiment of an ultrasonic system 10. In the illustrated embodiment, the ultrasonic system 10 comprises an ultrasonic signal generator 12 coupled to an ultrasonic transducer 14, a hand piece assembly 60 comprising a hand piece housing 16, and an end effector 50. The end effector 50 may have a chisel like shape adapted and configured to cut bone tissue, may have a rounded end adapted and configured to drill small holes in bone tissue, and/or may configured to cut, coagulate, and/or shape tissue. The ultrasonic transducer 14, which is known as a "Langevin stack", generally includes a transduction portion 18, a first resonator or end-bell 20, and a second resonator or fore-bell 22, and ancillary components. The ultrasonic transducer 14 is preferably an integral number of one-half system wavelengths ($n\lambda/2$) in length as will be described in more detail later. An acoustic assembly 24 includes the ultrasonic transducer 14, a mount 26, a velocity transformer 28, and a surface 30.

It will be appreciated that the terms "proximal" and "distal" are used herein with reference to a clinician gripping the hand piece assembly 60. Thus, the end effector 50 is distal with respect to the more proximal hand piece assembly 60. It will be further appreciated that, for convenience and clarity, spatial terms such as "top" and "bottom" also are used herein with respect to the clinician gripping the hand piece assembly 60. However, surgical instruments are used in many orientations and positions, and these terms are not intended to be limiting and absolute.

The distal end of the end-bell 20 is connected to the proximal end of the transduction portion 18, and the proximal end of the fore-bell 22 is connected to the distal end of the transduction portion 18. The fore-bell 22 and the end-bell 20 have a length determined by a number of variables, including the thickness of the transduction portion 18, the density and modulus of elasticity of the material used to manufacture the end-bell 20 and the fore-bell 22, and the resonant frequency of the ultrasonic transducer 14. The fore-bell 22 may be tapered inwardly from its proximal end to its distal end to amplify the ultrasonic vibration amplitude as the velocity transformer 28, or alternately may have no amplification. A suitable vibrational frequency range may be about 20 Hz to 120 kHz and a well-suited vibrational frequency range may be about 30-70 kHz and one example operational vibrational frequency may be approximately 55.5 kHz.

Piezoelectric elements 32 may be fabricated from any suitable material, such as, for example, lead zirconate-titanate, lead meta-niobate, lead titanate, or other piezoelectric crystal material. Each of positive electrodes 34, negative electrodes 36, and the piezoelectric elements 32 has a bore extending through the center. The positive and negative electrodes 34 and 36 are electrically coupled to wires 38 and 40, respectively. The wires 38 and 40 are encased within a power cable 42 and electrically connectable to the ultrasonic signal generator 12 of the ultrasonic system 10.

The ultrasonic transducer 14 of the acoustic assembly 24 converts the electrical signal from the ultrasonic signal generator 12 into mechanical energy that results in primarily longitudinal vibratory motion of the ultrasonic transducer 14 and the end effector 50 at ultrasonic frequencies. A suitable generator is available as model number GEN04, from Ethicon Endo-Surgery, Inc., Cincinnati, Ohio. When the acoustic assembly 24 is energized, a vibratory motion standing wave is generated through the acoustic assembly 24. The amplitude of the vibratory motion at any point along the acoustic assembly 24 may depend upon the location along the acoustic assembly 24 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node (i.e., where motion is usually maximal). The distance between an anti-node and its nearest node is one-quarter wavelength ($\lambda/4$).

The wires 38 and 40 transmit an electrical signal from the ultrasonic signal generator 12 to the positive electrodes 34 and the negative electrodes 36. The piezoelectric elements 32 are energized by the electrical signal supplied from the ultrasonic signal generator 12 in response to a foot switch 44 to produce an acoustic standing wave in the acoustic assembly 24. The electrical signal causes disturbances in the piezoelectric elements 32 in the form of repeated small displacements resulting in large compression forces within the material. The repeated small displacements cause the piezoelectric elements 32 to expand and contract in a continuous manner along the axis of the voltage gradient, producing longitudinal waves of ultrasonic energy. The ultrasonic energy is transmitted through the acoustic assembly 24 to the end effector 50 via an ultrasonic transmission waveguide 46.

In order for the acoustic assembly 24 to deliver energy to the end effector 50, all components of the acoustic assembly 24 must be acoustically coupled to the end effector 50. The distal end of the ultrasonic transducer 14 may be acoustically coupled at the surface 30 to the proximal end of the ultrasonic transmission waveguide 46 by a threaded connection such as a stud 48.

The components of the acoustic assembly 24 are preferably acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of the acoustic assembly 24, and where n is any positive integer. It is also contemplated that the acoustic assembly 24 may incorporate any suitable arrangement of acoustic elements.

The ultrasonic end effector 50 may have a length substantially equal to an integral multiple of one-half system wavelengths ($\lambda/2$). A distal end 52 of the ultrasonic end effector 50 may be disposed near an antinode in order to provide the maximum longitudinal excursion of the distal end 52. When the transducer assembly is energized, the distal end 52 of the ultrasonic end effector 50 may be configured to move in the range of, for example, approximately 10 to 500 microns peak-to-peak, and preferably in the range of about 30 to 150 microns at a predetermined vibrational frequency.

The ultrasonic end effector 50 may be coupled to the ultrasonic transmission waveguide 46. The ultrasonic end effector 50 and the ultrasonic transmission guide 46 as illustrated are formed as a single unit construction from a material suitable for transmission of ultrasonic energy such as, for example, Ti6Al4V (an alloy of Titanium including Aluminum and Vanadium), Aluminum, Stainless Steel, or other known materials. Alternately, the ultrasonic end effector 50 may be separable (and of differing composition) from the ultrasonic transmission waveguide 46, and coupled by, for example, a stud, weld, glue, quick connect, or other suitable known methods. The ultrasonic transmission waveguide 46 may have a length substantially equal to an integral number of one-half system wavelengths (nλ/2), for example. The ultrasonic transmission waveguide 46 may be preferably fabricated from a solid core shaft constructed out of material that propagates ultrasonic energy efficiently, such as titanium alloy (i.e., Ti-6Al-4V) or an aluminum alloy, for example.

The ultrasonic transmission waveguide 46 comprises a longitudinally projecting attachment post 54 at a proximal end to couple to the surface 30 of the ultrasonic transmission waveguide 46 by a threaded connection such as the stud 48. In the illustrated embodiment, the ultrasonic transmission waveguide 46 comprises a plurality of stabilizing silicone rings or compliant supports or silicon rings are 56 positioned at a plurality of nodes. The silicone rings 56 dampen undesirable vibration and isolate the ultrasonic energy from a removable sheath 58 assuring the flow of ultrasonic energy in a longitudinal direction to the distal end 52 of the end effector 50 with maximum efficiency.

As shown in FIG. 1, the removable sheath 58 is coupled to the distal end of the handpiece assembly 60. The sheath 58 generally includes an adapter or nose cone 62 and an elongated tubular member 64. The tubular member 64 (e.g., outer tube) is attached to the adapter 62 and has an opening extending longitudinally therethrough. The sheath 58 may be threaded or snapped onto the distal end of the housing 16. The ultrasonic transmission waveguide 46 extends through the opening of the tubular member 64 and the silicone rings 56 isolate the ultrasonic transmission waveguide 46 therein.

The adapter 62 of the sheath 58 may be fabricated from plastic such as Ultem®, aluminum, or any suitable material, and the tubular member 64 may be fabricated from stainless steel. Alternatively, the ultrasonic transmission waveguide 46 may have polymeric material surrounding it to isolate it from outside contact.

The distal end of the ultrasonic transmission waveguide 46 may be coupled to the proximal end of the end effector 50 by an internal threaded connection, preferably at or near an antinode. It is contemplated that the end effector 50 may be attached to the ultrasonic transmission waveguide 46 by any suitable means, such as a welded joint or the like. Although the end effector 50 may be detachable from the ultrasonic transmission waveguide 46, it is also contemplated that the end effector 50 and the ultrasonic transmission waveguide 46 may be formed as a single unitary piece.

In one embodiment, the handpiece housing 16 of the ultrasonic handpiece assembly 60 may be configured to receive or accommodate a mechanical impact such as, for example, a mallet blow or hand blow, and impart energy into the end effector 50 when the hand piece assembly 60 is in a powered or an unpowered state. In another embodiment, the handpiece assembly 60 may comprise a strike plate assembly such as those described below in FIGS. 10-13, for example. Thus, in use a clinician may employ the handpiece assembly 60 in a powered state using the ultrasonic vibrations generated by the transduction portion 18 to cut and coagulate relatively soft musculoskeletal tissue using a chisel shaped end effector 50. With the handpiece assembly 60 in a powered or an unpowered state, the clinician may deliver a strike to the distal end of the housing 16 manually or with employing an osteotome mallet to chisel relatively hard musculoskeletal tissue such as bone.

Figure 2:
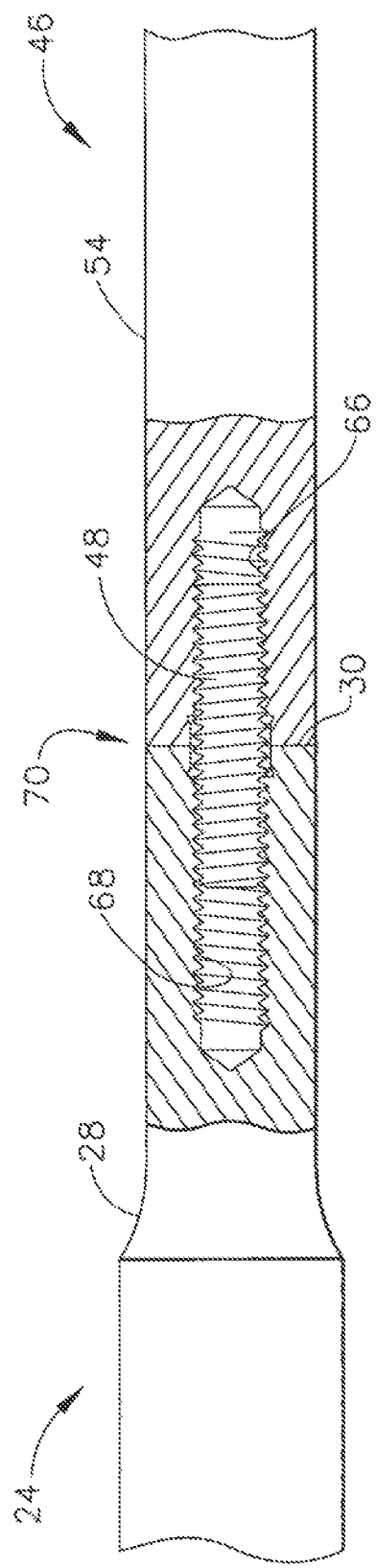
FIG. 2 illustrates one embodiment of a connection union/joint for an ultrasonic instrument.

FIG. 2 illustrates one embodiment of a connection union/joint 70 for an ultrasonic instrument. In the illustrated embodiment, the connection union/joint 70 may be formed between the attachment post 54 of the ultrasonic transmission waveguide 46 and the surface 30 of the velocity transformer 28 at the distal end of the acoustic assembly 24. The proximal end of the attachment post 54 comprises a female threaded substantially cylindrical recess 66 to receive a portion of the threaded stud 48 therein. The distal end of the velocity transformer 28 also may comprise a female threaded substantially cylindrical recess 68 to receive a portion of the threaded stud 40. The recesses 66, 68 are substantially circumferentially and longitudinally aligned.

Figure 3:
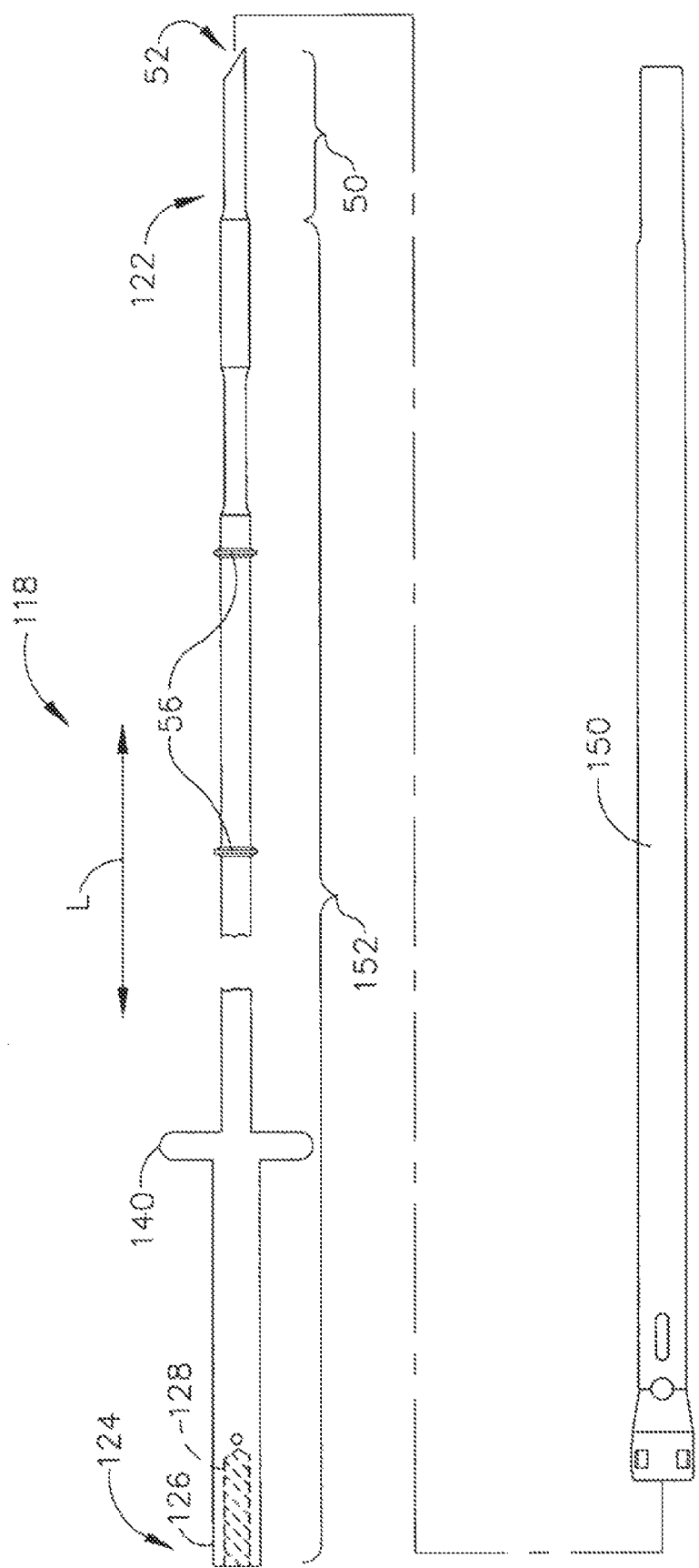
FIG. 3 illustrates one embodiment of an ultrasonic subassembly that may be configured to couple to the ultrasonic hand piece assembly of the ultrasonic system described in FIG. 1.

FIG. 3 illustrates one embodiment of an ultrasonic subassembly 118 that may be configured to couple to the ultrasonic hand piece assembly 60 of the ultrasonic system 10 described in FIG. 1. In the illustrated embodiment, the ultrasonic subassembly 118 may be configured to couple to the surface 30 of the ultrasonic system 10 described in FIG. 1. In one embodiment, the ultrasonic subassembly 118 comprises a sheath or outer tube 150, an ultrasonic transmission waveguide 152, and the end effector 50 having a distal end 52 at an anti-node. The outer tube 150 has an opening extending longitudinally therethrough. The ultrasonic transmission waveguide 152 comprises a distal end 122 and a proximal end 124 and defines a longitudinal axis "L". The proximal end 124 comprises a neck or transition portion 126 to attach or couple to the ultrasonic transmission surface 30 of the hand-piece assembly 60 by a stud, weld, glue, quick connect, or other known attachment methods, for example. It will be appreciated the shape of the neck 126 may be configured to provide efficient ultrasonic coupling to the surface 30. In the illustrated embodiment, the neck 126 comprises a female threaded substantially cylindrical recess 128 to receive a portion of the threaded stud 48 therein. The silicone rings 56 dampen undesirable vibration and isolate the ultrasonic energy from the removable outer tube 150. A flange or proximal stop 140 is integrally formed and tuned with the ultrasonic transmission waveguide 152 and is explained in further detail below.

Although the ultrasonic subassembly 118 may be ultrasonically coupled to the hand piece assembly 60 as described herein, those of ordinary skill in the art will understand that the various embodiments of the ultrasonic instruments disclosed herein as well as any equivalent structures thereof could conceivably be effectively used in connection with other known ultrasonic instruments without departing from the scope thereof. Thus, the embodiments disclosed herein should not be limited to use only in connection with the example ultrasonic instrument described above.

Figure 4:
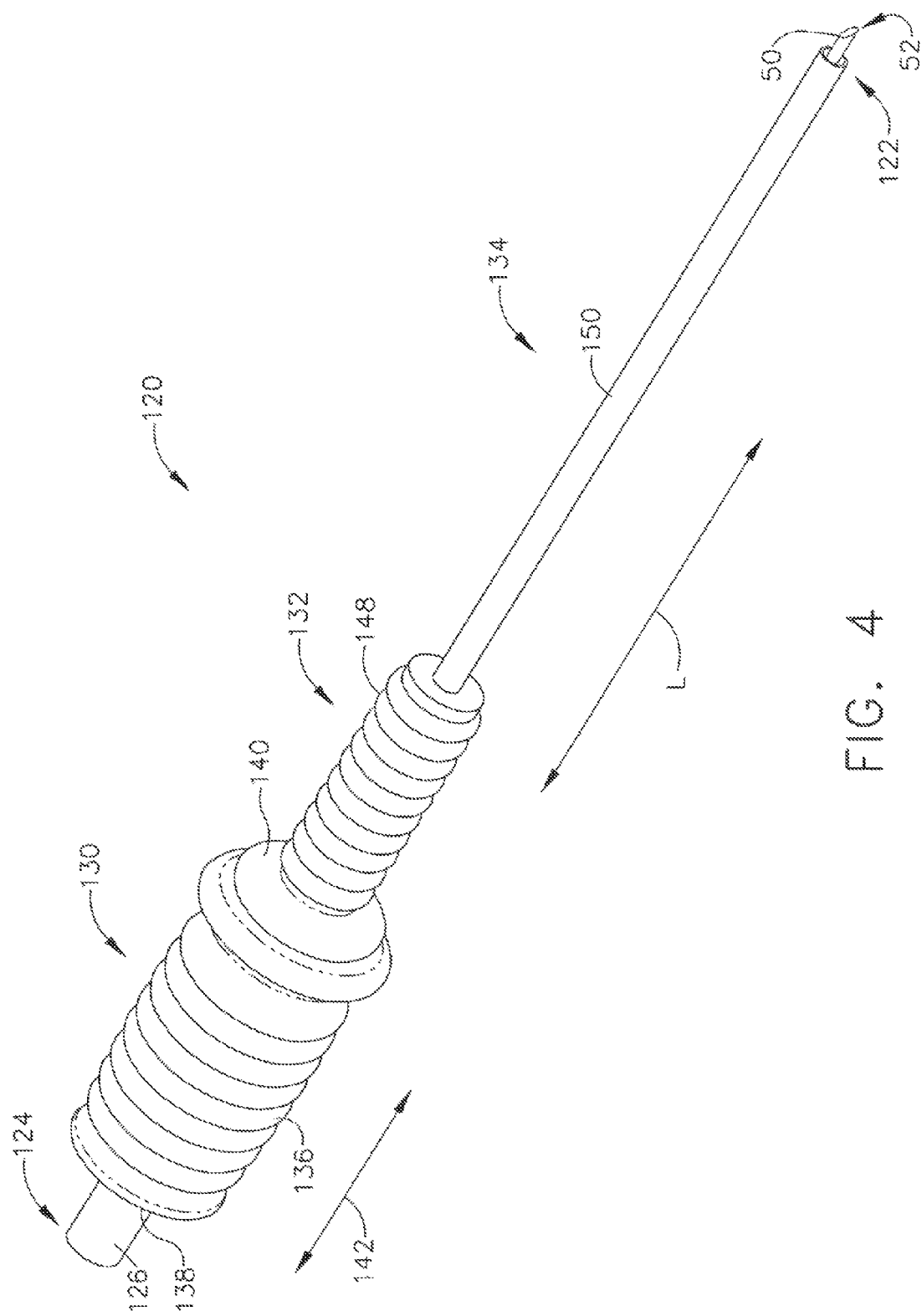
FIG. 4 is a top perspective view of one embodiment of an ultrasonic instrument.
Figure 5:
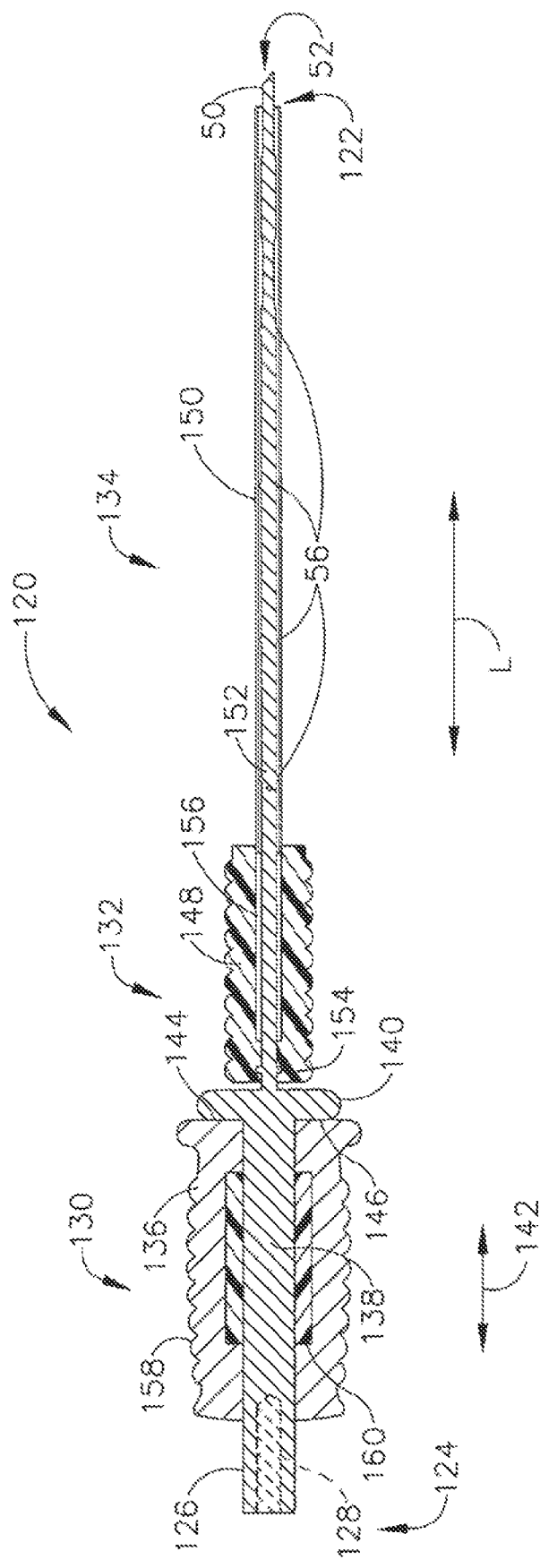
FIG. 5 is a cross-sectional view of one embodiment of the ultrasonic instrument shown in FIG. 4 taken along the longitudinal axis "L".

FIG. 4 is a top perspective view of one embodiment of an ultrasonic instrument 120. FIG. 5 is a cross-sectional view of one embodiment of the ultrasonic instrument 120 taken along the longitudinal axis "L". With reference to FIGS. 4 and 5, in the illustrated embodiment, the surgical instrument 120 comprises the ultrasonic subassembly 118 shown in FIG. 3. The ultrasonic instrument 120 comprises the ultrasonic transmission waveguide 152, the outer tube 150, and the end effector 50. The ultrasonic instrument 120 is well-suited for effecting musculoskeletal tissue comprising bones, muscles, joints, and the associated periarticular tissues such as tendons, ligaments, cartilage, joints, and spinal discs. Tissue effects comprise cutting, coagulating, and drilling. The end effector 50 may have a chisel like shape adapted and configured to cut bone tissue or may have a rounded end adapted and configured to drill small holes in bone tissue. The ultrasonic instrument 120 is adapted to couple to the hand piece assembly 60 of the ultrasonic system 10 in the manner described with respect to ultrasonic subassembly 118 described in FIG. 3. In one embodiment, the ultrasonic instrument 120 may be coupled to the hand piece assembly 60 with by a threaded connection such as the stud 48 or may be coupled by weld, glue, quick connect, or other suitable known methods.

The ultrasonic instrument 120 comprises a distal end 122 and a proximal end 124 and defines a longitudinal axis "L". The proximal end 124 comprises the neck or transition portion 126 that protrudes from the proximal end 124. The neck portion 126 may be attached to the ultrasonic transmission surface 30 by a stud, weld, glue, quick connect, or other known attachment methods, for example. The proximal end 124 comprises the female threaded substantially cylindrical recess 128 to receive a portion of the threaded stud 48 therein. The ultrasonic instrument 120 is ultrasonically coupled to the hand piece assembly 60.

The ultrasonic instrument 120 comprises a "slap hammer" portion 130, a gripping portion 132, and a longitudinally extending end effector portion 134. The slap hammer portion 130 comprises a slap hammer 136 that is slideably movable in the direction indicated by arrow 142 over a proximal shaft 138 to the flange or proximal stop 140. The gripping portion 132 comprises a grip 148 positioned distally beyond the proximal stop 140 positioned over a proximal sleeve 156 (e.g., bushing). A distal portion of the ultrasonic transmission waveguide 152 is positioned inside the longitudinal opening extending through the outer tube 150 portion of the end effector portion 134. The grip 148 is fixedly mounted by a ring or circumferential projection 154. The circumferential projection 154 may be formed integrally with the distal portion of the ultrasonic transmission waveguide 152 or may fixedly mounted thereto.

The distal portion of the ultrasonic transmission waveguide 152 comprises a plurality of the stabilizing silicone rings or compliant supports 56 positioned at a plurality of nodes. The silicone rings 56 dampen undesirable vibration and isolate the ultrasonic energy from the outer tube 150 assuring the flow of ultrasonic energy in a longitudinal direction to the distal end 52 of the end effector 50 with maximum efficiency.

The transition portion 126, the proximal shaft 138, the proximal stop 140, and the distal portion of the ultrasonic transmission waveguide 152 may be formed as a single unitary piece or may be removably attached to each other. The transition portion 126, the proximal shaft 138, the proximal stop 140, and the distal portion of the ultrasonic transmission waveguide 152 form an ultrasonic transmission waveguide that may be tuned and coupled to the surface 30 of the hand piece assembly 60 to amplify the amplitude of the mechanical vibrations generated by the ultrasonic transducer 14 as discussed with reference to FIG. 1. The ultrasonic instrument 120 may be tuned such that the mechanical displacements caused by the ultrasonic vibrations are efficiently transferred from the ultrasonic transducer 14 to the end effector 50 such that the effector experiences axial longitudinal displacements.

The slap hammer 136 is slideably movable over the proximal shaft 138 in the direction indicated by arrow 142. The slap hammer 136 comprises a gripping surface 158 and a sliding weight 160 that travels axially in line with the end effector 50. When the slap hammer 136 is moved axially towards the distal end 122, a circumferential distal surface 144 of the slap hammer 136 impacts a proximal surface 146 of the proximal stop 140. The proximal surface 146 defines an area to receive vibratory energy in the form of mechanical impacts. The resulting impacts are transmitted through the ultrasonic transmission waveguide 152 to drive the end effector 50 at the distal end 122 into the musculoskeletal tissue to effect treatment. The sliding weight 160 assists in imparting energy upon impact. The circumferential proximal surface 146 forms an impact zone.

In use, a clinician may employ the ultrasonic hand piece assembly 60 coupled to the ultrasonic instrument 120 to effect musculoskeletal tissue. In one phase the end effector 50 may be operated ultrasonically (e.g., powered state). In this manner, the clinician holds the handpiece housing 16 of the handpiece assembly 60 with one hand and may hold either the slap hammer 136 or the grip 148 portions and employs substantially the energy generated by the ultrasonic transducer 14 for tissue effects. In another phase, the clinician may hold the grip 148 with one hand and slideably move the slap hammer 136 axially in the direction indicated by arrow 142 to impact the distal surface 144 of the weighted slap hammer 136 against the proximal surface 146 of the proximal stop 140. This action imparts a driving force or energy the end effector 50. The slap hammer 136 may be manually operated either with or without the assistance of the ultrasonic vibrations. For example, the slap hammer 136 may be employed with the ultrasonic hand piece assembly 60 either in a powered or unpowered state.

Figure 6:
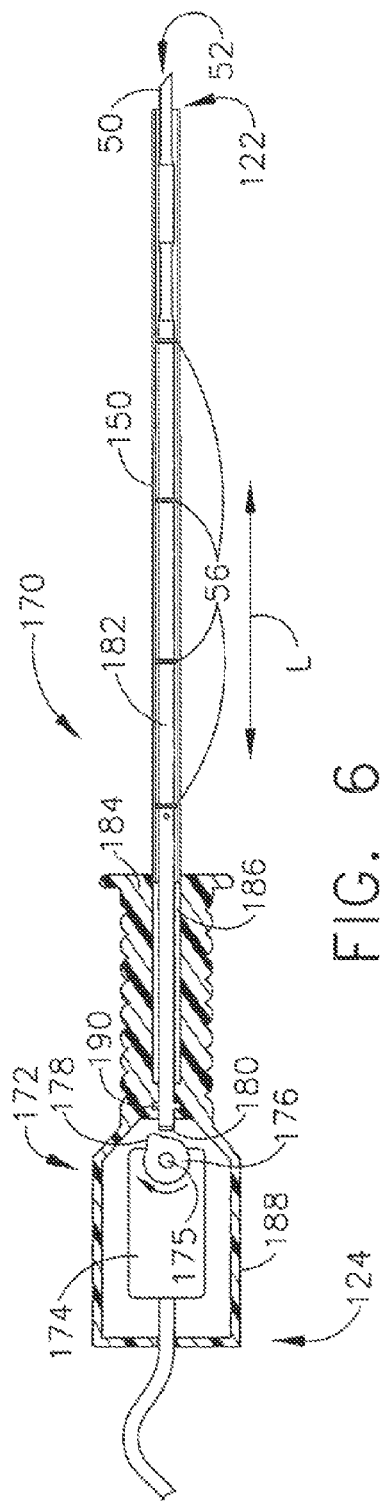
FIG. 6 is a cross-sectional view of one embodiment of an vibrational surgical instrument taken along the longitudinal axis "L".

FIG. 6 is a cross-sectional view of one embodiment of an vibrational surgical instrument 170 taken along the longitudinal axis "L". In the illustrated embodiment, the vibrational surgical instrument 170 comprises an end effector 50 that is well-suited for effecting (e.g., cutting, coagulating, drilling) musculoskeletal tissue comprising bones, muscles, joints, and the associated periarticular tissues such as tendons, ligaments, cartilage, joints, and spinal discs. As previously discussed, the end effector 50 may have a chisel like shape adapted to cut bone or may have a rounded end adapted to drill small holes in bone. The vibrational surgical instrument 170 comprises a distal end 122 and a proximal end 124 and defines a longitudinal axis "L".

The proximal end 124 comprises a handpiece assembly 172. A housing 188 contains a generator 174 to drive a rotating cam 176 comprising a lobe 178. In the illustrated embodiment, the hand piece assembly 172 does not comprise a piezoelectric transducer to generate the ultrasonic vibrations. The generator 174 generates longitudinal vibrational displacement by mechanical action without the use of piezoelectric transducers. In one embodiment, the generator 174 produces longitudinal mechanical vibrations of various predetermined frequencies by driving the cam 176 about a hub 175. The lobe 178 may be configured as any suitable projecting part of the rotating cam 176 to strike or mechanically communicate with a surface 180 of a vibrational transmission waveguide 182 at one or more points on its circular path. The surface 180 has an area configured to receive vibratory energy in the form of mechanical impacts. The lobe 178 imparts vibratory energy into the vibrational transmission waveguide 182. The vibrational transmission waveguide 182 acts as a follower. This produces a smooth axial oscillating motion in the vibrational transmission waveguide 182 that makes contact with the lobe 178 via the surface 180. The lobe 178 may be a simple rounded smooth projection to deliver pulses of power to the surface 180 of the vibrational transmission waveguide 182. In alternative embodiments, the lobe 178 may be an eccentric disc or other shape that produces a smooth oscillating motion in the vibrational transmission waveguide 182 follower which is a lever making contact with the lobe 178. Accordingly, the lobe 178 translates the circular motion of the cam 176 to linear displacements creating longitudinal the oscillations or vibrations that are efficiently transferred to the distal end 52 of the end effector 50 by the vibrational transmission waveguide 182. Accordingly, the distal end 52 of the end effector 50 experiences longitudinal displacements to effect tissue. The generator 174 may employ either an electric, hydraulic, or pneumatic motor to drive the cam 176 about the hub 175. Those skilled in the art will appreciate that a hydraulic motor uses a high pressure water jet to turn a shaft coupled to the cam 176 about the hub 175.

The vibrational transmission waveguide 182 may be positioned inside a handle portion or grip 184 over a sleeve 186. The vibrational transmission waveguide 182 may be retained within the grip 184 and may be fixedly mounted by a ring or circumferential projection 190. The circumferential projection 190 may be formed integrally with the distal portion of the vibrational transmission waveguide 182 or may be fixedly mounted thereto. In principle, the vibrational transmission waveguide 182 operates in a manner similar to the ultrasonic transmission waveguide 46 discussed in FIG. 1. The vibrational transmission waveguide 182, however, may be tuned to amplify and transmit longitudinal vibrations at frequencies that may be suitably or practically achieved with the rotating cam 176 and lobe 178 arrangement. Nevertheless, it is contemplated that the vibrational transmission waveguide 182 may be driven at ultrasonic frequencies. As previously discussed, a suitable vibrational frequency range may be about 20 Hz to 120 kHz and a well-suited vibrational frequency range may be about 30-70 kHz and one example operational vibrational frequency may be approximately 55.5 kHz.

The vibrational transmission waveguide 182 is positioned within the longitudinal opening defined through the outer tube 150. The vibrational transmission waveguide 182 comprises a plurality of stabilizing silicone rings or compliant supports 56 positioned at a plurality of nodes. The silicone rings 56 dampen undesirable vibration and isolate the ultrasonic energy from the outer tube 150 assuring the flow of vibrational energy in a longitudinal direction to the distal end 52 of the end effector 50 with maximum efficiency.

In use, a clinician may employ the vibrational surgical instrument 170 to effect musculoskeletal tissue. The end effector 50 is positioned at the desired tissue treatment region within a patient. The clinician holds the grip 184 portion and manipulates the end effector 50 to treat the musculoskeletal tissue. The vibrations generated by the rotating cam 176 and lobe 178 arrangement are efficiently transferred to the distal end 52 of the end effector 50 by the vibrational transmission waveguide 182. Accordingly, the distal end 52 of the end effector 50 experiences longitudinal displacements to assist the tissue effects of cutting, coagulating, drilling tissue. Accordingly, the vibrational surgical instrument 170 enables the clinician to perform tissue effects on musculoskeletal tissue with more precision that may be achieved with a slap hammer alone or using an osteotome (e.g., bone chisel) and mallet. An osteotome is a wedge-like instrument used for cutting or marking bone often called a chisel and is used by a clinician with a mallet.

Figure 7:
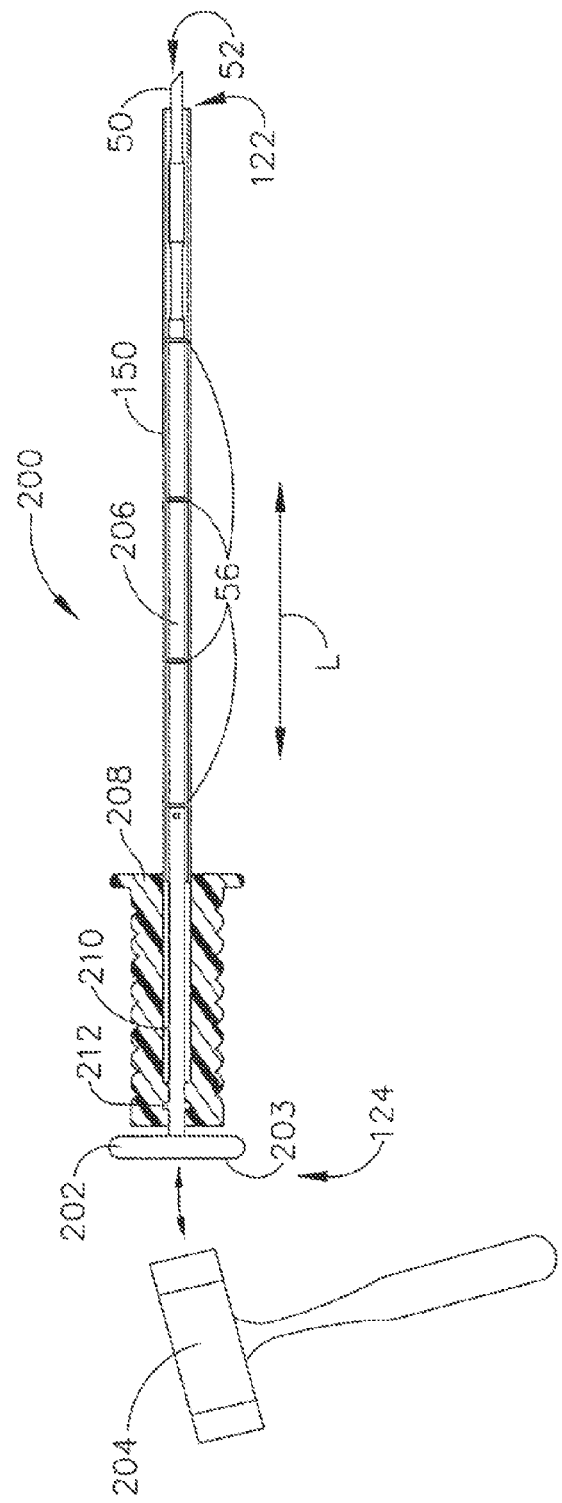
FIG. 7 is a cross-sectional view of one embodiment of a vibrational surgical instrument taken along the longitudinal axis "L".

FIG. 7 is a cross-sectional view of one embodiment of a vibrational surgical instrument 200 taken along the longitudinal axis "L". In the illustrated embodiment, the vibrational surgical instrument 200 comprises an end effector 50 that is well-suited for effecting (e.g., cutting, coagulating, drilling) musculoskeletal tissue comprising bones, muscles, joints, and the associated periarticular tissues such as tendons, ligaments, cartilage, joints, and spinal discs. As previously discussed, the end effector 50 may have a chisel like shape adapted to cut bone or may have a rounded end adapted to drill small holes. The vibrational surgical instrument 200 comprises a distal end 122 and a proximal end 124 and defines a longitudinal axis "L".

The vibrational surgical instrument 200 comprises a flange or strike plate 202 at the proximal end 124. The strike plate 202 defines a strikeable surface 203 having a flange area configured to receive vibratory energy in the form of mechanical impacts such as a mallet blow from an osteotome type mallet 204 and impart the resulting vibratory energy into the end effector 50. Striking the strike plate 202 with the mallet 204 generates a suitable vibrational resonance that may be sustained over time to mechanically displace the end effector 50 in accordance with the mechanical vibrations. The vibrational surgical instrument 200 comprises a vibrational transmission waveguide 206 positioned within an outer tubular member or outer tube 150. The vibrational transmission waveguide 206 comprises a plurality of stabilizing silicone rings or compliant supports 56 positioned at a plurality of nodes. The silicone rings 56 dampen undesirable vibration and isolate the ultrasonic energy from a removable sheath 150 assuring the flow of vibrational energy in a longitudinal direction to the distal end 52 of the end effector 50 with maximum efficiency.

The vibrational transmission waveguide 206 is positioned inside a handle portion or grip 208 over a sleeve 210 (e.g., bushing). The vibrational transmission waveguide 206 is retained within the grip 208 and is fixedly mounted by a ring or circumferential projection 212. The circumferential projection 212 may be formed integrally with the distal portion of the vibrational transmission waveguide 206 or may fixedly mounted thereto. In principle, the vibrational transmission waveguide 206 operates in a manner similar to the ultrasonic transmission waveguide 46 discussed above. The vibrational transmission waveguide 206 however may be tuned to amplify and transmit longitudinal vibrations at frequencies more suitably achievable with the osteotome type mallet 204 striking the strikeable surface 230 of the strike plate 202.

In use, a clinician may employ the vibrational surgical instrument 200 to effect musculoskeletal tissue. The end effector 50 is positioned at the desired tissue treatment region within a patient. The clinician holds the grip 208 portion with one hand and manipulates the end effector 50 to treat the musculoskeletal tissue. The vibrations generated by striking the strike plate 202 are efficiently transferred to the distal end 52 of the end effector 50, which experiences longitudinal displacements to assist in the tissue effect, to cut, coagulate, drill tissue. Accordingly, the vibrational surgical instrument 200 enables the clinician to perform tissue effects on musculoskeletal tissue with more precision that with using a slap hammer alone or using a bone chisel or tuned osteotome.

Figure 8:
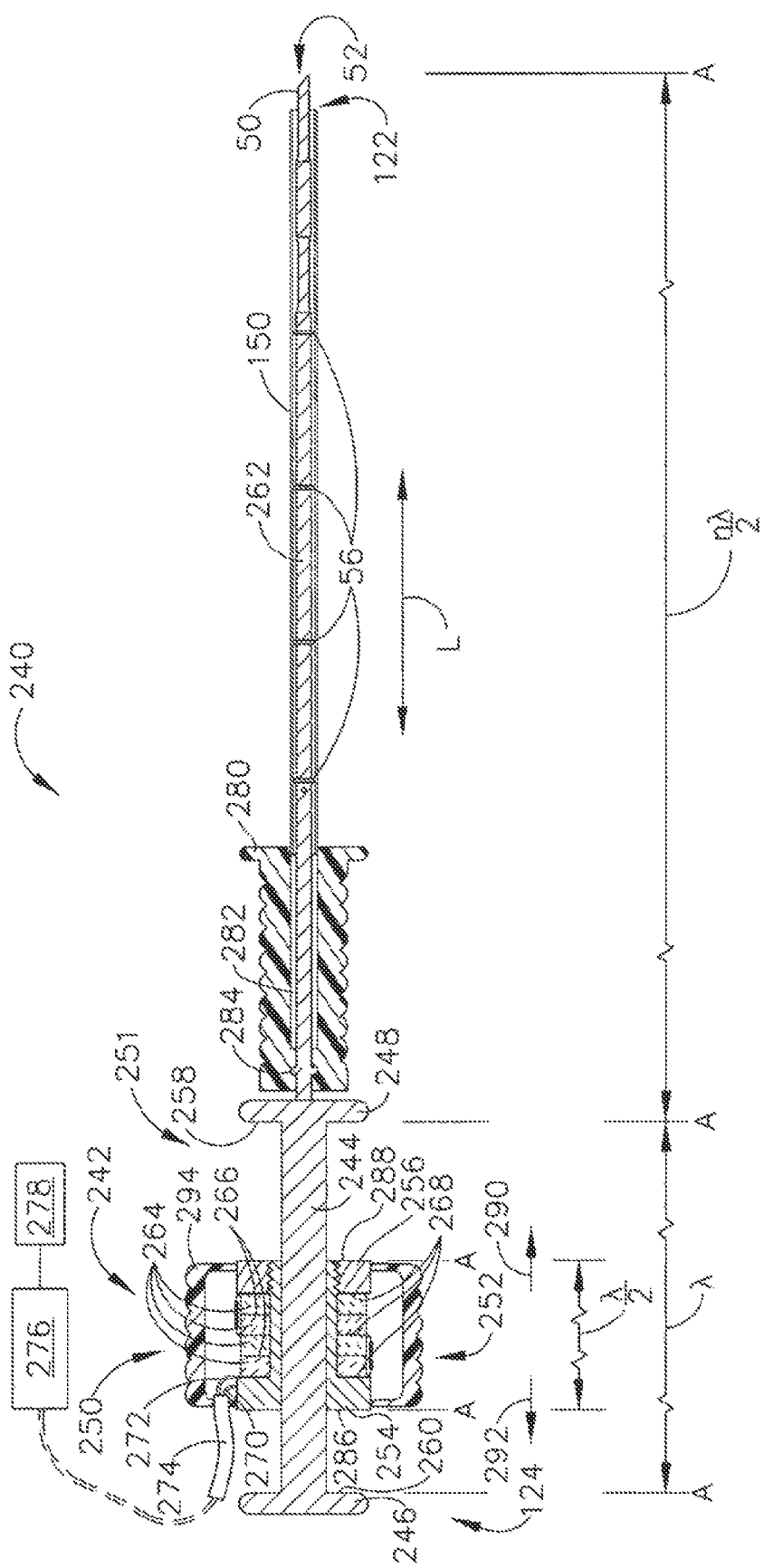
FIG. 8 is a cross-sectional view of one embodiment of an ultrasonic instrument taken along the longitudinal axis "L".

FIG. 8 is a cross-sectional view of one embodiment of an ultrasonic instrument 240 taken along the longitudinal axis "L". In the illustrated embodiment, the ultrasonic instrument 240 comprises an end effector 50 that is well-suited for effecting (e.g., cutting, coagulating, drilling) musculoskeletal tissue comprising bones, muscles, joints, and the associated periarticular tissues such as tendons, ligaments, cartilage, joints, and spinal discs. As previously discussed, the end effector 50 may have a chisel like shape adapted to cut bone or may have a rounded end adapted to drill small holes. The ultrasonic instrument 240 comprises a distal end 122 and a proximal end 124 and defines a longitudinal axis "L". The ultrasonic instrument 240 may be employed as an ultrasonic osteo-hammer to help drive cutting instruments and other hardware such as "trial" devices into musculoskeletal tissue such as bone. In various other embodiments, however, the ultrasonic instrument 240 may be employed in combination with an ultrasonic end effector 50 comprising conventional ultrasonic blades for cutting, coagulating, and/or reshaping tissue. In the embodiment illustrated in FIG. 8, the ultrasonic instrument 240 may be employed to drive the end effector 50 into tissue or force distraction, e.g., separation of bony fragments or joint surfaces of a limb, and also may be employed to remove instruments that may be tightly wedged. The ultrasonic instrument 240 increases efficiency and speed during a procedure while providing more accuracy that a manually operated osteotome.

The ultrasonic instrument 240 comprises an ultrasonic slide hammer 242 at the proximal end 124. The ultrasonic slide hammer 242 is slideably movable over a proximal shaft 244 between a first flange or proximal stop 246 and a second flange or distal stop 248 in the directions indicated by arrows 290, 292. The ultrasonic slide hammer 242 comprises an ultrasonic transducer 250, which is known as a "Langevin stack", and generally includes a transduction portion 252, a first resonator or end-bell 254, and a second resonator or fore-bell 256, and ancillary components. In the illustrated embodiment, the ultrasonic transducer 250 is the moving mass of the ultrasonic slide hammer 242. The ultrasonic transducer 250 is preferably an integral number of one-half system wavelengths ($n\lambda/2$) in length as previously discussed with reference to the ultrasonic system 10 in FIG. 1. An acoustic assembly 251 is formed by the ultrasonic transducer 250, the proximal shaft 244, the proximal stop 246, and the distal stop 248. In the illustrated embodiment, the length of the ultrasonic transducer 250 is $\lambda/2$ and the length of the proximal shaft 244 is at least $1\lambda$ as illustrated, with antinodes generally indicated at "A" (e.g., where axial displacement is usually maximal) being formed at the distal and proximal ends of the proximal shaft 244. The proximal shaft 244 may be made longer. Nevertheless, the length of the proximal shaft 244 should be an integer multiple of half-wavelengths ($n\lambda/2$) and should be at least one-half wavelength ($\lambda/2$) longer than the ultrasonic transducer 250. The length of the ultrasonic instrument 240 from the distal end of the proximal shaft 244 to the distal end 52 of the end effector 50 should be an integer multiple of one-half system wavelengths ($n\lambda/2$). These relationships are explained in more detail below.

The distal end of the end-bell 254 is connected to the proximal end of the transduction portion 252, and the proximal end of the fore-bell 256 is connected to the distal end of the transduction portion 252. The fore-bell 256 and the end-bell 254 have a length determined by a number of variables, including the thickness of the transduction portion 252, the density and modulus of elasticity of the material used to manufacture the end-bell 254 and the fore-bell 256, and the resonant frequency of the ultrasonic transducer 250. The ultrasonic transducer 250 creates impacts or vibrations at ultrasonic frequencies and imparts stress waves that are coupled to an ultrasonic transmission waveguide 262 to advance (e.g., drive) or remove (e.g., retract) the ultrasonic instrument 240. A distal surface of the fore-bell 256 acts a driving platen 288 when it is driven or coupled to a distal striking platen 258 formed by the proximal surface of the distal stop 248. The surface of the distal striking platen 258 has an area configured to receive vibratory energy in the form of vibrations and impart the vibratory energy into the end effector 50. The surface of the driving platen 288 is located at an anti-node "A". When the driving platen 288 is coupled to the distal striking platen 258, ultrasonic vibrations generated by the ultrasonic transducer 250 are coupled through the ultrasonic transmission waveguide 262 and create impacts to drive the ultrasonic instrument 240 into tissue at the distal end 122 in the direction indicated by arrow 290. A proximal surface of the end-bell 254 acts as a removing platen 286 when it is driven or coupled to a proximal striking platen 260 formed by the distal surface of the proximal stop 246. The surface of the distal striking platen 260 has an area configured to receive vibratory energy in the form of vibrations and impart the vibratory energy into the proximal stop 246. The surface of the removing platen 286 is located at an anti-node "A". When the removing platen 286 is coupled to the proximal striking platen 260, ultrasonic vibrations generated by the ultrasonic transducer 250 are coupled into the proximal stop 246 and create impacts to retract the ultrasonic instrument 240 in the proximal directions from the tissue in the direction indicated by arrow 292. A suitable vibrational frequency range for the ultrasonic slide hammer 242 may be about 20 Hz to 120 kHz and a well-suited vibrational frequency range may be about 30-70 kHz and one example operational vibrational frequency may be approximately 55.5 kHz. As a general rule, lower frequencies tend to provide more power capability. In one embodiment, the ultrasonic transducer 250 does not couple to the end effector 50, but rather creates a vibratory "jackhammer".

Piezoelectric elements 264 may be fabricated from any suitable material, such as, for example, lead zirconate-titanate, lead meta-niobate, lead titanate, or other piezoelectric crystal material. Each of positive electrodes 266, negative electrodes 268, and piezoelectric elements 264 has a bore extending through the center. The positive and negative electrodes 266 and 268 are electrically coupled to wires 272 and 270, respectively. The wires 270, 272 are encased within a cable 274 and electrically connectable to an ultrasonic signal generator 276.

The ultrasonic transducer 250 converts the electrical signal from the ultrasonic signal generator 276 into mechanical energy that results in primarily longitudinal vibratory motion of the ultrasonic transducer 250 and the end effector 50 at ultrasonic frequencies. A suitable generator is available as model number GEN04, from Ethicon Endo-Surgery, Inc., Cincinnati, Ohio. When the acoustic assembly 251 is energized, a vibratory motion standing wave is generated through the acoustic assembly 251. The amplitude of the vibratory motion at any point along the acoustic assembly 251 may depend upon the location along the acoustic assembly 251 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node (i.e., where motion is usually maximal). The distance between an anti-node and its nearest node is one-quarter wavelength ($\lambda/4$).

The wires 270 and 272 transmit an electrical signal from the ultrasonic signal generator 276 to the respective positive electrodes 268 and the negative electrodes 266. The piezoelectric elements 264 are energized by the electrical signal supplied from the ultrasonic signal generator 264 in response to a foot switch 278 to produce an acoustic standing wave in the acoustic assembly 251. The electrical signal causes disturbances in the piezoelectric elements 264 in the form of repeated small displacements resulting in large compression forces within the material. The repeated small displacements cause the piezoelectric elements 264 to expand and contract in a continuous manner along the axis of the voltage gradient, producing longitudinal waves of ultrasonic energy. The ultrasonic energy is transmitted through the acoustic assembly 251 to the end effector 50 via the ultrasonic transmission waveguide 262. In order for the acoustic assembly 251 to deliver energy to the end effector 50, all components of the acoustic assembly 251 must be acoustically coupled to the end effector 50. In one mode of operation, the distal end 52 of the ultrasonic transducer 250 may be acoustically coupled to the proximal surface 258 of the distal stop 248 and to the ultrasonic transmission waveguide 262. In another mode of operation, the proximal end of the ultrasonic transducer 250 may be acoustically coupled to the distal surface 260 of the proximal stop 246 and to ultrasonic transmission waveguide 262 through the proximal shaft 244.

The components of the acoustic assembly 251 are preferably acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of the acoustic assembly 251, and where n is any positive integer. It is also contemplated that the acoustic assembly 251 may incorporate any suitable arrangement of acoustic elements.

The ultrasonic end effector 50 may have a length substantially equal to an integral multiple of one-half system wavelengths ($\lambda/2$). The distal end 52 of the ultrasonic end effector 50 may be disposed near an antinode "A" in order to provide the maximum longitudinal excursion of the distal end 52. When the ultrasonic transducer 250 is energized and the vibrations are coupled to the end effector 50 via the ultrasonic transmission waveguide 262, the distal end 52 of the ultrasonic end effector 50 may be configured to move in the range of, for example, approximately 10 to 500 microns peak-to-peak, and preferably in the range of about 30 to 150 microns at a predetermined vibrational frequency.

The ultrasonic end effector 50 may be coupled to the ultrasonic transmission waveguide 262. In the illustrated embodiment, the ultrasonic end effector 50, the ultrasonic transmission guide 262, the proximal and distal stops 246, 248, and the proximal shaft 244 are formed as a single unit construction from a material suitable for transmission of ultrasonic energy such as, for example, Ti6Al4V (an alloy of Titanium including Aluminum and Vanadium), Aluminum, Stainless Steel, or other known materials. Alternately, the ultrasonic end effector 50 may be separable (and of differing composition) from the ultrasonic transmission waveguide 262, and coupled by, for example, a stud, weld, glue, quick connect, or other suitable known methods. The ultrasonic transmission waveguide 262 may have a length substantially equal to an integral number n of one-half system wavelengths ($n\lambda/2$), for example. The ultrasonic transmission waveguide 262 may be preferably fabricated from a solid core shaft constructed out of material that propagates ultrasonic energy efficiently, such as titanium alloy (i.e., Ti-6Al-4V) or an aluminum alloy, for example. In the illustrated embodiment, the ultrasonic transmission waveguide 262 comprises a plurality of stabilizing silicone rings or compliant supports 56 positioned at a plurality of nodes. The silicone rings 56 dampen undesirable vibration and isolate the ultrasonic energy from the outer tube 150 assuring that the ultrasonic energy flows axially in a longitudinal direction "L" to the distal end 52 of the end effector 50 with maximum efficiency.

In alternative embodiments, the distal end of the distal stop 248 may be configured with an attachment feature such as a threaded connection to couple the ultrasonic transmission waveguide 262 or other ultrasonic (e.g., orthopedic) instruments with a stud. In other embodiments, the distal end of the distal stop 248 may be configured with a longitudinally projecting attachment post to couple to the ultrasonic transmission waveguide 262 or other ultrasonic instruments thereto. In other embodiments, the ultrasonic transmission waveguide 262 or other ultrasonic instruments may be attached to the distal end of the distal stop 248 by a weld, glue, quick connect, or other suitable known methods.

In use, a clinician can operate the ultrasonic instrument 240 in a driving mode and a retracting mode. In the illustrated embodiment, the ultrasonic slide hammer 242 is configured with a cylindrical grip 294 for the clinician to hold. In a driving mode, the ultrasonic slide hammer 242 is moved in the direction indicated by arrow 290 to drive the ultrasonic instrument 240 into tissue. In a retracting mode, the ultrasonic slide hammer 242 in the direction indicated by arrow 292 to retract the ultrasonic instrument 240. In alternative embodiments, the ultrasonic slide hammer 242 may be configured with a pistol-like grip so the clinician can hold the ultrasonic slide hammer 242 more-like a power drill, for example. When the driving platen 288 is forced in the direction indicated by arrow 290 into the distal striking platen 258, the ultrasonic transducer 250 creates impacts that are coupled by the ultrasonic transmission waveguide 262 to the end effector 50 to impart stress waves in the tissue being treated. Because the driving platen 288 and the distal striking platen 258 are both located at anti-nodes "A" a clinician needs only to apply enough load to force the driving platen 288 into the distal striking platen 258 together. At an anti-node "A" there is little vibrational stress so minimal vibrations are transferred to the hand of the clinician. The clinician applies a force until the desired effect is achieved.

The ultrasonic instrument 240 may comprise an optional grip 280 positioned distally beyond the proximal stop 248 over a proximal sleeve 282. The grip 280 is fixedly mounted to the ultrasonic transmission waveguide 262 by a ring or circumferential projection 284. The circumferential projection 284 may be formed integrally with the distal portion of the ultrasonic transmission waveguide 262 or may fixedly mounted thereto. The grip 280 provides an additional handle for a clinician to hold during a procedure to help support and guide the ultrasonic instrument 240.

Figure 9:
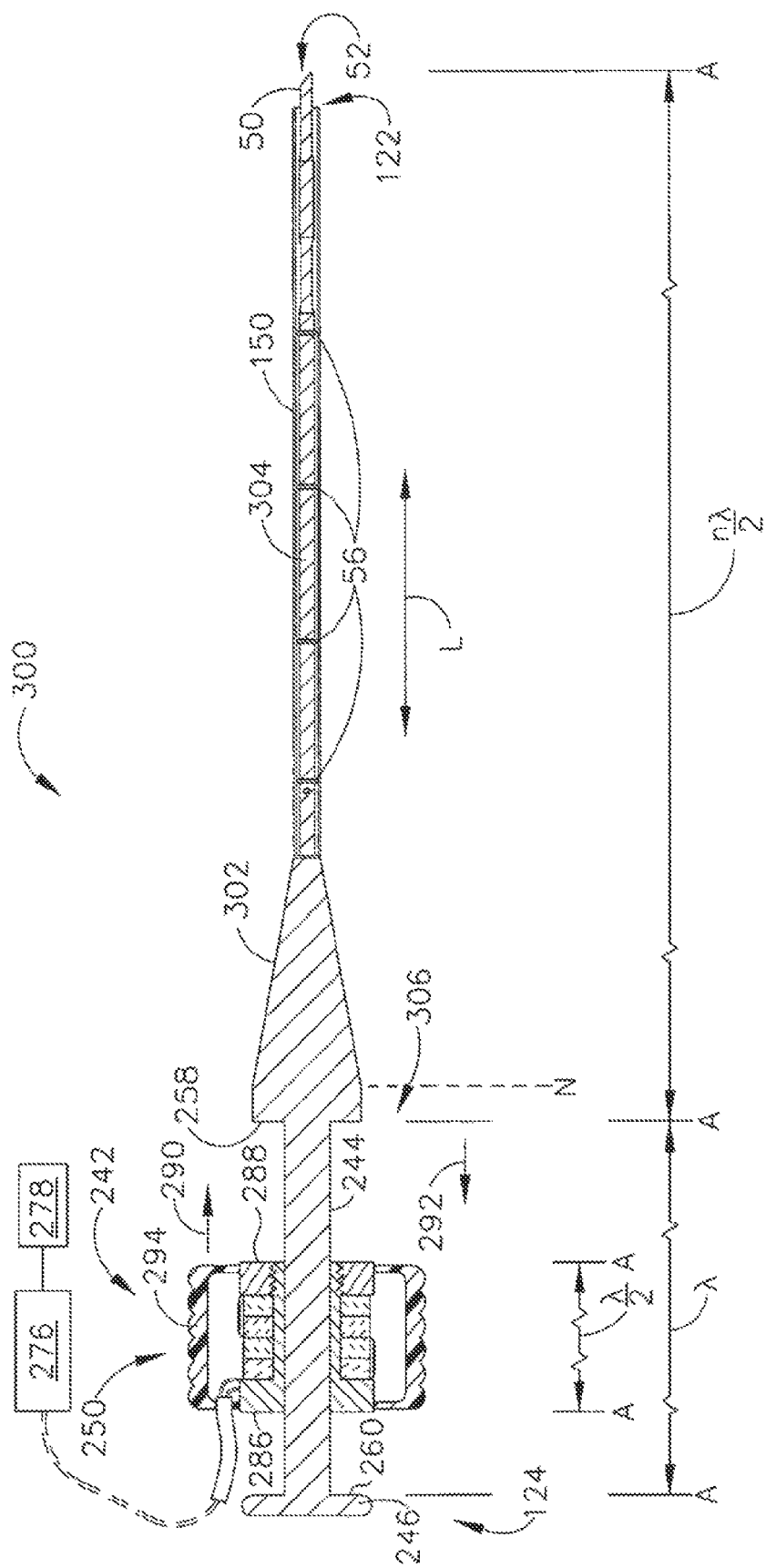
FIG. 9 is a cross-sectional view of one embodiment of an ultrasonic instrument taken along the longitudinal axis "L".

FIG. 9 is a cross-sectional view of one embodiment of an ultrasonic instrument 300 taken along the longitudinal axis "L". In the illustrated embodiment, the ultrasonic instrument 300 comprises an end effector 50 that is well-suited for effecting (e.g., cutting, coagulating, drilling) musculoskeletal tissue comprising bones, muscles, joints, and the associated periarticular tissues such as tendons, ligaments, cartilage, joints, and spinal discs, as previously discussed. The ultrasonic instrument 300 comprises a distal end 122 and a proximal end 124 and defines a longitudinal axis "L". The ultrasonic instrument 300 may be employed as an ultrasonic osteo-hammer to help drive cutting instruments and other hardware such as "trial" devices into tissue. The ultrasonic instrument 300 may be employed to drive into tissue or force distraction and also may be employed to remove instruments that may be tightly wedged. The ultrasonic instrument 300 increases efficiency and speed during a procedure while providing more accuracy that a manually operated osteotome.

The ultrasonic instrument 300 comprises an ultrasonic slide hammer 242 at the proximal end 124 substantially as described with reference to FIG. 8. The ultrasonic slide hammer 242 is slideably movable over a proximal shaft 244 between a first flange or proximal stop 246 and a second flange or distal stop 302 in the directions indicated by arrows 290, 292. In the illustrated embodiment, the distal stop 302 has a generally frustoconical shape and is tapered inwardly from a proximal end to a distal end to amplify the ultrasonic vibration amplitude generated by the ultrasonic transducer 250. As shown in the embodiment illustrated in FIG. 9, the conical transition occurs at a node "N". The ultrasonic slide hammer 242 comprises an ultrasonic transducer 250, as previously discussed with reference to FIG. 8. In the illustrated embodiment, the ultrasonic transducer 250 is the moving mass of the ultrasonic slide hammer 242. The ultrasonic transducer 250 is preferably an integral number of one-half system wavelengths (n$\lambda$/2) in length as previously discussed with reference to the ultrasonic system 10 in FIG. 1. An acoustic assembly 306 is formed by the ultrasonic transducer 250, the proximal shaft 244, and either one of the proximal stop 246 or the distal stop 302. In the illustrated embodiment, the length of the ultrasonic transducer 250 is $\lambda$/2 and the length of the proximal shaft 244 is $\lambda$, with anti-nodes generally indicated at "A" (e.g., where axial displacement is usually maximal) being formed at the distal and proximal ends of the proximal shaft 244. The length of the ultrasonic instrument 300 from the distal end of the proximal shaft 244 to the distal end 52 of the end effector 50 should be an integer multiple of one-half system wavelengths (n$\lambda$/2). These relationships were explained in more detail above with reference to FIG. 8.

As previously discussed, the ultrasonic transducer 250 creates impacts or vibrations at ultrasonic frequencies and imparts stress waves that are coupled by an ultrasonic transmission waveguide 304 to advance (e.g., drive) or remove (e.g., retract) the ultrasonic instrument 300. A distal driving platen 288 is driven or coupled to a distal striking platen 258 formed by the proximal surface of the distal stop 302 when the ultrasonic slide hammer 242 is moved in the direction indicated by arrow 290. The surface of the driving platen 288 is located at an anti-node "A". When the driving platen 288 is coupled to the distal striking platen 258, ultrasonic vibrations generated by the ultrasonic transducer 250 are coupled through the ultrasonic transmission waveguide 304 and creates impacts to drive the ultrasonic instrument 300 into tissue at the distal end 122 in the direction indicated by arrow 290. A proximal removing platen 286 is driven or coupled to a proximal striking platen 260 formed by the distal surface of the proximal stop 246 when the ultrasonic slide hammer 242 is moved in the direction indicated by arrow 292. The surface of the removing platen 286 is located at an anti-node "A". When the removing platen 286 is coupled to the proximal striking platen 260, ultrasonic vibrations generated by the ultrasonic transducer 250 are coupled into the proximal stop 246 and creates impacts to retract the ultrasonic instrument 300 in the proximal direction from the tissue in the direction indicated by arrow 292. As previously discussed, the distal stop 302 amplifies the amplitude of the ultrasonic vibrations generated by the ultrasonic transducer 250. A suitable vibrational frequency range for the ultrasonic slide hammer 242 may be about 20 Hz to 120 kHz and a well-suited vibrational frequency range may be about 30-70 kHz and one example operational vibrational frequency may be approximately 55.5 kHz. As a general rule, lower frequencies tend to provide more power capability.

The ultrasonic transducer 250 converts the electrical signal from the ultrasonic signal generator 276 into mechanical energy that results in primarily longitudinal vibratory motion of the ultrasonic transducer 250 and the end effector 50 at ultrasonic frequencies. When the acoustic assembly 306 is energized, a vibratory motion standing wave is generated through the acoustic assembly 306. The amplitude of the vibratory motion at any point along the acoustic assembly 306 may depend upon the location along the acoustic assembly 306 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node (i.e., where motion is usually maximal). The distance between an anti-node and its nearest node is one-quarter wavelength ($\lambda$/4).

The ultrasonic transducer 250 is energized by the electrical signal supplied from the ultrasonic signal generator 264 in response to a foot switch 278 to produce an acoustic standing wave in the acoustic assembly 306. The ultrasonic energy is transmitted through the acoustic assembly 306 to the end effector 50 via an ultrasonic transmission waveguide 304. In order for the acoustic assembly 306 to deliver energy to the end effector 50, all components of the acoustic assembly 306 must be acoustically coupled to the end effector 50. In one mode of operation, the distal end of the ultrasonic transducer 250 may be acoustically coupled to the distal striking platen 258, amplified by the distal stop 302 element, and to the ultrasonic transmission waveguide 304. In another mode of operation, the proximal end of the ultrasonic transducer 250 may be acoustically coupled to the proximal striking platen 260 through the ultrasonic transmission waveguide 304 and through the proximal shaft 244.

The components of the acoustic assembly 306 are preferably acoustically tuned such that the length of any assembly is an integral number of one-half wavelengths (n$\lambda$/2), where the wavelength $\lambda$ is the wavelength of a pre-selected or operating longitudinal vibration drive frequency $f_d$ of the acoustic assembly 306, and where n is any positive integer. It is also contemplated that the acoustic assembly 306 may incorporate any suitable arrangement of acoustic elements.

The ultrasonic end effector 50 may have a length substantially equal to an integral multiple of one-half system wavelengths ($\lambda$/2). The distal end 52 of the ultrasonic end effector 50 may be disposed near an antinode in order to provide the maximum longitudinal excursion of the distal end. When the ultrasonic transducer 250 is energized and the vibrations are coupled to the end effector 50 via the ultrasonic transmission waveguide 304, the distal end 52 of the ultrasonic end effector 50 may be configured to move in the range of, for example, approximately 10 to 500 microns peak-to-peak, and preferably in the range of about 30 to 150 microns at a predetermined vibrational frequency.

The ultrasonic end effector 50 may be coupled to the ultrasonic transmission waveguide 304. In the illustrated embodiment, the ultrasonic end effector 50, the ultrasonic transmission guide 304, the proximal and distal stops 246, 302, and the proximal shaft 244 are formed as a single unit construction from a material suitable for transmission of ultrasonic energy such as, for example, Ti6Al4V (an alloy of Titanium including Aluminum and Vanadium), Aluminum, Stainless Steel, or other known materials. Alternately, the ultrasonic end effector 50 may be separable (and of differing composition) from the ultrasonic transmission waveguide 304, and coupled by, for example, a stud, weld, glue, quick connect, or other suitable known methods. The ultrasonic transmission waveguide 304 may have a length substantially equal to an integral number n of one-half system wavelengths (n$\lambda$/2), for example. The ultrasonic transmission waveguide 304 may be preferably fabricated from a solid core shaft constructed out of material that propagates ultrasonic energy efficiently, such as titanium alloy (i.e., Ti-6Al-4V) or an aluminum alloy, for example. In the illustrated embodiment, the ultrasonic transmission waveguide 304 comprises a plurality of stabilizing silicone rings or compliant supports 56 positioned at a plurality of nodes. The silicone rings 56 dampen undesirable vibration and isolate the ultrasonic energy from a removable sheath or outer tube 150 assuring the flow of ultrasonic energy axially in a longitudinal direction "L" to the distal end 52 of the end effector 50 with maximum efficiency.

In alternative embodiments, the distal end of the distal stop 302 may be configured with an attachment feature such as a threaded connection to couple the ultrasonic transmission waveguide 304 or other ultrasonic (e.g., orthopedic) instruments with a stud. In other embodiments, the distal end of the distal stop 302 may be configured with a longitudinally projecting attachment post to couple to the ultrasonic transmission waveguide 304 or other ultrasonic instruments thereto. In other embodiments, the ultrasonic transmission waveguide 304 or other ultrasonic instruments may be attached to the distal end of the distal stop 302 by a weld, glue, quick connect, or other suitable known methods.

In use, a clinician can operate the ultrasonic instrument 300 in a substantially similar manner as previously described with reference to FIG. 8. In the illustrated embodiment, the ultrasonic slide hammer 242 is configured with a cylindrical grip 294 so the clinician can hold the ultrasonic slide hammer 242 while moving it. To drive the ultrasonic instrument 300, the clinician moves the ultrasonic slide hammer 242 in the direction indicated by arrow 290. To retract the ultrasonic instrument 300, the clinician moves the slide hammer 242 in the direction indicated by arrow 292. In alternative embodiments, the ultrasonic slide hammer 242 may be configured with a pistol-like grip so the clinician can hold the ultrasonic slide hammer 242 more-like a power drill, for example. When the driving platen 288 is forced in the direction indicated by arrow 290 into the distal striking platen 258, the ultrasonic transducer 250 creates impacts that are coupled by the ultrasonic transmission waveguide 304 to the end effector 50 to impart stress waves in the tissue being treated. Because the driving platen 288 and the distal striking platen 258 are both located at anti-nodes "A" a clinician needs only to apply enough load to force the driving platen 288 into the distal striking platen 258 together. At an anti-node "A" there is little vibrational stress so minimal vibrations are transferred to the hand of the clinician. The clinician applies the force until the desired effect is achieved.

With reference to the ultrasonic instruments 240, 300 illustrated in FIGS. 8 and 9, in order to drive into tissue, the distal end 52 of the end effector 50 must overcome the failure limit of the tissue. In a simple model, this may be represented as the tissue reaction force and is a measure of the force necessary at the distal end 52 of the end effector 50 acting normal to the tissue (e.g., bone) to penetrate the tissue. The ultrasonic force required at the tissue surface to overcome the failure limit of the tissue may be expressed in simplified form as the tissue reaction force $F_t$:

$$F_t = k \cdot x + c \cdot x + d \cdot x^2 \quad (1)$$

Where
k=is the elastic component of the tissue;
c=the frictional component of the tissue; and
d=the hydraulic drag component of the tissue.

FIG. 10 illustrates a side view of one embodiment of an ultrasonic instrument 310 comprising an impact zone. In the illustrated embodiment, the ultrasonic instrument 310 extends longitudinally along axis "L" between a distal end 122 and a proximal end 124. In one embodiment, the ultrasonic instrument 310 comprises an ultrasonic hand piece assembly 312. Ultrasonically, the hand piece assembly 312 is substantially similar to and operates in substantially the same manner as the ultrasonic handpiece assembly 60 described in FIG. 1. The ultrasonic instrument 310 comprises a housing 314, a transduction portion 18, and an acoustic assembly 24 portion, as previously discussed with reference to FIG. 1. In one embodiment, the housing 314 comprises a substantially circular cross-section (not shown). The ultrasonic instrument 310 comprises the outer sheath 58 containing an ultrasonic transmission waveguide 46 (as previously discussed in FIG. 1) coupled to the end effector 50. In the illustrated embodiment, the end effector 50 has a chisel shape. A power cable 42 couples the ultrasonic handpiece assembly 312 to an ultrasonic generator (e.g., ultrasonic generator 12 shown in FIG. 1).

In one embodiment, the ultrasonic instrument 310 comprises a strike plate assembly 316. The strike plate assembly 316 comprises a flange or strike plate 318 defining a strikeable surface 320 having a flange area configured to receive or accommodate a mechanical impact and impart energy into the end effector 50 when the hand piece assembly 312 is in a powered or an unpowered state. The mechanical impact or strike may be delivered manually or with an osteotome mallet, for example. The strike plate 318 is suitable to receive a typical blow or strike from an osteotome mallet (e.g., similar to the mallet 204 shown in FIG. 7) at the strikeable surface 320 without damaging the ultrasonic hand piece assembly 312. In the illustrated embodiment, the strike plate assembly 316 comprises multiple longitudinally extending elongate support members 322 rigidly coupled to the strike plate 318 at a proximal end and fixedly coupled to the housing 314 at a distal end. In one embodiment, the housing 314 and the strike plate assembly 318 may be formed as a single unitary piece. In alternative embodiments, the housing 314 and the strike plate assembly 318 may be attached, coupled, or joined by, for example, stud, weld, glue, quick connect, or other suitable known methods.

In use, a clinician may employ the ultrasonic instrument 310 in a powered state using the ultrasonic vibrations generated by the transduction portion 18 to cut and coagulate relatively soft musculoskeletal tissue using the chisel shaped end effector 50. With the ultrasonic instrument 310 in a powered or an unpowered state, the clinician can employ an osteotome mallet to strike the strikeable surface 320 to chisel relatively hard musculoskeletal tissue such as bone.

FIG. 11 illustrates a side view of one embodiment of an ultrasonic instrument 330 comprising an impact zone. In the illustrated embodiment, the ultrasonic instrument 330 extends longitudinally along axis "L" between a distal end 122 and a proximal end 124. In one embodiment, the ultrasonic instrument 330 comprises an ultrasonic hand piece assembly 332. Ultrasonically, the hand piece assembly 332 is substantially similar to and operates in substantially the same manner as the handpiece assembly 60 described in FIG. 1. The ultrasonic instrument 330 comprises a housing 334, a transduction portion 18, and an acoustic assembly 24 portion, as previously discussed with reference to FIG. 1. In one embodiment, the housing 334 comprises a substantially circular cross-section (not shown). The ultrasonic instrument 330 comprises the sheath 58 containing the ultrasonic transmission waveguide 46 therein (as previously discussed in FIG. 1) coupled to the end effector 50. In the illustrated embodiment, the end effector 50 has a chisel shape. A power cable 42 couples the ultrasonic handpiece assembly 332 to an ultrasonic generator (e.g., ultrasonic generator 12 shown in FIG. 1).

In one embodiment, the ultrasonic instrument 330 comprises a strike plate assembly 336. The strike plate assembly 336 comprises a flange or strike plate 338 defining a strikeable surface 340 having a flange area configured to receive or accommodate a mechanical impact and impart energy into the end effector 50 when the ultrasonic hand piece assembly 332 is in a powered or an unpowered state. The mechanical impact or strike may be delivered manually or with an osteotome mallet, for example. The strike plate 338 is suitable to receive a typical blow or strike from an osteotome mallet (e.g., similar to the mallet 204 shown in FIG. 7) at the strikeable surface 330 without damaging the ultrasonic hand piece assembly 332. In the illustrated embodiment, the strike plate assembly 336 comprises one or more longitudinally extending elongate support members 342 and a transverse compression member 344 to removably couple the strike plate assembly 336 to the housing 334. In one embodiment, the transverse compression member 344 may be configured as a radially assembled "C" or "U" shaped compression member. The transverse compression member 344 may be radially assembled on the groove 346 by slidingly pressing the transverse compression member 344 in the direction indicated by arrow 350 to engage and compress the groove 346 formed on the housing 334. The transverse compression member 344 may be readily removed by applying a force in the direction indicated by arrow 348. The transverse compression member 344 may be configured to compress the groove 346 with a force suitable to withstand strikes against the strikeable surface 340 while it is engaged. In one embodiment, the groove 346 may be a groove extending substantially around a circumferential portion or circular cross-sectional portion of the housing 334.

As previously discussed with reference to FIG. 10, in use, a clinician may employ the ultrasonic instrument 330 in a powered state using the ultrasonic vibrations generated by the transduction portion 18 to cut and coagulate relatively soft musculoskeletal tissue using the chisel shaped end effector 50. With the ultrasonic instrument 330 in a powered or an unpowered state, the clinician can employ an osteotome mallet to strike the strikeable surface 340 to chisel relatively hard musculoskeletal tissue such as bone.

FIG. 12 illustrates a side view of one embodiment of an ultrasonic instrument 360 comprising an impact zone. In the illustrated embodiment, the ultrasonic instrument 360 extends longitudinally along axis "L" between a distal end 122 and a proximal end 124. In one embodiment, the ultrasonic instrument 360 comprises an ultrasonic hand piece assembly 362. Ultrasonically, the hand piece assembly 362 is substantially similar to and operates in substantially the same manner as the handpiece assembly 60 described in FIG. 1. The ultrasonic instrument 360 comprises a housing 364, a transduction portion 18, and an acoustic assembly 24 portion, as previously discussed with reference to FIG. 1. In one embodiment, the housing 364 comprises a substantially circular cross-section (not shown). The ultrasonic instrument 360 comprises the sheath 58 containing the ultrasonic transmission waveguide 46 therein (as previously discussed in FIG. 1) coupled to the end effector 50. In the illustrated embodiment, the end effector 50 has a chisel shape. A power cable 42 couples the ultrasonic handpiece assembly 362 to an ultrasonic generator (e.g., ultrasonic generator 12 shown in FIG. 1).

In one embodiment, the ultrasonic instrument 360 comprises a strike plate assembly 366. The strike plate assembly 366 comprises a flange or strike plate 368 defining a strikeable surface 370 having a flange area configured to receive or accommodate a mechanical impact and impart energy into the end effector 50 when the hand piece assembly 362 is in a powered or an unpowered state. The mechanical impact or strike may be delivered manually or with an osteotome mallet, for example. The strike plate 368 is suitable to receive a typical blow or strike from an osteotome mallet (e.g., similar to the mallet 204 shown in FIG. 7) at the strikeable surface 370 without damaging the ultrasonic hand piece assembly 362. In the illustrated embodiment, the strike plate assembly 366 comprises one or more longitudinally extending elongate support members 372 a threaded connection 375. The threaded connection 375 is formed of internal female threaded portion 374 to engage a corresponding external male threaded portion 376 formed circumferentially around a circular cross-sectional portion of the housing 364. The strike plate assembly 366 may be engaged with the housing 364 by screwing the female threaded portion 374 over the male threaded portion 376. A stop 378 is rigidly attached or formed integrally with the housing 364 to contact distal wall portions 380 of the support members 372. The strike plate 368 comprises a sleeve 382 extending longitudinally from a proximal end to a distal end. The sleeve 382 comprises a flange 390 at a distal end to engage a compression spring element 384 positioned within the sleeve 382. The proximal end 386 of the support member 372 comprises a flange 388 formed to engage the proximal end of the compression spring element 384. The compression spring element 384 is positioned around the proximal end 386 of the support member 372. The proximal end of the strike plate 368 also comprises a ball 394 and a compression spring element 396 configured to engage and compress the surface of the ball 394 to retain the strike plate 386 in position.

As previously discussed with reference to FIGS. 10 and 11, in use, a clinician may employ the ultrasonic instrument 360 in a powered state using the ultrasonic vibrations generated by the transduction portion 18 to cut and coagulate relatively soft musculoskeletal tissue using the chisel shaped end effector 50. With the ultrasonic instrument 360 in a powered or an unpowered state, the clinician can employ an osteotome mallet to strike the strikeable surface 370 to chisel relatively hard musculoskeletal tissue such as bone.

FIG. 13 illustrates a side view of one embodiment of an ultrasonic instrument 400 comprising an impact zone. In the illustrated embodiment, the ultrasonic instrument 400 extends longitudinally along axis "L" between a distal end 122 and a proximal end 124. In one embodiment, the ultrasonic instrument 400 comprises an ultrasonic hand piece assembly 402. Ultrasonically, the hand piece assembly 402 is substantially similar to and operates in substantially the same manner as the handpiece assembly 60 described in FIG. 1. The ultrasonic instrument 400 comprises a housing 404, a transduction portion 18, and an acoustic assembly 24 portion, as previously discussed with reference to FIG. 1. In one embodiment, the housing 404 comprises a substantially circumferential cross-section (not shown). The ultrasonic instrument 400 comprises the sheath 58 containing the ultrasonic transmission waveguide 46 therein (as previously discussed in FIG. 1) coupled to the end effector 50. In the illustrated embodiment, the end effector 50 has a chisel shape. A power cord 42 couples the ultrasonic handpiece assembly 402 to an ultrasonic generator (e.g., ultrasonic generator 12 shown in FIG. 1).

In one embodiment, the ultrasonic instrument 400 comprises a strike plate assembly 406. The strike plate assembly 406 comprises a flange or strike plate 408 defining a strikeable surface 410 having a flange area configured to receive or accommodate a blow from a slide (slap) hammer 414. The slide hammer 414 has an opening extending longitudinally therethrough. The slide hammer 420 comprises a striking surface 422 at a distal end suitable to impart a blow to or strike the strikeable surface 410. A blow from the slide hammer 414 imparts energy into the end effector 50 when the hand piece assembly 402 is in a powered or an unpowered state. The strike plate 408 is suitable to receive a typical blow or strike from the slide hammer 414 at the strikeable surface 410 without damaging the ultrasonic hand piece assembly 402. In the illustrated embodiment, the strike plate assembly 406 comprises one or more longitudinally extending elongate support members 412 rigidly attached to the housing 404. The strike plate 408 is formed with a shaft 416 protruding from a distal end to a proximal end. The proximal end of the shaft 416 comprises a flange 418. The slide (slap) hammer 414 is slideably movable axially on the shaft 416 in the direction indicated by arrow 420.

As previously discussed with reference to FIGS. 10-12, in use, a clinician may employ the ultrasonic instrument 400 in a powered state using the ultrasonic vibrations generated by the transduction portion 18 to cut and coagulate relatively soft musculoskeletal tissue using the chisel shaped end effector 50. With the ultrasonic instrument 400 in a powered or an unpowered state, the clinician may strike the strikeable surface 410 manually or may employ an osteotome mallet to chisel relatively hard musculoskeletal tissue such as bone.

FIGS. 14-17 illustrate one embodiment of an ultrasonic instrument 450 comprising an end effector 452 at a distal end 122. The ultrasonic instrument 450 extends longitudinally along axis "L" between a distal end 122 and a proximal end 124. The end effector 452 comprises a non-vibrating clamp jaw 454 and an ultrasonic blade 456. In the embodiments illustrated in FIGS. 14-17, the clamp jaw 454 is pivotally mounted to pivot point 472 and is rotatable from a distal end to a proximal end as shown by arrow 458 to an open folded back position that leaves the ultrasonic blade 456 exposed for reshaping and coagulating tissue. The clamp jaw 454 is rotatable up to about 180° such that either in the open or the closed position, the clamp jaw 454 is substantially aligned with the longitudinal axis so as to be in line or in parallel with the longitudinal axis. The clamp jaw 454 is rotatable from a distal end to a proximal end as shown by arrow 459 to a closed position for squeezing the tissue between the blade 456 and the clamp jaw 454 against a side of the blade 456, to use the shearing action of the vibration to enhance tissue cutting/coagulating effects. FIG. 14 is a side perspective view of one embodiment of the ultrasonic instrument 450 with the clamp jaw 454 in a closed position. FIGS. 15 and 16 are side perspective views of the ultrasonic instrument 450 with the clamp jaw 454 in partially open positions. FIG. 17 is side perspective view of the ultrasonic instrument 450 with the clamp arm assembly in a closed position.

With reference now to FIGS. 14-17, the ultrasonic instrument 450 comprises an ultrasonic hand piece assembly 464. Ultrasonically, the hand piece assembly 464 is substantially similar to and operates in substantially the same manner as the ultrasonic handpiece assembly 60 described in FIG. 1. Accordingly, the ultrasonic hand piece assembly 464 also comprises a transduction portion 18 and an acoustic assembly 24 portion, as previously discussed with reference to FIG. 1. The ultrasonic instrument 450 comprises an outer tubular member or outer tube 462 that extends from the handpiece assembly 464 to a proximal end of the end effector 452. The outer tube 462 has a substantially circular cross-section and a longitudinal opening or aperture 466 to receive the clamp jaw 454 in its retracted or folded back position. An inner actuator tubular member or inner tube 468 extends longitudinally within the outer tube 462. The inner tube 468 has an opening extending longitudinally therethrough. The outer tube 462 and the inner tube 468 may be fabricated from stainless steel. It will be recognized that the outer tube 462 may be constructed from any suitable material and may have any suitable cross-sectional shape. The end-effector 452 is configured to perform various tasks, such as, for example, grasping tissue, cutting tissue and the like. It is contemplated that the end-effector 452 may be formed in any suitable configuration.

As previously discussed, the end-effector 452 comprises a non-vibrating clamp jaw 454 and an ultrasonic blade 456. A tissue engaging portion of the clamp arm assembly 454 comprises a clamp pad 470. The non-vibrating clamp jaw 454 is to grip tissue or compress tissue against the ultrasonic blade 456, for example.

The ultrasonic blade 456 may comprise a chisel shape and is suitable to cut and coagulate relatively soft musculoskeletal tissue and to chisel or drill relatively hard musculoskeletal tissue such as bone. Nevertheless, the ultrasonic blade 456 may be employed in various other therapeutic procedures. In one embodiment, the ultrasonic blade 456 may comprise a cutting chisel edge at a distal portion. The ultrasonic blade 456 is coupled to an ultrasonic transmission waveguide positioned within the outer tube 462.

The clamp jaw 454 is preferably pivotally mounted to the distal end of the outer tube 462 at pivot point 472 such that the clamp jaw 454 can rotate in the in an arcuate direction shown by arrows 458, 459. A pivot pin 474 is inserted through the pivot point 472. The distal end of the outer tube 462 comprises projections 476A and 476B that define corresponding holes 478A and 478B (not shown) to receive the pivot pin 474. The pivot pin 474 may be retained within the holes 478A, B in any suitable configuration. The inner tube 468 opening contains an actuator rod 490 that is mounted to a proximal end of the clamp jaw 454. When the actuator rod 490 is moved axially from the proximal end to the distal end in the direction indicated by arrow 482 the actuator rod 490 drives the clamp arm assembly to rotate about the pivot point 472 in the direction indicated by arrow 458 to its open position. A longitudinal channel 486 formed on a top surface of the clamp jaw 454 receives a longitudinal portion of the inner tube 468 therein when the clamp jaw 454 is in the open position. The axially moveable actuator rod 490 may be moved in any suitable manner and in one embodiment may be controlled by switch 480. When the actuator rod 490 is moved axially from the distal end to the proximal end in the direction indicated by arrow 484 the actuator rod 490 drives the clamp jaw 454 to rotate about the pivot point 472 in the direction indicated by arrow 459 to its closed or clamping position.

The clamp pad 470 is attached to the clamp jaw 454 and is for squeezing tissue between the ultrasonic blade 456 and the clamp jaw 454. The clamp pad 470 may be mounted to the clamp jaw 454 by an adhesive, or preferably by a mechanical fastening arrangement. Serrations 488 may be formed in the clamping surfaces of the clamp pad 470 and extend perpendicular to the axis of the ultrasonic blade 456 to allow tissue to be grasped, manipulated, coagulated and cut without slipping between the clamp jaw 454 and the ultrasonic blade 456.

The clamp pad 470 may be formed of a polymeric or other compliant material and engages the ultrasonic blade 456 when the clamp jaw 454 is in its closed position. Preferably, the clamp pad 470 is formed of a material having a low coefficient of friction but which has substantial rigidity to provide tissue-grasping capability, such as, for example, TEFLON®, a trademark name of E.I. Du Pont de Nemours and Company for the polymer polytetraflouroethylene (PTFE). The clamp pad 470 may be formed of other materials, such as, polyimide materials and/or other filled materials, for example, graphite or TEFLON filled polyimide materials. One example of a polyimide material may be VESPEL®, a trademark name of E.I. Du Pont de Nemours and Company. Polyimide provides a unique combination of the physical properties of plastics, metals, and ceramics, for example. In one embodiment, the clamp pad 470 may be formed of multiple components and multiple materials. For example, the clamp pad 470 may comprise one component formed of TEFLON and another component formed of polyimide. The clamp pad 470 may comprise a base material and at least two filler materials to allow the base material and the at-least-two filler materials to be chosen with a different hardness, stiffness, lubricity, dynamic coefficient of friction, heat transfer coefficient, abradability, heat deflection temperature, and/or melt temperature to improve the wearability of the clamp pad 470, which is important when high clamping forces are employed because the clamp pad 470 wears faster at higher clamping forces than at lower clamping forces. For example, a 15% graphite-filled, 30% PTFE-filled polyimide clamp pad 470 may provide substantially the same or better wear with a 4.5 pound clamping force as a 100% polytetrafluoroethylene clamp pad provides with a 1.5 pound clamping force. The advantage of a 15% graphite-filled, 30% PTFE-filled polyimide clamp pad 470 is increased heat resistance, which improves the overall wear resistance of the clamp pad 470. This polyimide-composite clamp pad has a useful heat resistance up about 800° F. to about 1200° F., as compared to a useful heat resistance up to about 660° F. of a PTFE clamp pad. Alternatively, other materials may be useful for a portion of the clamp pad 470, such as ceramics, metals, glasses and graphite.

In alternative embodiments, the clamp jaw 454 may be configured to retract rather than to fold back. In one embodiment, the ultrasonic blade 456 also may be configured to retract in any suitable manner.

FIGS. 18-20 illustrate one embodiment of an end effector that may be employed with the ultrasonic instrument 450 discussed in FIGS. 14-17. In the illustrated embodiment, the ultrasonic instrument 450 adapted and configured with the end effector 502 illustrated in FIGS. 18-20 is shown generally as ultrasonic instrument 500. One embodiment of the ultrasonic instrument 500 comprises the end effector 502 at a distal end 122. The ultrasonic instrument 500 extends longitudinally along axis "L" between a distal end 122 and a proximal end 124. The end effector 502 comprises a non-vibrating clamp jaw 504 and the ultrasonic blade 456. The clamp jaw 504 provides an increased mechanical advantage over the clamp jaw 454 of the end effector 452 shown in FIGS. 14-17. FIG. 18 is a top perspective view of one embodiment of the end effector 502 with the clamp arm assembly 504 in a closed position. FIG. 19 is a top perspective view of one embodiment of the end effector 502 with the clamp arm assembly 504 in an open position. FIG. 20 is an exploded view of one embodiment of the end effector 502 with the clamp jaw 504 in an open position.

With reference to FIGS. 18-20, the clamp jaw 504 is pivotally mounted at a pivot point 506 and is rotatable from a distal end to a proximal end as shown by arrow 458 to an open position that leaves the ultrasonic blade 456 exposed for reshaping and coagulating tissue. The clamp jaw 504 is rotatable from a distal end to a proximal end as shown by arrow 459 to a closed position for squeezing tissue between the blade 456 and the clamp jaw 504 against a side of the blade 456, to use the shearing action of the vibration to enhance tissue cutting/coagulating effects. The clamp jaw 504 comprises the clamp pad 470 configured with serrations 488 formed thereon that extend perpendicular to the axis "L" of the ultrasonic blade 456. The serrations 488 allow tissue to be grasped, manipulated, coagulated, and cut without slipping between the clamp jaw 504 and the ultrasonic blade 456.

The ultrasonic instrument 500 comprises the outer tube 462. As previously discussed, the outer tube 462 has a substantially circular cross-section and the longitudinal opening or aperture 466 to receive the clamp jaw 504 in its retracted or folded back open position. The outer tube 462 is configured to receive a first inner tube 518 comprising a "D" shaped cross-section and defines an aperture 520 therein to receive a distal portion of an elongated member 512. The elongated member 512 comprises a pivot base member 515 and a channel 514. The channel 514 is configured to receive an actuator rod 516. The outer tube 462 contains a second inner tube 522 configured to receive an ultrasonic transmission waveguide 457 portion of the blade 456.

The pivot point 506 is provided at the distal end of the elongated member 512. The clamp jaw 504 is pivotally mounted to the pivot point 506 by a pivot pin 508 that is received through a first hole 510A, a second hole 510B, and a third hole 510C. The clamp jaw 504 is coupled to the actuator rod 516 with a first link 532A and a second link 532B. The first and second links 532A, B are coupled to the clamp jaw 504 with pin 534 received through a first hole 528B formed at a distal end of the first link 532A, a second hole 530B formed at a distal end of the second link 532B, and a slot 536 formed in the clamp jaw 504. The slot 536 is formed at an angle to the longitudinal axis "L" to enable the pin 534 some freedom of motion within the slot 536 during the rotation of the clamp jaw 504. The first and second links 532A, B are coupled to the actuator rod 516 with a pin 526 received through a first hole 528A formed at a proximal end of the first link 532A, a second hole 530A formed at a proximal end of the second link 532B, and a third hole 540 formed at a distal end 524 of the actuator rod 516.

FIGS. 21-24 illustrate the clamp jaw 504 transitioning from an open position in FIG. 21 to a closed position in FIG. 24 and intermediate positions in FIGS. 22 and 23. As shown, when the actuator rod 516 is advanced in the direction indicated by arrow 482, an advancing force is applied at the proximal ends of the first and second links 532A, B and the clamp jaw 504 is pivoted in a direction indicated by arrow 459 about pivot point 506 into the clamp jaw 504 closed position shown in FIG. 18. The clamp pad 470 now bears against the blade 456. When the actuator rod 516 is retracted in the direction indicated by arrow 484, a retracting force is applied at the proximal ends of the first and second links 532A, B and the clamp jaw 504 is pivoted in a direction indicated by arrow 458 about the pivot point 506 into the clamp jaw 504 open position illustrated in FIG. 19.

FIGS. 25 and 26 illustrate one embodiment of an end effector 552 that may be employed with the ultrasonic instrument 450 discussed in FIGS. 14-17. The ultrasonic instrument 450 adapted and configured with the end effector 552 illustrated in FIGS. 25 and 26 is generally referred to as ultrasonic instrument 550. One embodiment of the ultrasonic instrument 550 comprises an end effector 552 at a distal end 122. The ultrasonic instrument 550 extends longitudinally along axis "L" between a distal end 122 and a proximal end 124. The end effector 552 comprises a non-vibrating clamp jaw 504 and an ultrasonic blade 556. The clamp jaw 504 provides an increased mechanical advantage over the clamp jaw 454 of the end effector 452 shown in FIGS. 14-17. FIG. 25 is a top perspective view of one embodiment of the end effector 552 with the clamp arm assembly 504 in an open position. FIG. 26 is an exploded view of one embodiment of the end effector 552 with the clamp jaw 504 in an open position.

With reference to FIGS. 25 and 26, the end effector 552 comprises the clamp jaw 504 pivotally mounted at the pivot point 506 as previously described with respect to FIGS. 18-24. The end effector 552 comprises an ultrasonic blade 556 having a broad generally flat top surface 558 and a smooth generally round bottom surface 560 and is well-suited for coagulation and tissue reshaping applications. The broad generally flat top surface of the blade 556 is substantially wide and thin relative to the width and is well suited for removing muscle tissue from bone and may be referred to as an ultrasonic elevator blade.

The ultrasonic instrument 550 comprises the outer tube 462. As previously discussed, the outer tube 462 has a substantially circular cross-section and defines a longitudinal opening or aperture 466 to receive the clamp jaw 504 in its retracted or folded back open position. The outer tube 462 is configured to receive an inner tube 562 comprising a circular cross-section with a wall 554 defining a first aperture 566 to receive the elongated member 512 and a second aperture to receive an ultrasonic transmission waveguide portion 557 of the blade 556. The elongate member 512 comprises a pivot base member 515 and a channel 514. The channel 514 is configured to receive an actuator rod 516.

The pivot point 506 is formed at a distal end of the elongated member 512. The clamp jaw 504 is pivotally mounted to the pivot point 506 by the pivot pin 508 that is received through a first hole 510A, a second hole 510B, and a third hole 510C. The clamp jaw 504 is coupled to the actuator rod 516 with a first link 532A and a second link 532B. The first and second links 532A, B are coupled to the clamp jaw 504 with pin 534 received through a first hole 528B formed at a distal end of the first link 532A, a second hole 530B formed at a distal end of the second link 532B, and a slot 536 formed in the clamp jaw 504. The slot 536 is formed at an angle to the longitudinal axis "L" to enable the pin 534 some freedom of motion within the slot 536 as the clamp law 504 is rotated. The first and second links 532A, B are coupled to the actuator rod 516 with a pin 526 received through a first hole 528A formed at a proximal end of the first link 532A, a second hole 530A formed at a proximal end of the second link 532B, and a third hole 540 formed at a distal end 524 of the actuator rod 516. FIGS. 21-24 illustrate the clamp jaw 504 transitioning from an open position in FIG. 21 to a closed position in FIG. 24 and intermediate positions in FIGS. 22 and 23.

The devices disclosed herein can be designed to be disposed of after a single use, or they can be designed to be used multiple times. In either case, however, the device may be reconditioned for reuse after at least one use. Reconditioning can include any combination of the steps of disassembly of the device, followed by cleaning or replacement of particular elements, and subsequent reassembly. In particular, the device may be disassembled, and any number of particular elements or components of the device may be selectively replaced or removed in any combination. Upon cleaning and/or replacement of particular components, the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam, autoclaving, soaking in sterilization liquid, or other known processes.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:
1. A surgical instrument, comprising:
  a sheath;
  an elongated vibrational transmission waveguide positioned at least partially within the sheath, the waveguide defining a longitudinal axis and configured to transmit vibrations along the longitudinal axis at a predetermined wavelength, the waveguide comprising:
    a distal end;
    a proximal end;
    at least one node defined between the proximal end and the distal end; and
    at least one anti-node defined between the proximal end and the distal end, wherein the locations of the at least one node and the at least one anti-node between the proximal end and the distal end are determined by the predetermined wavelength of the vibrations;
  an end effector acoustically coupled to and extending from the distal end of the waveguide, wherein the end effector comprises:
    an end; and
    a distal-most anti-node positioned at the end of the end effector;

at least one strike surface formed on the proximal end, the at least one strike surface being configured to receive vibratory energy in the form of mechanical impacts;

at least one compliant member extending between the sheath and the waveguide, wherein the at least one compliant member is located at the at least one node defined along the waveguide to isolate the vibrations from the sheath; and a cam and lobe arrangement positioned at the proximal end, wherein the cam is coupled to a generator to move the cam in a circular path, and wherein the lobe is in mechanical communication with the strike surface on at least one point on the circular path.

2. The surgical instrument of claim 1, wherein the generator comprises an electric motor.

3. The surgical instrument of claim 1, wherein the generator comprises a hydraulic motor.

4. The surgical instrument of claim 1, wherein the generator comprises a pneumatic motor.

5. The surgical instrument of claim 1, comprising a grip defining a longitudinal channel configured to engage a portion of the vibrational transmission waveguide at a distal end of the at least one strike surface.

6. A method for processing a surgical instrument for surgery, comprising:
obtaining the surgical instrument of claim 1;
sterilizing the surgical instrument; and
storing the surgical instrument in a sterile container.

7. A surgical instrument, comprising:
a sheath;
an elongated ultrasonic transmission waveguide positioned at least partially within the sheath, the waveguide defining a longitudinal axis and configured to transmit vibrations along the longitudinal axis at an ultrasonic wavelength, the waveguide comprising:
a distal end;
a proximal end;
a node defined between the proximal end and the distal end, wherein the location of the node between the proximal end and the distal end is determined by the ultrasonic wavelength of the vibrations; and
an anti-node defined between the proximal end and the distal end, wherein the location of the anti-node between the proximal end and the distal end is determined by the ultrasonic wavelength of the vibrations;
an end effector acoustically coupled to and extending from the distal end of the waveguide, wherein the end effector comprises:
an end; and
a distal-most anti-node positioned at the end of the end effector;
a strike plate coupled to the proximal end of the waveguide;
a drive plate moveably positioned adjacent to the strike plate, wherein the drive plate is configured to impart vibratory energy in the form of mechanical impacts to the strike plate, and wherein the strike plate couples the vibrations to the waveguide; and
a compliant member extending between the sheath and the waveguide, wherein the compliant member is located at the node of the waveguide to isolate the vibrations from the sheath:
wherein the drive plate comprises a cam, wherein the cam is coupled to a generator that operably moves the cam in a circular path, and wherein the cam is in mechanical communication with the strike surface on at least one point on the circular path.

8. The surgical instrument of claim 7, wherein the generator comprises a motor selected from a group of motors comprising: an electric motor, a hydraulic motor, and a pneumatic motor.

9. The surgical instrument of claim 7, comprising:
a housing to enclose the cam;
an annular projection on the waveguide, wherein the housing is mounted to the waveguide at the annular projection; and
a bushing around a portion of the waveguide, wherein the housing fits over the bushing.

10. A surgical instrument, comprising:
a sheath;
a waveguide positioned at least partially within the sheath and comprising:
a distal end;
a proximal end;
at least one node defined between the distal end and the proximal end;
at least one anti-node defined between the distal end and the proximal end; and
a longitudinal axis extending between the proximal end and the distal end, wherein the waveguide is configured to transmit ultrasonic vibrations along the longitudinal axis at a predetermined ultrasonic wavelength that establishes the locations of the at least one node and the at least one anti-node between the distal end and the proximal end of the waveguide;
an end effector acoustically coupled to and extending from the distal end, wherein the end effector comprises:
an end; and
a distal-most anti-node positioned at the end;
a strike surface coupled to the proximal end, wherein the strike surface is configured to receive vibratory energy in the form of mechanical impacts, and wherein the strike surface imparts the vibrations to the waveguide;
at least one compliant member extending between the sheath and the waveguide, wherein the at least one compliant member is located at the at least one node of the waveguide to isolate the vibrations from the sheath; and
a driver moveably positioned adjacent to the strike surface, wherein the driver is configured to impart vibratory energy in the form of mechanical impacts to the strike surface, wherein the driver rotates about a hub, and wherein rotation of the driver generates longitudinal vibrations along the waveguide.

11. The surgical instrument of claim 10, wherein the driver comprises a projection, and wherein the projection impacts the strike surface as the driver rotates about the hub.

12. The surgical instrument of claim 10, wherein the driver is coupled to a motor that generates rotation thereof.

* * * * *